United States Patent [19]

Lednicer

[11] 3,960,961
[45] June 1, 1976

[54] 4'-FLUORO-4-{[4-(PHENYL)CYCLOHEX-YL]AMINO}BUTYROPHENONES AND THE SALTS THEREOF

[75] Inventor: Daniel Lednicer, Portage, Mich.

[73] Assignee: The Upjohn Company, Kalamazoo, Mich.

[22] Filed: Feb. 2, 1973

[21] Appl. No.: 329,044

Related U.S. Application Data

[63] Continuation-in-part of Ser. No. 194,544, Nov. 1, 1971, abandoned, which is a continuation-in-part of Ser. No. 68,573, Aug. 31, 1970, abandoned.

[52] U.S. Cl. .................. 260/570.5 CA; 260/141; 260/239 B; 260/247.7 Z; 260/268 R; 260/293.72; 260/293.83; 260/295.5 S; 260/326.5 R; 260/340.7; 260/349; 260/456 R; 260/456 P; 260/471 C; 260/501.1; 260/501.12; 260/501.18; 260/556 A; 260/501.19; 260/556 AR; 260/562 A; 260/566 A; 260/556 AC; 260/567.6 M; 260/570 R; 260/570.5 C; 260/590 D; 260/611 A; 260/68 R; 424/244; 424/250; 424/274; 424/316; 424/266; 424/330; 424/267

[51] Int. Cl.² .......................... C07C 97/10

[58] Field of Search .......... 260/570.5 CA, 570.5 C, 260/511.18, 567.6 M, 295.5 S, 501.12, 501.15

[56] References Cited
FOREIGN PATENTS OR APPLICATIONS
2,139,239   3/1972   Germany .................. 260/570.5

OTHER PUBLICATIONS
Lednicer et al., "Journal Medicinal Chem.", vol. 15, No. 12, pp. 1240–1243 (1972).

Primary Examiner—Robert V. Hines
Attorney, Agent, or Firm—John T. Reynolds; William A. Hodes

[57] ABSTRACT

This invention relates to novel 4-phenylcyclohexylamines embraced by the formula

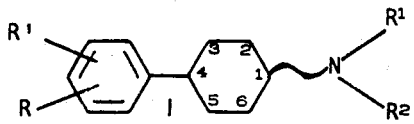

wherein ~ is a generic expression denoting cis and trans stereoconfiguration and mixtures thereof; R is selected from the group consisting of alkyl of from one through four carbon atoms, fluorine, chlorine, bromine, trifluoromethyl, nitro and alkoxy of from one through four carbon atoms; R' and $R^1$ are selected from the group consisting of hydrogen and alkyl of from one through four carbon atoms; $R^2$ is selected from the group consisting of hydrogen, alkyl of from one through four carbon atoms, alkanoyl of from one through three carbon atoms, alkylsulfonyl of from one through three carbon atoms, arylsulfonyl of from six through ten carbon atoms, alkylcarbamoyl wherein alkyl is from one through four carbon atoms, alkoxycarbonyl wherein alkyl is from one through four carbon atoms, ring monosubstituted aroylalkyl wherein the substituents have the same meaning as R, above, aryl is from six through ten carbon atoms and alkyl is from one through six carbon atoms and bis (ring monosubstituted) arylalkyl wherein the substituents have the same meaning as R, above, aryl is from six through ten carbon atoms and alkyl is from one through six carbon atoms; $R^1$ and $R^2$ when taken together with —N< is a saturated heterocyclic amino radical selected from the group consisting of unsubstituted and monosubstituted pyrrolidino, piperidino, hexamethylenimino, morpholino and piperazino; and an acid addition salt thereof. It also relates to intermediates and processes for the preparation of the aforesaid novel compounds (1) and novel derivatives thereof. The systemic administration to humans and animals of the novel compounds (1) depresses their central nervous systems.

33 Claims, No Drawings

4'-FLUORO-4-{[4-(PHENYL)CYCLOHEXYL-]AMINO}BUTYROPHENONES AND THE SALTS THEREOF

CROSS REFERENCE TO RELATED APPLICATIONS

This application is a continuation-in-part of copending application Ser. No. 194,544, filed Nov. 1, 1971, and now abandoned, which is in turn a continuation-in-part of application Ser. No. 68,573, filed Aug. 31, 1970, now abandoned.

BRIEF SUMMARY OF THE INVENTION

The novel compounds of this invention, intermediates therefor and processes for their production are prepared in accordance with the procedures of Processes A, B and C, respectively, described below.

Process A

This process is illustratively represented by the following sequence of formulae

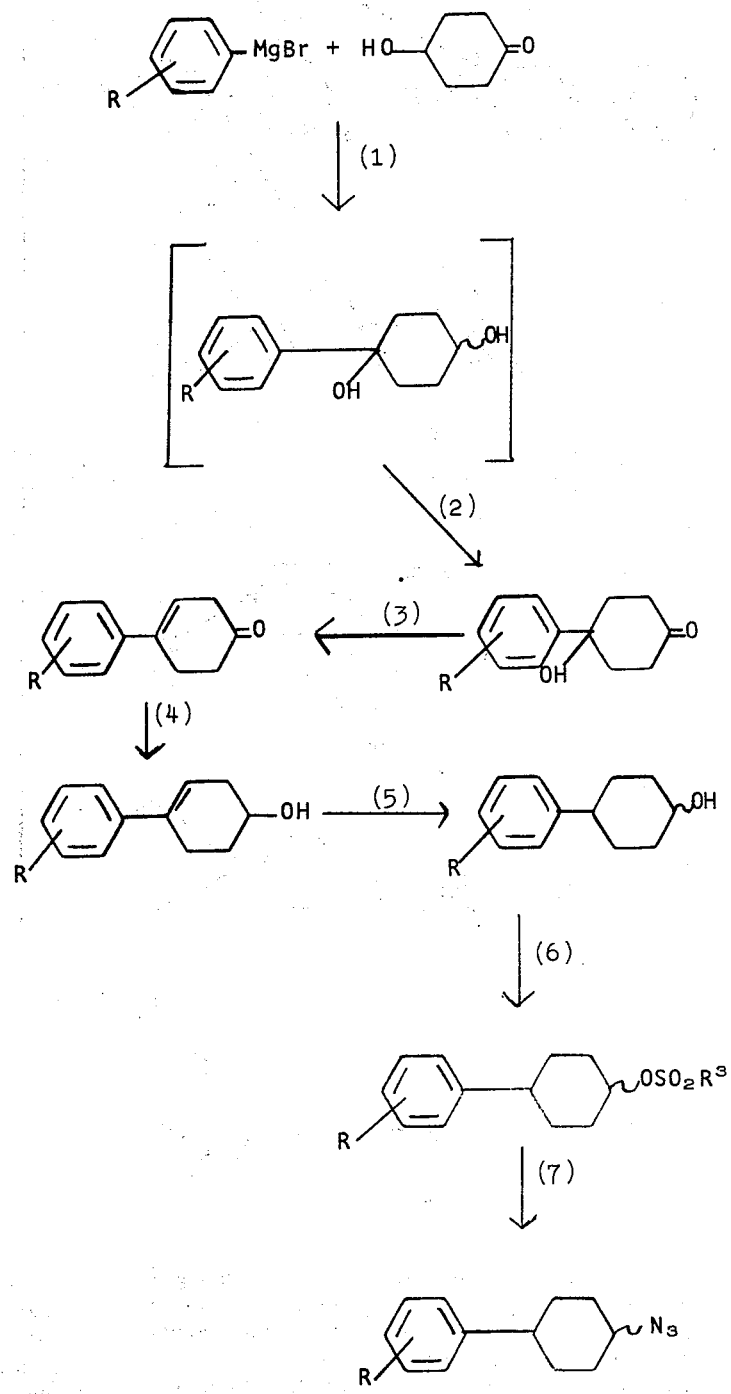

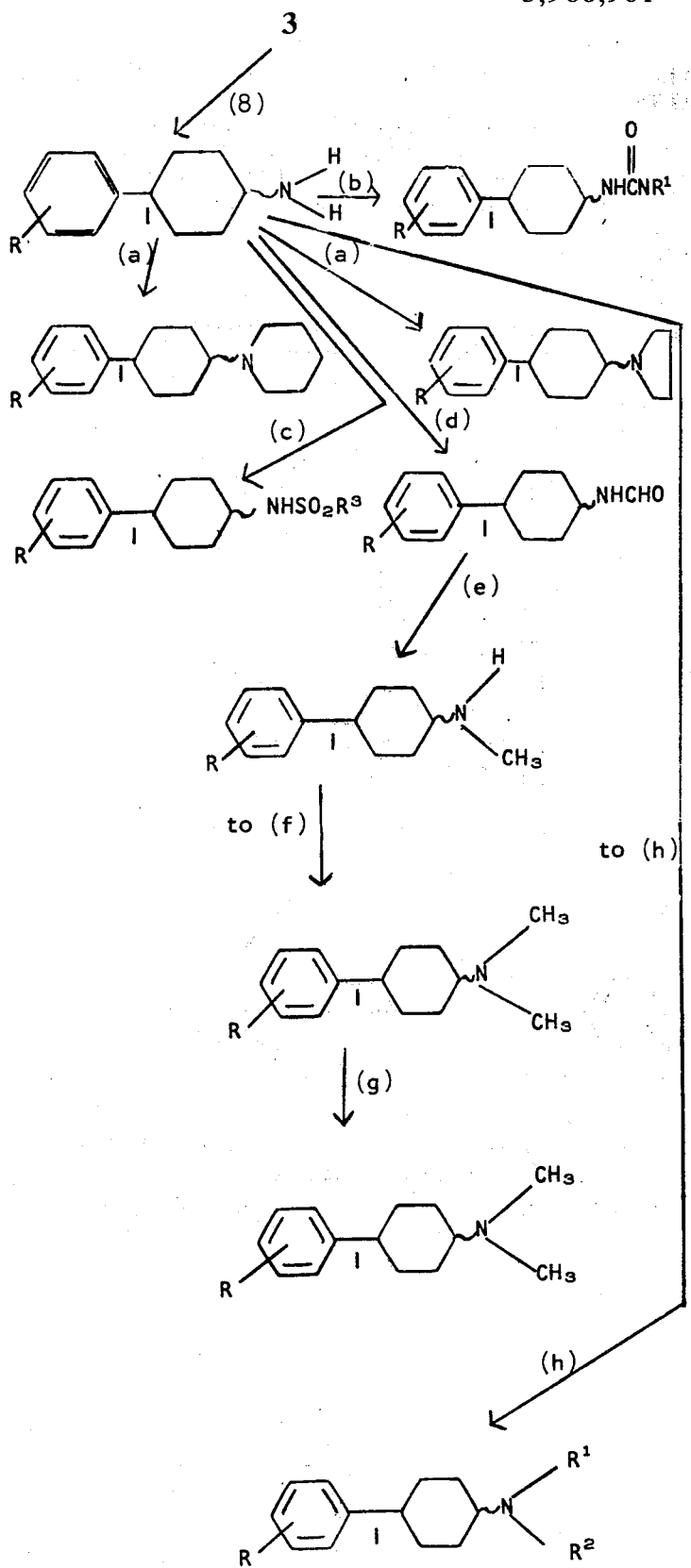

wherein ~, R, R¹ and R² have the same meaning as above and R³ is selected from the group consisting of alkyl of from one through three carbon atoms and aryl of from six through ten carbon atoms.

The compounds embraced by Formula I of the flow-sheet of Process A, above, are prepared by the procedures indicated therein, employing the methods and reactions described below.

1. The first step of the process for preparing the compounds first designated I in the above flow-sheet, i.e., the cis and trans 4-(substituted phenyl)cyclohexylamines wherein R¹ and R² are hydrogen, involves mixing a cooled substituted phenylmagnesium halide Grignard reagent (prepared in known manner) with the known 4-hydroxycyclohexanone, to yield the corresponding cis and trans substituted phenyl-1,4-cyclohexanediols.

2. The next step of the process comprises oxidizing (e.g., with an oxygenated hexavalent chromium compound such as sodium or potassium chromate, or with Jones reagent (chromium trioxide-sulfuric acid) at the 1-position of the cyclohexane ring of the cis and trans substituted phenyl-1,4-cyclohexanediols produced in step (1), to yield a corresponding substituted phenyl-4-hydroxycyclohexanone.

The starting substituted phenylmagnesium halide and 4-hydroxycyclohexanone can be converted directly to the corresponding substituted phenyl-4-hydroxycyclohexanone without isolation of the corresponding cis and trans substituted phenyl-1,4-cyclohexanediols prepared in step (1).

3. A substituted phenyl-4-hydroxycyclohexanone produced in step (2), on mixing with a strong acid (e.g., trifluoroacetic acid) at moderate (room) temperature, yields a corresponding 4-(substituted phenyl)-3-cyclohexen-1-one.

4. In this step of the process a 4-(substituted phenyl)-3-cyclohexen-1-one produced in step (3) is reduced (e.g., with sodium borohydride in an alkanol such as ethanol, at room temperature) at the 1-position of the cyclohexane ring, to yield a corresponding 4-(substituted phenyl)-3-cyclohexen-1-ol.

5. A 4-(substituted phenyl)-3-cyclohexen-1-ol produced in step (4) is reduced at the 3-position of the cyclohexane ring (e.g., with hydrogen in the presence of a catalyst such as palladium on charcoal) to yield the corresponding cis and trans 4-(substituted phenyl)cyclohexanols, which can be separated by chromatography into their respective isomers.

6. A cis (or trans) 4-(substituted phenyl)cyclohexanol produced in step (5) is converted, by treatment (preferably at low temperature) with an alkyl (or aryl) sulfonyl halide in the presence of an amine base such as pyridine, to a corresponding cis (or trans) 4-(substituted phenyl)cyclohexanol alkyl (or aryl) sulfonate.

7. In this step, a cis (or trans) 4-(substituted phenyl)cyclohexanol alkyl (or aryl) sulfonate resulting from step (6) in a solvent such as dimethylformamide, on the addition of sodium azide, followed by heating, gives a corresponding trans (or cis) 4-(substituted phenyl)cyclohexan-1-ylazide. In this step, inversion of the stereoconfiguration occurs, with the cis sulfonate being converted to the corresponding trans azide and vice-versa.

8. The final step of the process comprises reducing the azide ($N_3$) function of a trans (or cis) 4-(substituted phenyl)cyclohexan-1-ylazide produced in step (7) e.g., (1) by heating said compound with lithium aluminum hydride in a solvent such as tetrahydrofuran, or, (2) by shaking said compound with hydrogen and a catalyst such as palladium on charcoal in a solvent such as ethyl acetate, to yield a corresponding trans (or cis) 4-(substituted phenyl)cyclohexylamine (I) in its free base form. (This reaction takes place without change of stereoconfiguration.) On treating an ether extract of a thus produced compound with a slight excess of a suitable acid, the acid addition salt form is obtained.

The free base or acid addition salt forms of the trans (or cis) 4-(substituted phenyl)cyclohexylamines (the compounds first designated I in the above flow-sheet), obtained as in final step (8), can be employed as starting materials for producing a variety of derivatives thereof, in accordance with the methods described in (a) through (i) that follow.

a. Heating (e.g., under reflux) a trans (or cis) 4-(substituted phenyl)cyclohexylamine (I) with a dihaloalkane to give a corresponding trans (or cis) 1-[4-(substituted phenyl)cyclohexyl]single ring nitrogen containing heterocyclic compound (I). For example, heating a trans (or cis) 4-(substituted phenyl)cyclohexylamine (I) with 1,5-diiodopentane, 1,4-dibromobutane or 1,6-diiodohexane, yields, respectively, trans (or cis) 1-[4-(substituted phenyl)cyclohexyl]piperidine (I), trans (or cis) 1-[4-substituted phenyl)cyclohexyl]pyrrolidine (I), or trans (or cis) 1-[4-(substituted phenyl)cyclohexyl]hexamethylenimine (I). Dissolving a thus produced compound in ether and treating it with an ethereal solution of an appropriate acid gives the corresponding acid addition salt.

b. Mixing the free base form of a trans (or cis) 4-(substituted phenyl)cyclohexylamine (I) with an alkylisocyanate (e.g., methylisocyanate, ethylisocyanate, butylisocyanate, etc.) at room temperature, yields a corresponding trans (or cis) 1-[4-(substituted phenyl)cyclohexyl]-3-alkylurea (I).

c. Mixing, e.g., in a solvent such as tetrahydrofuran, at room temperature, the free base form of a trans (or cis) 4-(substituted phenyl)cyclohexylamine (I) with an alkyl (or aryl) sulfonyl halide (such as methanesulfonyl chloride or toluenesulfonyl bromide) in the presence of a tertiary amine base (such as triethylamine), yields a corresponding trans (or cis) N-[4-(substituted phenyl)cyclohexyl]alkyl (or aryl) sulfonamide (I).

d. Heating a mixture of the free base form of a trans (or cis) 4-(substituted phenyl)cyclohexylamine (I) and ethyl formate (e.g., under reflux), yields a corresponding trans (or cis) N-[4-(substituted phenyl)cyclohexyl]formamide (I).

e. Reducing a trans (or cis) N-[4-(substituted phenyl)cyclohexyl]formamide (I), prepared as in (d), above, for example, by heating it in a solvent such as tetrahydrofuran (e.g., under reflux) with lithium aluminum hydride, yields a corresponding trans (or cis) N-methyl-[4-(substituted phenyl)cyclohexyl]amine (I). Dissolving a thus produced compound in ether and treating it with an ethereal solution of an appropriate acid gives a corresponding acid addition salt thereof.

f. Mixing in the cold with a tertiary amine base (such as triethylamine), a cold solution of the free base form of a trans (or cis) N-methyl-[4-(substituted phenyl)cyclohexyl]amine (I), prepared as (e), above, for example, with an alkylhaloformate (such as methyl chloroformate, ethyl chloroformate, propyl chloroformate, butyl chloroformate and the isomeric forms thereof), yields a corresponding trans (or cis) N-methyl-4-(substituted phenyl)cyclohexane-1-carbamic acid alkyl ester (I).

g. Reducing a trans (or cis) N-methyl-4-(substituted phenyl)cyclohexane-1-carbamic acid alkyl ester (I), prepared as in (f), above, for example, by heating it in a solvent such as tetrahydrofuran (e.g., under reflux) with lithium aluminum hydride, gives a corresponding trans (or cis) N,N-dimethyl-4-(substituted phenyl)cyclohexylamine (I). A thus produced compound is converted to its acid addition salt by dissolving it in an ethereal solution of an appropriate acid.

h. A compound represented in the above flow-sheet by the formula

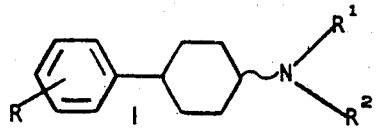

wherein ~, R and R¹ can have any of the meanings indicated therefor and R² is ring monosubstituted aroylalkyl wherein the substituents have the same meaning as R, aryl is from six through ten carbon atoms and alkyl is from one through six carbon atoms, can be prepared from a corresponding trans (or cis) 4-(substituted phenyl)cyclohexylamine (I) by the general procedure that follows.

The process for the production of such an aroylalkyl compound selected from the group consisting of the free bases and acid addition salts of a compound of the formula

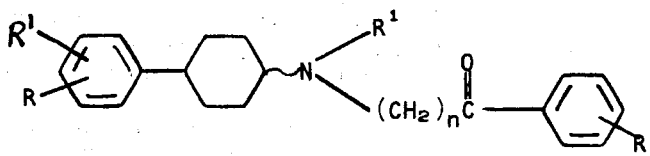

wherein ~ is a generic expression denoting cis and trans stereoconfiguration and mixtures thereof, R' and R is selected from the group consisting of hydrogen, alkyl of from one through four carbon atoms, fluorine, chlorine, bromine, trifluoromethyl, nitro and alkoxy of from one through four carbon atoms, R¹ is selected from the group consisting of hydrogen and alkyl of from one through four carbon atoms and n is selected from the group consisting of the integers one through six, comprises reacting a compound selected from the group consisting of the free bases and acid addition salts of a corresponding 4-(substituted phenyl)cyclohexylamine (I) of the formula

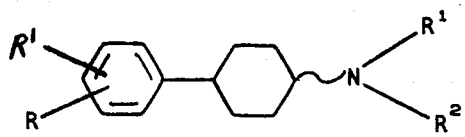

wherein ~, R, R' and R¹ have the same meaning as above and R² is hydrogen with a corresponding compound of the formula

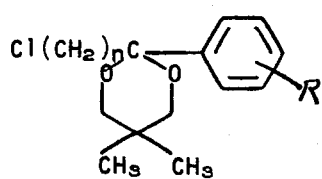

wherein R and n have the same meaning as above and hydrolyzing a thus produced compound.

A compound represented in the above flow-sheet by the formula

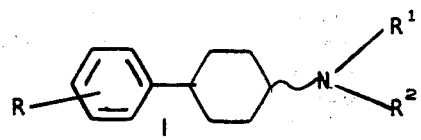

wherein ~, R and R¹ can have any of the meanings indicated therefor and R² is bis(ring monosubstituted-)arylalkyl wherein the substituents have the same meaning as R, aryl is from six through ten carbon atoms and alkyl is from one through six carbon atoms, can be prepared from a corresponding trans (or cis) 4-(substituted phenyl)cyclohexylamine (I) by the general procedure that follows.

The process for the production of such an arylalkyl compound selected from the group consisting of the free bases and acid addition salts of a compound of the formula

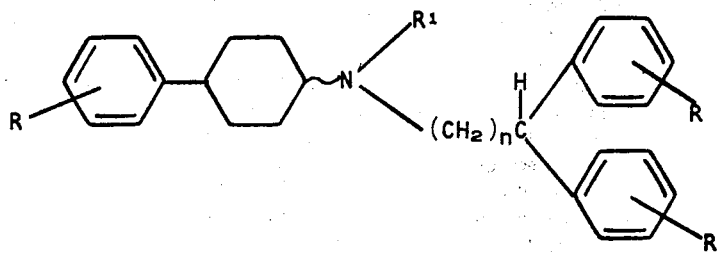

wherein ~ is a generic expression denoting cis and trans stereoconfiguration and mixtures thereof, R is selected from the group consisting of hydrogen, alkyl of from one through four carbon atoms, fluorine, chlorine, bromine, trifluoromethyl and alkoxy of from one through four carbon atoms R¹ is selected from the group consisting of hydrogen and alkyl of from one through four carbon atoms and n is selected from the group consisting of the integers one through six, comprises reacting a compound selected from the group consisting of the free bases and acid addition salts of a corresponding 4-(substituted phenyl)cyclohexylamine (I) of the formula

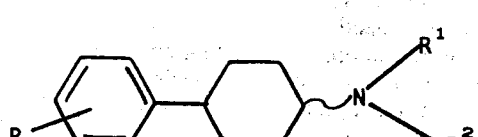

wherein ~, R and R¹ have the same meaning as above and R² is hydrogen with a corresponding compound of the formula

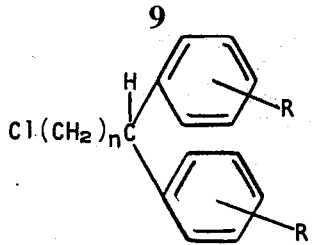

wherein R and n have the same meaning as above.

Process B

This process is illustratively represented by the following sequence of formulae

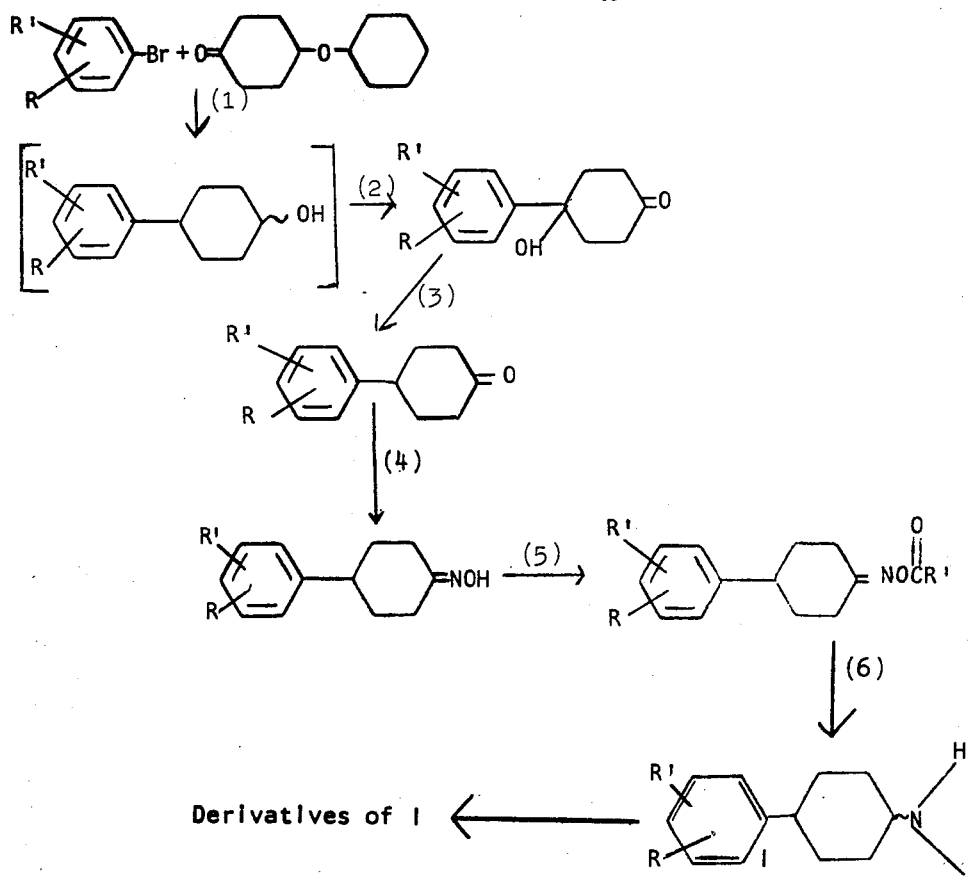

Derivatives of I ←

(Prepared in the manner described for the corresponding monosubstituted compounds in Process A, above.) ~, R and R' have the same meaning as above.

The compounds embraced by Formula I of the flow-sheet of Process B, above, are prepared by the procedures indicated therein, employing the methods and reactions described below.

1. The first step of the process for preparing the compounds designated I in the above flow-sheet, i.e., the cis and trans 4-(disubstituted phenyl)hexylamines wherein $R^1$ and $R^2$ are hydrogen, comprises mixing a cooled disubstituted phenyl halide (prepared in known manner) with 4-[(tetrahydropyran-2-yl)oxy]cyclohexanone (prepared by mixing 4-hydroxycyclohexanone with dihydropyran in the presence of a catalyst such as p-toluenesulfonic acid), to yield corresponding cis and trans (disubstituted phenyl)-1,4-cyclohexanediols.

2. The next step of the process comprises oxidizing (e.g., with Jones reagent) at the 1-position of the cyclohexane ring of the cis and trans 4-(disubstituted phenyl)-1,4-cyclohexanediols produced in step (1), to yield a corresponding 4-(disubstituted phenyl)-4-hydroxycyclohexanone.

The starting 4-[(tetrahydropyran-2-yl)oxy]cyclohexanone and disubstituted phenyl halide can be converted directly to the corresponding 4-(disubstituted phenyl)-4-hydroxycyclohexanone without isolation of the corresponding cis and trans (disubstituted phenyl)-1,4-cyclohexanediols prepared in step (1).

3. A 4-(disubstituted phenyl)-4-hydroxycyclohexanone produced in step (2), on mixing with a strong acid (e.g., trifluoroacetic acid) at moderate (room) temperature, yields a corresponding 4-(disubstituted phenyl)-cyclohexanone.

4. In this step of the process a 4-disubstituted phenyl)cyclohexanone produced in step (3) is oximated, e.g., by heating (preferably at reflux temperature) with hydroxylamine (or an acid addition salt thereof, such as the hydrochloride, and an alkali metal hydroxide, such as potassium hydroxide) in a solvent such as tetrahydrofuran, to yield a corresponding 4-(disubstituted phenyl)cyclohexanone oxime.

5. A 4-(disubstituted phenyl)cyclohexanone oxime produced in step (4), on mixing with an anhydride of a hydrocarbon carboxylic acid in the presence of an esterification catalyst (e.g., pyridine) at moderate (room) temperature, yields a corresponding 4-(disubstituted phenyl)cyclohexanone oxime acylate.

6. The final step of the process comprises reducing the oxime function of a 4-(disubstituted phenyl)cyclohexanone acylate produced in step (5), e.g., by reaction with borane in a solvent such as tetrahydrofuran, preferably at low temperature, to yield a corresponding trans (and cis) 4-(disubstituted phenyl)cyclohexylamine (1) In its free base form. On treating an ether extract of a thus produced compound with a slight excess of a suitable acid, the corresponding acid addition salt form is obtained.

The free base or acid addition salt form of the trans (or cis) 4-(disubstituted phenyl(cyclohexylamines (1)

obtained as in final step (6), can be employed as starting materials for producing a wide variety of derivatives (1) thereof, in accordance with the methods described above in (a) through (i) following the explanation of steps (1) through (8) of Process A) for preparing numerous derivatives of the corresponding trans (or cis) 4-(monosubstituted phenyl)cyclohexylamines (1).

Process C

This process is illustratively represented by the following sequence of formulae

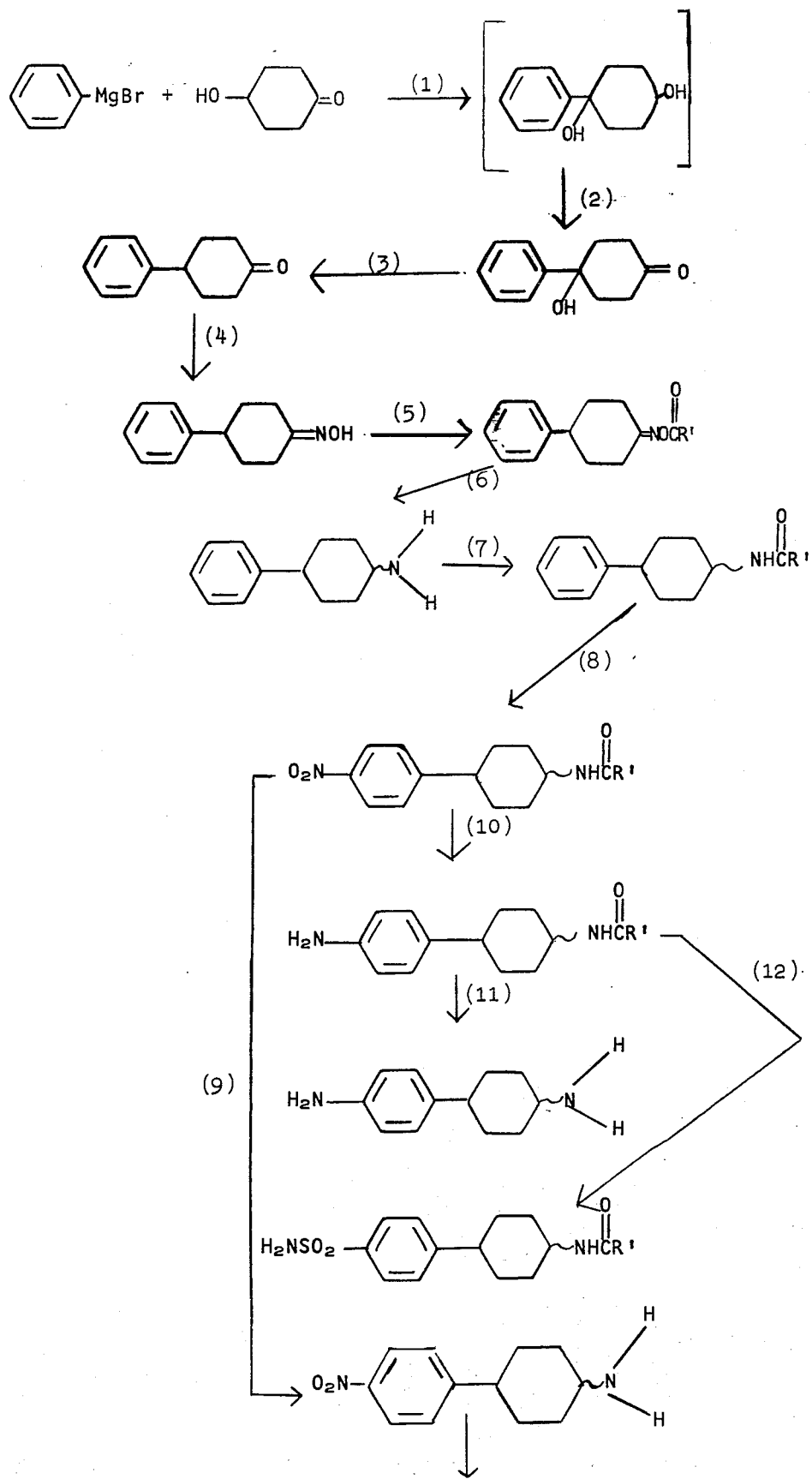

Derivatives of 1 (Prepared in the manner described for those of Process A, above.)
— and R' have the same meaning as above.

The compounds embraced by Formula 1 of the flowsheet of Process C, above, are prepared by the procedures indicated therein, employing the methods and reactions described below.

1. The first step of the process for preparing the compounds designated 1 in the above flow-sheet, i.e., the cis and trans 4-(p-nitrophenyl)cyclohexylamines wherein R' and R² are hydrogen, comprises mixing a cooled phenylmagnesium halide Grignard reagent with 4-hydroxycyclohexanone, to yield cis and trans 4-phenyl-1,4-cyclohexanediols.

2. The next step of the process comprises oxidizing (e.g., with Jones reagent) at the 1-position of the cyclohexane ring of the cis and trans 4-phenyl-1,4-cyclohexanediols produced in step (1), to yield 4-phenyl-4-hydroxycyclohexanone.

The starting phenylmagnesium halide and 4-hydroxycyclohexanone can be converted directly to 4-phenyl-4-hydroxycyclohexanone without isolation of the cis and trans 4-phenyl-1,4-cyclohexanediols prepared in step (1).

3. The phenyl-4-hydroxycyclohexanone produced in step (2), on mixing with a strong acid such as trifluoroacetic acid at moderate (room) temperature, yields 4-phenyl-3-cyclohexen-1-one. The thus produced compound (without isolation) is reduced at the 3-position of the cyclohexane ring, (e.g., with hydrogen in the presence of a catalyst such as palladium on charcoal) to yield 4-phenylcyclohexanone.

4. In this step the 4-phenylcyclohexanone produced in step (3) is oximated, e.g., by heating (preferably at reflux temperature) with hydroxylamine (or an acid salt thereof, such as the hydrochloride and an alkali metal hydroxide, such as potassium hydroxide) in a solvent (e,.g., ethanol), to yield 4-phenylcyclohexanone oxime.

5. The 4-phenylcyclohexanone oxime produced in step (4) on mixing with an anhydride of a hydrocarbon carboxylic acid in the presence of an esterification catalyst such as pyridine, at moderate (room) temperature, yields a corresponding 4-phenylcyclohexanone oxime acylate.

6. In this step, the oxime function of a 4-phenylcyclohexanone oxime acylate resulting from step (5) is subjected to the Birch reduction (e.g., by reaction with an alkali metal, preferably lithium, in liquid ammonia, using solvents such as tetrahydrofuran, dioxane, ether, t-butanol, ethanol, and the like, or mixtures thereof), to yield trans (and cis) 4-phenylcyclohexylamine in its free base form. On treating an ether extract of a thus produced compound with a slight excess of a suitable acid, the corresponding acid addition salt form is obtained.

7. A trans (or cis) 4-phenylcyclohexylamine obtained in step (6), on mixing with an anhydride of a hydrocarbon carboxylic acid in the presence of an esterification catalyst, such as pyridine, at moderate (room) temperature, yields a corresponding trans( or cis) 4-phenylcyclohexylamine acylamide.

8. In this step, a trans (or cis) 4-phenylcyclohexylamine acylamide resulting from step (7) is mixed (preferably at low temperature) in a solvent (such as trifluoroacetic acid) with nitric acid, to give a corresponding trans (or cis) N-[4-(p-nitrophenyl)cyclohexyl]acylamide.

9. A trans (or cis) N-[4-(p-nitrophenyl)cyclohexyl]-acylamide produced in step (8) is hydrolyzed, e.g., by dissolving it in an alkanol (such as methanol) containing a strong acid (such as hydrochloric acid) and heating the solution (preferably under reflux), to give a corresponding trans (or cis) 4-(p-nitrophenyl)cyclohexylamine (I) in its free base form. On treating an ether extract of a thus produced compound with a slight excess of a suitable acid, the corresponding acid addition salt form is obtained.

The free base or acid addition salt form of the trans (or cis) 4-(p-nitrophenyl)cyclohexylamine (I) obtained in step (9), can be employed as starting material for producing a wide variety of derivatives (I) thereof, in accordance with the methods described above in (a) through (I) (following the explanation of steps (1) through (8) of Process A) for preparing numerous derivatives of the corresponding trans (or cis) 4-(p-nitrophenyl)cyclohexylamines (I).

10. A trans (or cis) N-[4-(p-nitrophenyl)cyclohexyl]-acylamide produced in step (8) in a solvent such as ethanol, on hydrogenation in the presence of a catalyst (e.g., Adams' platinum dioxide catalyst), yields a corresponding trans (or cis) N-[4-(p-aminophenyl)cyclohexyl]acylamide.

11. A trans (or cis) N-[4-(p-aminophenyl)cyclohexyl]-acylamide obtained in step (10) in a solvent such as tetrahydrofuran, on reduction of its carbonyl function, e.g., by heating with lithium aluminum hydride, gives a corresponding trans (or cis) 4-(p-aminophenyl)-N-alkylcyclohexylamine.

12. A trans (or cis)N-[4-(p-aminophenyl)cyclohexyl]-acylamide resulting from step (10)is diazotized, e.g., by mixing it in the cold with a strong acid (such as hydrochloric acid), water and aqueous sodium nitrite; the resulting solution is added to an organic acid (e.g., acetic acid) containing cuprous chloride and then saturated with sulfur dioxide, to give a corresponding sulfonyl chloride derivative; on saturation with ammonia said derivative yields a corresponding trans (or cis) N-[4-(p-sulfamoylphenyl)cyclohexyl]acylamide.

Examples of alkoxy of from one through four carbon atoms are methoxy, ethoxy, propoxy and butoxy and the isomeric forms thereof. Examples of alkyl of from one through four carbon atoms are methyl, ethyl, propyl and butyl and the isomeric forms thereof. Examples of alkanoyl of from one through three carbon atoms are formyl, acetyl and propanoyl. Examples of alkylsulfonyl of from one through three carbon atoms are methanesulfonyl, ethanesulfonyl and propanesulfonyl and the isomeric forms thereof. Examples of arylsulfonyl of from six through ten carbon atoms are benzenesulfonyl, toluenesulfonyl and naphthalenesulfonyl. Examples of alkylcarbamoyl wherein alkyl is from one through four carbon atoms are methylcarbamoyl, ethylcarbamoyl, propylcarbamoyl and butylcarbamoyl and the isomeric forms thereof. Examples of alkoxycarbonyl wherein alkyl is from one through four carbon atoms are methoxycarbonyl, ethoxycarbonyl, propoxycarbonyl and butoxycarbonyl and the isomeric forms thereof. Examples of ring monosubstituted aroylalkyl wherein the substituents are selected from the group consisting of hydrogen, alkyl of from one through four carbon atoms, fluorine, chlorine, bromine, trifluoromethyl and alkoxy of from one through four carbon atoms, aryl is from six through ten carbon atoms and alkyl is from one through six carbon atoms are 4-oxo-4-(p-fluorophenyl)-butyl, 4-oxo-4-(o-propoxy-α-naphthyl)butyl, 2-oxo-2-(m-ethyl-α-naphthyl)ethyl, 3-oxo-3-(p-trifluoromethylphenyl)-propyl, 5-oxo-5-(o-ethoxyphenyl)pentyl, and the isomeric forms thereof. Examples of bis (ring monosubstituted) arylalkyl wherein the substituents are selected from the group consisting of hydrogen, alkyl of from one through four carbon atoms, fluorine, chlorine, bromine, trifluoromethyl and alkoxy of from one through four carbon atoms, aryl is from six through ten carbon atoms and alkyl is from one through six carbon atoms are 4,4-bis(p-fluorophenyl)-butyl, 2,2-bis(m-ethoxy-α-naphthyl)ethyl, 4,4-bis(p-tolyl)-butyl, 3,3-bis(o-trifluoromethylphenyl)-propyl and the isomeric forms thereof. Examples of unsubstituted and monosubstituted pyrrolidino, piperidino, hexamethylenimino, morpholino and piperazino are pyrrolidino, 2-methylpyrrolidino, 2-ethylpiperidino, hexamethylenimino, 3-methoxyhexamethylenimino, morpholino, 2-methylmorpholino, 2-ethoxymorpholino, 3-ethylmorpholino, piperazino, 2-methylpiperazino and 3-isopropylpiperazino.

The novel 4-phenylcyclohexylamines of Formula I exist either in the non-protonated (free base) form or in the protonated (acid addition salt) form, depending on the pH of the enbvironment. They form stable protonates, i.e., acid addition salts, on neutralization of the free base form with suitable acids, for example, hydrochloric, hydrobromic, sulfuric, phosphoric, nitric, acetic, propionic, palmitic, benzoic, salicylic, hexynoic, phenylbutyric, naphthoic, glycolic, succinic, nicotinic, tartaric, maleic, malic, pamoic, methanesulfonic, cyclohexanesulfonic, picric and lactic acid, and the like. Conversely, the free base of the novel compounds of Formula I can be obtained from a salt (e.g., from the hydrochloride or sulfate salts) by neutralization with a base such as sodium hydroxide, extracting with an immiscible solvent, for example chloroform, drying the extract, for example with anhydrous sodium sulfate, and removing the solvent by evaporation.

All of the compounds included within Formula I of the flow-sheet, above, can be isolated from their respective reaction mixtures by conventional means, for example, when a water-miscible solvent is used, by pouring the reaction mixture into water and separating the resulting precipitate by filtration or by extraction with water-immiscible solvents. Additional purification of the products can be accomplished by conventional means, for example, by elution chromatography from an adsorbent column with a suitable solvent such as acetone, ethyl acetate, ether, methylene chloride and Skellysolve B (hexanes), mixtures and combinations of these solvents; also by gradient elution chromatography from an adsorbent column with a suitable mixture of solvents, such as, methylene chlorine-Skellysolve B, acetone-Skellysolve B, and the like.

The free bases and acid addition salts of the novel compounds of Formula I are useful as central nervous system (CNS) depressants when administered to humans and animals. They possess tranquilizing activity and are consequently useful in humans for controlling anxiety and schizophrenia; in animals the aforesaid compounds are useful for their calming effects and can be given to reduce anxiety and agressive behavior. These compounds have been shown to possess CNS depressing activity via the loss of righting reflex, traction, chimney, dish and pedestal tests carried out in the manner described by Boissier et al. in Medicina Experimentalis 4, 145 (1961). The aforesaid novel compounds of Formula I behave as CNS depressants by virtue of lowering the concentration of catecholamine in the heart and brain.

The compounds of Formula I of the invention can be prepared and administered to humans, mammals, birds and animals, in a wide variety of oral or parenteral dosage forms, single or in admixture with other coacting compounds, in doses of from about 0.1 to about 100 mg./kg., depending on the severity of the condition being treated and the recipient's response to the medication. They can be administered with a pharmaceutical carrier which can be a solid material or a liquid in which the compound is dissolved, dispersed or suspended. The solid compositions can take the form of tablets, powders, capsules, pills, or the like, preferably in unit dosage forms for simple administeration or precise dosages. The liquid compositions can take the form of solutions, emulsions, suspensions, syrups or elixiers.

DETAILED DESCRIPTION

The following examples describe the manner and process of making and using the invention and set forth the best method contemplated by the inventor of carrying out his invention, but are not construed as limiting the scope thereof.

Example 1: cis and trans 1-(p-methoxyphenyl)-1,4-cyclohexanediol

To an ice cooled solution of p-methoxyphenylmagnesium bromide (prepared from 13.5 g. p-bromoanisole and 1.75 g. of magnesium in 100 ml. of tetrahydrofuran) there is added 2.75 g. of 4-hydroxycyclohexanone [obtained as in J. Chem. Soc. 10 (1940)] in 30 ml. of tetrahydrofuran. Following 17 hours of standing at room temperature, 50 ml. of ammonium chloride is added. The organic layer is washed with water and brine and taken to dryness. The residue is suspended in 50 ml. of Skellysolve B and the solid collected on a filter. Two recrystallizations from ethyl acetate gives 1.14 g. of 1-(p-methoxyphenyl)-1,4-cyclohexanediol, melting at 155° to 158° C.

Anal. Calcd. for $C_{13}H_{18}O_3$: C, 70.24; H, 8.16. Found: C, 70.05; H, 7.95.

The mother liquors are combined, taken to dryness and chromatographed on 400 ml. of Florisil (synthetic magnesium silicate) and eluted with 10% acetone in skellysolve B. The crystalline fractions are combined and recrystallized from Skellysolve B to yield 0.46 g. of the isomeric 1-(p-methoxyphenyl)-1,4-cyclohexanediol, melting at 108.5° to 110° C.

Anal. Calcd. for $C_{13}H_{18}O_3$: C, 70.24; H, 8.16. Found: C, 70.30; H, 8.92.

Example 2: cis and trans 1-(p-fluorophenyl)-1,4-cyclohexanediol

A solution of 5.7 g. of 4-hydroxycyclohexanone in 60 ml. of tetrahydrofuran is added to 0.1 mole of p-fluorophenylmagnesium bromide in 170 ml. of tetrahydrofuran. Following 17 hours of standing at room temperature 50 ml. of ammonium chloride is added. The organic layer is washed with water and brine and taken to dryness. The residue is chromatographed over 500 ml. of Florisil. Elution with 5% acetone:Skellysolve B gives 0.65 g. of ddhydrated product, melting at 62° to 70° C. Elution with 20% acetone:Skellysolve B gives a series of crystalline fractions which are combined, based on thin layer chromatography (TLC), to form two fractions. The first material is recrystallized from acetone:benzene to give 0.94 g. of 1-(p-fluorophenyl)-1,4-cyclohexanediol, melting at 113° to 115° C.

Anal. Calcd. for $C_{12}H_{15}FO_2$: C, 68.55; H, 7.19. Found: C, 68.58; H, 7.38.

The more polar material is recrystallized from ethyl acetate to give 1.5 g. of isomeric 1-(p-fluorophenyl)-1,4-cyclohexanediol, m.p. 175° to 177° C.

Anal. Calcd. for $C_{12}H_{15}FO_2$: C, 68.55; H, 7.19. Found: C, 68.04; H, 7.68.

Example 3: 4-(p-fluorophenyl)-4-hydroxycyclohexanone

The cis and trans 1-(p-fluorophenyl)-1,4-cyclohexanediols obtained in Example 2 are dissolved together in acetone and cooled in an ice bath. Over the course of between about five and ten minutes, 17 ml. of Jones reagent [chromium trioxide-sulfuric acid, prepared as in J. Chem. Soc. 39 (1946)] is added. The solvent is removed under vacuum and the residue dissolved in water and ether. The organic layer is washed with water and brine and taken to dryness. The residue is chromatographed over 500 ml. of Florisil. Elution is carried out with 2 l. of 5% acetone-Skellysolve B, 1 l. of 10% acetone:Skellysolve B and then 20% acetone: Skellysolve B to give 4-(p-fluorophenyl)-4-hydroxycyclohexanone, melting at 115° to 117° C.

Anal. Calcd. for $C_{12}H_{13}FO_2$: C, 69.21; H, 6.29. Found: C, 69.50; H, 6.76.

Example 4: 4-(p-methylphenyl)-4-hydroxycyclohexanone

Following the procedure of Example 3 but substituting cis and trans 1-(p-methylphenyl)-1,4-cyclohexanediol as starting material, yields 4-(p-methylphenyl)-4-hydroxycyclohexanone, which on recrystallization from cyclohexane has a melting point of 109° to 111° C.

Anal. Calcd. for $C_{13}H_{16}O_2$: C, 76.44; H, 7.90. Found: C, 77.04; H, 8.16.

Example 5: 4-(p-chlorophenyl)-4-hydroxycyclohexanone

Following the procedure of Example 3 but substituting cis and trans 1-(p-chlorophenyl)-1,4-cyclohexanediol as starting material, yields 4-(p-chlorophenyl)-4-hydroxycyclohexanone, which on recrystallization from acetone:cyclohexane has a melting point of 137.5° to 139° C.

Anal. Calcd. for $C_{12}H_{13}ClO_2$: C, 64.14; H, 5.83. Found: C, 64.13; H, 6.02.

Example 6: 4-(p-trifluoromethylphenyl)-4-hydroxycyclohexanone

Following the procedure of Example 3 but substituting cis and trans 1-(p-trifluoromethylphenyl)-1,4-cyclohexanediol as starting material, yields 4-(p-trifluoromethylphenyl)-4-hydroxycyclohexanone, which on recrystallization from cyclohexane melts at 156° to 162° C.

Anal. Calcd. for $C_{13}H_{13}F_3O$: C, 60.63; H, 5.76. Found: C, 60.46; H, 5.07.

Example 7: 4-(p-fluorophenyl)-3-cyclohexen-1-one

To 17 ml. of well stirred trifluoroacetic acid, 0.16 g. of 4-(p-fluorophenyl)-4-hydroxycyclohexanone (obtained as in Example 3) is added. At the end of about 5 minutes the mixture is poured into an excess of aqueous sodium bicarbonate solution. The solid material is collected on a filter and recrystallized from petroleum ether to give a 96% yield of 4-(p-fluorophenyl)-3-cyclohexen-1-one melting at 44.5° to 46.5° C.

Example 8: 4-(p-methylphenyl)-3-cyclohexen-1-one

Following the procedure of Example 7 but substituting 4-(p-methylphenyl)-4-hydroxycyclohexanone (obtained as in Example 4) as starting material, gives an 80% yield of 4-(p-methylphenyl)-3-cyclohexen-1-one having a melting point of 72° to 74° C. on recrystallization from petroleum ether.

Example 9: 4-(p-chlorophenyl)-3-cyclohexen-1-one

Following the procedure of Example 7 but substituting 4-(p-chlorophenyl)-4-hydroxycyclohexanone (obtained as in Example 5) as starting material, gives a 96% yield of 4-(p-chlorophenyl)-3-cyclohexen-1-one, melting at 59° to 62° C. on recrystallization from petroleum ether.

Example 10: 4-(p-trifluoromethylphenyl)-3-cyclohexen-1-one

Following the procedure of Example 7 but substituting 4-(p-trifluoromethylphenyl)-4-hydroxycyclohexanone (obtained as in Example 6) as starting material, gives an 86% yield of oily 4-(p-trifluoromethylphenyl)-3-cyclohexen-1-one.

Example 11: 4-(p-fluorophenyl)-3-cyclohexen-1-ol

A solution of 0.065 mole of 4-(p-fluorophenyl)-3-cyclohexen-1-one (obtained as in Example 7) and 6 g. of sodium borohydride in 130 ml. of ethanol is stirred at room temperature for about 5 hours. The bulk of the solvent is removed on a rotary evaporator and the residue diluted with water. The precipitated solid is collected on a filter and recrystallized from Skellysolve B to give a 96% yield of 4-(p-fluorophenyl)-3-cyclohexen-1-ol having a melting point of 73° to 74.5° C.

Anal. Calcd. for $C_{12}H_{13}FO$: C, 74.98; H, 6.82. Found: C, 75.05; H, 7.02.

Example 12: 4-(p-methylphenyl)-3-cyclohexen-1-ol

Following the procedure of Example 11 but substituting 4-(p-methylphenyl)-3-cyclohexen-1-one (obtained as in Example 8) as starting material, gives a 72% yield of 4-(p-methylphenyl)-3-cyclohexen-1-ol melting at 96.5° to 97.5° C. on recrystallization from Skellysolve B.

Anal. Calcd. for $C_{13}H_{16}O$: C, 82.93; H, 8.57. Found: C, 82.97; H, 8.44.

Example 13: 4-(p-chlorophenyl)-3-cyclohexen-1-ol

Following the procedure of Example 11 but substituting 4-(p-chlorophenyl)-3-cyclohexen-1one (obtained as in Example 9) as starting material, gives a 62% yield of 4-(p-chlorophenyl)-3-cyclohexen-1-ol melting at 108° to 111.5° C. on recrystallization from Skellysolve B.

Anal. Calcd. for $C_{12}H_{13}ClO$: C, 69.06; H, 6.28. Found: C, 68.80; H, 6.66.

Example 14: 4-(p-trifluoromethylphenyl)-3-cyclohexen-1-ol

Following the procedure of Example 11 but substituting 4-(p-trifluoromethylphenyl)-3-cyclohexen-1-one (obtained as in Example 10) as starting material, gives a 58% yield of 4-(p-trifluoromethylphenyl)-3-cyclohexen-1-ol melting at 103.5° to 105.5° C. on recrystallization from Skellysolve B.

Anal. Calcd. for $C_{13}H_{13}F_3O$: C, 64.46; H, 5.41. Found: C, 64.32; H, 5.73.

Example 15: cis and trans 4-(p-fluorophenyl)cyclohexanol

A mixture of 11.42 g. of 4-(p-fluorophenyl)-3-cyclohexen-1-ol (obtained as in Example 11) and 0.1 g. of 10% palladium on charcoal in 200 ml. of ethyl acetate is shaken under hydrogen until 1 equivalent of the gas is taken up, i.e., about 10 minutes. The catalyst is collected on a filter and the filtrate evaporated to dryness. The residual oily solid is chromatographed on 1 l. of Florisil and eluted with 8 l. of 4% acetone:Skellysolve B. The crystalline fractions are combined on the basis of TLC to give first the crude cis compound followed by the trans compound. The former was recrystallized from petroleum ether (on cooling in a freezer) to give 5.52 g. of cis 4-(p-fluorophenyl)cyclohexanol, having a melting point of 40° to 43° C.

Anal. Calcd. for $C_{12}H_{15}FO$: C, 74.19; H, 7.79. Found: C, 74.70; H, 8.08.

The trans compound obtained above is recrystallized from ether:Skellysolve B to give 3.5 g. of trans 4-(p-fluorophenyl)cyclohexanol melting at 120.5° to 123.5° C.

Anal. Calcd. for $C_{12}H_{15}FO$: C, 74.19; H, 7.79. Found: C, 74.18; H, 7.88.

Following the procedure of Example 15 but substituting other starting materials for 4-(p-fluorophenyl)-3-cyclohexen-1-ol, such as
1. 4-(p-methylphenyl)-3-cyclohexen-1-ol,
2. 4-(p-chlorophenyl)-3-cyclohexen-1-ol,
3. 4-(p-trifluoromethylphenyl)-3-cyclohexen-1-ol,
4. 4-(o-ethylphenyl)-3-cyclohexen-1-ol,
5. 4-(m-bromophenyl)-3-cyclohexen-1-ol,
6. 4-(p-propoxyphenyl)-3-cyclohexen-1-ol, etc., yields, respectively,
1. cis and trans 4-(p-methylphenyl)cyclohexanol,
2. cis and trans 4-(p-chlorophenyl)cyclohexanol,
3. cis and trans 4-(p-trifluoromethylphenyl)cyclohexanol,
4. cis and trans 4-(o-ethylphenyl)cyclohexanol,
5. cis and trans 4-(m-bromophenyl)cyclohexanol,
6. cis and trans 4-(p-propoxyphenyl)cyclohexanol, etc.

Example 16: cis 4-(p-fluorophenyl)cyclohexanol methanesulfonate

To an ice-cooled solution of 5.52 g. of cis 4-(p-fluorophenyl)cyclohexanol (obtained as in Example 15) in 40 ml. of pyridine, 5 ml. of methanesulfonyl chloride is added. Following about 6 hours of standing in the cold, the mixture is poured into water. The precipitated solid is collected on a filter and then recrystallized twice from aqueous methanol to yield 6.65 g. of cis 4-(p-fluorophenyl)cyclohexanol with a melting point of 98° to 100° C.

Anal. Calcd. for $C_{13}H_{17}FO_3S$: C, 57.33; H, 6.29. Found: C, 56.79; H, 6.57.

Following the procedure of Example 16 but substituting another organic (alkyl or aryl) sulfonyl halide for methanesulfonyl chloride such as: methanesulfonyl bromide, methanesulfonyl fluoride, ethanesulfonyl chloride, ethanesulfonyl fluoride, propanesulfonyl chloride, benzenesulfonyl bromide, benzenesulfonyl chloride, benzenesulfonyl fluoride, benzenesulfonyl iodide, p-toluenesulfonyl chloride, p-toluenesulfonyl bromide, p-toluenesulfonyl iodide, α-naphthalenesulfonyl chloride, α-naphthalenesulfonyl fluoride, α-naphthalene bromide, and the like, yields the corresponding cis 4(p-fluorophenyl)cyclohexanol organic (alkyl) or aryl) sulfonate.

Following the procedure of Example 16 but substituting other starting materials for cis 4-(p-fluorophenyl)cyclohexanol, such as
1. cis 4-(o-propylphenyl)cyclohexanol,
2. cis 4-(m-bromophenyl)cyclohexanol,
3. cis 4-(p-butoxyphenyl)cyclohexanol,
4. cis 4-(p-trifluoromethylphenyl)cyclohexanol, etc., yields, respectively,
1. cis 4-(o-propylphenyl)cyclohexanol methanesulfonate,
2. cis 4-(m-bromophenyl)cyclohexanol methanesulfonate,
3. cis 4-(p-butoxyphenyl)cyclohexanol methanesulfonate,
4. cis 4-(p-trifluoromethyl)cyclohexanol methanesulfonate, etc.

Following the procedure of Example 16 and the paragraphs thereafter but substituting other starting materials and other organic sulfonyl halides, such as
1. cis 4-(o-butylphenyl)cyclohexanol and ethanesulfonyl chloride,
2. cis 4-(m-chlorophenyl)cyclohexanol and benzenesulfonyl bromide,
3. cis 4-(p-ethoxyphenyl)cyclohexanol and toluenesulfonyl chloride,
4. cis 4-(o-trifluoromethylphenyl)cyclohexanol and α-naphthalenesulfonyl iodide, etc., yields, respectively,
1. cis 4-(o-butylphenyl)cyclohexanol ethanesulfonate,
2. cis 4-(m-chlorophenyl)cyclohexanol benzenesulfonate,
3. cis 4-(p-ethoxyphenyl)cyclohexanol toluenesulfonate,
4. cis 4-(o-trifluoromethylphenyl)cyclohexanol α-naphthalenesulfonate, etc.

Example 17: trans 4-(p-fluorophenyl)cyclohexanol methanesulfonate

To an ice-cooled solution of 3.5 g. of trans 4-(p-fluorophenyl)cyclohexanol (obtained as in Example 15) in 30 ml. of pyridine, 3.5 ml. of methanesulfonyl chloride is added. Following about 6 hours of standing in the cold, the mixture is poured into water. The solid that precipitates is recrystallized twice from aqueous methanol to give 4.22 g. of trans 4-(p-fluorophenyl)cyclohexanol methanesulfonate melting at 90° to 92.5° C., and having a mixed melting point with its cis counterpart of 72° to 90° C.

Anal. Calcd. for $C_{13}H_{17}FO_3S$: C, 57.33; H, 6.29. Found: C, 57.03; H, 6.48.

Following the procedure of Example 17 but substituting other trans 4-(substituted phenyl)cyclohexanols and other organic sulfonyl halides, such as
1. trans 4-(o-chlorophenyl)cyclohexanol and propanesulfonyl bromide,
2. trans 4-(m-ethoxyphenyl)cyclohexanol and p-toluenesulfonyl chloride,
3. trans 4-(p-butylphenyl)cyclohexanol and β-naphthalenesulfonyl fluoride, etc., yields, respectively,
1. trans 4-(o-chlorophenyl)cyclohexanol propanesulfonate,
2. trans 4-(m-ethoxyphenyl)cyclohexanol p-toluenesulfonate,
3. trans 4-(p-butylphenyl)cyclohexanol β-naphthalenesulfonate, etc.

Example 18: trans 4-(p-fluorophenyl)cyclohexan-1-ylazide

A mixture of 6.65 g. of cis 4-(p-fluorophenyl)cyclohexanol methanesulfonate (obtained as in Example 16) and an equal weight of sodium azide in 65 ml. of dimethylformamide is stirred in an oil bath at about 90° to 95° C. for about 12 hours. The mixture is taken to dryness on a rotary evaporator at 2 mm. of mercury and the residue dissolved in water and benzene. The organic layer is washed with water and brine to give 4.84 g. of trans 4-(p-fluorophenyl)cyclohexan-1-ylazide.

Following the procedure of Example 18 but substituting other cis 4-(substituted phenyl)cyclohexanol organic sulfonates, such as
1. cis 4-(o-bromophenyl)cyclohexanol ethanesulfonate,
2. cis 4-(m-propoxyphenyl)cyclohexanol benzenesulfonate,
3. cis 4-(p-trifluoromethylphenyl)-α-naphthalenesulfonate, etc., yields, respectively,
1. trans 4-(o-bromophenyl)cyclohexan-1-ylazide,
2. trans 4-(m-propoxyphenyl)cyclohexan-1-ylazide,
3. trans 4-(p-trifluoromethylphenyl)cyclohexan-1-ylazide, etc.

Example 19: cis 4-(p-fluorophenyl)cyclohexan-1-ylazide

A mixture of 4.22 g. of trans 4-(p-fluorophenyl)cyclohexanol methanesulfonate (obtained as in Example 17) and an equal weight of sodium azide in 45 ml. of dimethylformamide is heated at about 95° C. for about 12 hours. The mixture is taken to dryness on a rotary evaporator and the residue dissolved in water and benzene. The organic layer is washed with water and brine to yield cis 4-(p-fluorophenyl)cyclohexan-1-ylazide.

Following the procedure of Example 19 but substituting other trans 4-(substituted phenyl)cyclohexanol organic sulfonates, such as
1. trans 4-(o-chlorophenyl)cyclohexanol propanesulfonate,
2. trans 4-(m-butylphenyl)cyclohexanol toluenesulfonate,
3. trans 4-(p-ethoxyphenyl)cyclohexanol β-naphthalenesulfonate, etc., yields, respectively,
1. cis 4-(o-chlorophenyl)cyclohexan-1-ylazide,
2. cis 4-(m-butylphenyl)cyclohexan-1-ylazide,
3. cis 4-(p-ethoxyphenyl)cyclohexan-1-ylazide, etc.

Example 20: trans 4-(p-fluorophenyl)cyclohexylamine hydrochloride (I)

A solution of the trans 4-(p-fluorophenyl)cyclohexan-1-ylazide obtained in Example 18 in 75 ml. of tetrahydrofuran is added to a well stirred suspension of 2.4 g. of lithium aluminum hydride in 25 ml. of tetrahydrofuran. Following about 1 hour of stirring at room temperaturre and about 2 hours of heating at reflux, the mixture is cooled in ice. There is added successively, 2.4 ml. of water, 2.4 ml. of 15% aqueous sodium hydroxide solution and 6 ml. of water. The precipitated solid is collected on a filter and the filtrate evaporated to dryness. The residual solid is dissolved in ether and treated with 3.6N ethereal hydrochloric acid. The solid is recrystallized twice from methanol:ethyl acetate to give 3.05 g. of trans 4-(p-fluorophenyl)cyclohexylamine hydrochloride (I) melting above 330° C.

Anal. Calcd. for $C_{12}H_{17}ClFN$: C, 62.73; H, 7.46; Cl, 15.44. Found: C, 62.70; H, 7.76; Cl, 15.64.

Following the procedure of Example 20 but substituting other trans 4-(substituted phenyl)cyclohexan-1-ylazides such as
1. trans 4-(m-fluorophenyl)cyclohexan-1-ylazide,
2. trans 4-(p-chlorophenyl)cyclohexan-1-ylazide,
3. trans 4-(o-methylphenyl)cyclohexan-1-ylazide,
4. trans 4-(m-methylphenyl)cyclohexan-1-ylazide,
5. trans 4-(p-methylphenyl)cyclohexan-1-ylazide,
6. trans 4-(o-methoxyphenyl)cyclohexan-1-ylazide,
7. trans 4-(m-methoxyphenyl)cyclohexan-1-ylazide,
8. trans 4-(p-methoxyphenyl)cyclohexan-1-ylazide,
9. trans 4-(m-trifluoromethylphenyl)cyclohexan-1-ylazide,
10. trans 4-(p-trifluoromethylphenyl)cyclohexan-1-ylazide, etc., yields, respectively,
1. trans 4-(m-fluorophenyl)cyclohexylamine hydrochloride (I),
2. trans 4-(p-chlorophenyl)cyclohexylamine hydrochloride (I),
3. trans 4-(o-methylphenyl)cyclohexylamine hydrochloride (I),
4. trans 4-(m-methylphenyl)cyclohexylamine hydrochloride (I),
5. trans 4-(p-methylphenyl)cyclohexylamine hydrochloride (I),
6. trans 4-(o-methoxyphenyl)cyclohexylamine hydrochloride (I),
7. trans 4-(m-methoxyphenyl)cyclohexylamine hydrochloride (I),
8. trans 4-(p-methoxyphenyl)cyclohexylamine hydrochloride (I), 9. trans 4-(m-trifluoromethylphenyl)cyclohexylamine hydrochloride (I),
10. trans 4-(p-trifluoromethylphenyl)cyclohexylamine hydrochloride (I), etc.

Example 21: cis 4-(p-fluorophenyl)cyclohexylamine hydrochloride (I)

Following procedure of Example 20 but substituting cis 4-(p-fluorophenyl)cyclohexan-1-ylazide obtained in Example 19 as starting material, yields cis 4-(p-fluorophenyl)cyclohexylamine hydrochloride (I), melting at 237° to 238.5° C.

Anal. Calcd. for $C_{12}H_{17}ClFN$: C, 62.73; H, 7.46; Cl, 15.44. Found: C, 62.38; H, 7.56; Cl, 15.43.

Following the procedure of Example 21 but substituting other cis 4-(substituted phenyl)cyclohexan-1-ylazides, such as.
1. cis 4-(m-fluorophenyl)cyclohexan-1-ylazide,
2. cis 4-(p-chloromethylphenyl)cyclohexan-1-ylazide,
3. cis 4-(o-methylphenyl)cyclohexan-1-ylazide,
4. cis 4-(m-methylphenyl)cyclohexan-1-ylazide,
5. cis 4-(p-methylphenyl)cyclohexan-1-ylazide,
6. cis 4-(o-methoxyphenyl)cyclohexan-1-ylazide,
7. cis 4-(m-methoxyphenyl)cyclohexan-1-ylazide,
8. cis 4-(p-methoxyphenyl)cyclohexan-1-ylazide,
9. cis 4-(m-trifluoromethylphenyl)cyclohexan-1-ylazide,
10. cis 4-(p-trifluoromethylphenyl)cyclohexan-1-ylazide, etc., yields, respectively,
1. cis 4-(m-fluorophenyl)cyclohexylamine hydrochloride (I),
2. cis 4-(p-chloromethylphenyl)cyclohexylamine hydrochloride (I),
3. cis 4-(o-methylphenyl)cyclohexylamine hydrochloride (I),
4. cis 4-(m-methylphenyl)cyclohexylamine hydrochloride (I),
5. cis 4-(p-methylphenyl)cyclohexylamine hydrochloride (I),
6. cis 4-(o-methoxyphenyl)cyclohexylamine hydrochloride (I),
7. cis 4-(m-methoxyphenyl)cyclohexylamine hydrochloride (I),
8. cis 4-(p-methoxyphenyl)cyclohexylamine hydrochloride (I),
9. cis 4-(m-trifluoromethylphenyl)cyclohexylamine hydrochloride (I),
10. cis 4-(p-trifluoromethylphenyl)cyclohexylamine hydrochloride (I), etc.

Following the procedures of Examples 20 and 21 and the paragraphs thereafter, but substituting for hydrochloric acid, another acid such as hydrobromic, sulfuric, phosphoric, nitric, benzoic, naphthoic, salicylic, tartaic, nicotinic, cyclohexanesulfamic, hexynoic, lactic, palmitic, glutaric, acetic, propionic, phenylbutyric acid, and the like, yields a corresponding acid addition salt of a cis or trans 4-(substituted phenyl)cyclohexylamine (I), e.g., cis 4-(o-bromophenyl)cyclohexylamine hydrobromide (I), trans 4-(m-ethoxyphenyl)cyclohexylamine nitrate (I), cis 4-(p-propylphenyl)cyclohexylamine benzoate (I), cis 4-(o-chlorophenyl)cyclohexylamine salicylate (I), trans 4-(m-trifluoromethyl)phenyl)cyclohexylamine lactate (I), cis 4-(p-butoxyphenyl)cyclohexylamine acetate (I), etc.

Example 22: trans 1-[4-(p-fluorophenyl)cyclohexyl]piperidine (I)

To a solution of 2 g. of trans 4-(p-fluorophenyl)cyclohexylamine hydrochloride (I) (prepared as in Example 20) in 35 ml. of ethanol, 2.2 ml. of 4.18N methanolic sodium methoxide is added. Following about 1 hour of stirring, 2.78 g. of 1,5-diiodopentane and 2.1 g. of potassium carbonate is added. The mixture is then heated at reflux for about 16 hours. The bulk of the solvent is removed under vacuum and the residue dissolved in ether and water. The organic layer is washed with water and brine and taken to dryness. The residual solid is crystallized from aqueous methanol to give 1.6 g. of trans 1-[4-(p-fluorophenyl)cyclohexyl]piperidine (I), melting at 76° to 79° C.

Anal. Calcd. for $C_{17}H_{24}FN$: C, 78.12; H, 9.26. Found: C, 77.95; H, 9.64.

The thus produced free base on being dissolved in ether and treated with 3.6N ethereal hydrogen chloride, gives a solid precipitate, which on recrystallization (e.g., from methanol:ethyl acetate) yields trans 1-[4-(p-fluorophenyl)cyclohexyl]piperidine hydrochloride (I).

Following the procedure of Example 22 and the paragraph thereafter, but substituting another starting material, such as
1. trans 4-(o-bromophenyl)cyclohexylamine hydrochloride (I),
2. trans 4-(m-butoxyphenyl)cyclohexylamine hydrochloride (I),
3. trans 4-(p-propylphenyl)cyclohexylamine hydrochloride (I), etc., yields, respectively,
1. trans 1-[4-(o-bromophenyl)cyclohexyl]piperidine (I),
2. trans 1-[4-(m-butoxyphenyl)cyclohexyl]piperidine (I),
3. trans 1-[4-(p-propylphenyl)cyclohexyl]piperidine (I), etc., or the hydrochlorides thereof.

Example 23: cis 1-[4-(p-fluorophenyl)cyclohexyl]piperidine hydrochloride (I)

To a solution of 2 g. of cis 4-(p-fluorophenyl)cyclohexylamine hydrochloride (I) (prepared as in Example 20) in 35 ml. of ethanol, 2.2 ml. of 4.18N methanolic sodium methoxide is added. The mixture is stirred for about 1 hour and 2.78 g. of 1,5-diiodopentane and 2.1 g. of potassium carbonate is then added. The mixture is then heated at reflux for about 16 hours. The bulk of the solvent is removed under vacuum and the residue dissolved in ether and water. The organic layer is washed with water and brine and evaporated to dryness. The residue is dissolved in ether and treated with 3.6N ethereal hydrogen chloride. The precipitated solid is recrystallized twice from methanol:ethyl acetate to yield 1.62 g. of cis 1-[4-(p-fluorophenyl)cyclohexyl]piperidine hydrochloride (I), having a melting point of 229° to 231° C.

Anal. Calcd. for $C_{17}H_{25}ClFN$: C, 68.55; H, 8.96. Found: C, 68.17; H, 8.52.

Following the procedure of Example 23 but substituting another starting material, such as
1. cis 4-(o-chlorophenyl)cyclohexylamine hydrochloride (I),
2. cis 4-(m-propoxyphenyl)cyclohexylamine hydrochloride (I), etc., yields, respectively,
1. cis 1-[4-(o-chlorophenyl)cyclohexyl]piperidine hydrochloride (I),
2. cis 1-[4-(m-propoxyphenyl)cyclohexyl]piperidine hydrochloride (I), etc.

Example 24: trans 1-[4-(p-fluorophenyl)cyclohexyl]pyrrolidine (I)

To a suspension of 2 g. of trans 4-(p-fluorophenyl)cyclohexylamine hydrochloride (I) (prepared as in Example 20) in 35 ml. of methanol, 2.15 ml. of 4.18N methanolic sodium methoxide is added. Following about 1 hour of stirring, 2.5 g. of potassium carbonate and 1.95 g. of 1,4-dibromobutane is added. The mixture is heated at reflux for about 17 hours and taken to dryness. The residue is dissolved in water and ether. The organic layer is washed with water and brine and taken to dryness. The residual solid is recrystallized twice from petroleum ether by cooling in a freezer to give trans 1-[4-(p-fluorophenyl)cyclohexyl]pyrrolidine (I).

Dissolving the thus produced compound in ether and treating it with 3.6N ethereal hydrogen chloride yields trans 1-[4-(p-fluorphenyl)cyclohexyl]pyrrolidine hydrochloride (I).

Following the procedure of Example 24 but substituting other starting materials, such as
1. trans 4-(o-bromophenyl)cyclohexylamine hydrochloride (I),
2. trans 4-(m-methoxyphenyl)cyclohexylamine hydrochloride (I), etc., yields, respectively,
1. trans 1-[4-(o-bromophenyl)cyclohexyl]pyrrolidine (I),
2. trans 1-[4-(m-methoxyphenyl)cyclohexyl]pyrrolidine (I), etc.

Example 25: cis 1-[4-(p-fluorophenyl)cyclohexyl]pyrrolidine (I)

Following the procedure of Example 24 but substituting starting materials such as
1. cis 4-(p-fluorophenyl)cyclohexylamine hydrochloride (I),
2. cis 4-(o-butoxyphenyl)cyclohexylamine hydrochloride (I),
3. cis 4-(m-propylphenyl)cyclohexylamine hydrochloride (I), etc.

yields, respectively,
1. cis 1-[4-(p-fluorophenyl)cyclohexyl]pyrrolidine (I),
2. cis 1-[4-(o-butoxyphenyl)cyclohexyl]pyrrolidine (I),
3. cis 1-[4-(m-propylphenyl)cyclohexyl]pyrrolidine (I), etc.

Example 26: cis 1-[4-(p-fluorophenyl)cyclohexyl]hexamethylenimine hydrochloride (I)

Following the procedure of Example 23 but substituting 1,6-diiodohexane for 1,5-diiodopentane yields cis 1-[4-(p-fluorophenyl)cyclohexyl]hexamethylenimine hydrochloride (I).

Similarly, employing other dihaloalkanes with appropriate modifications of the procedures described in Examples 22 through 26, yields representative cis 1-[4-(substituted phenyl)cyclohexyl]unsubstituted and monosubstituted piperidines, pyrrolidines, hexamethylenimines, morpholines, and piperazines, such as cis 1-[4-(o-ethylphenyl)cyclohexyl]-3-ethylpiperidine hydrochloride (I), cis 1-[4-(m-chlorophenyl)cyclohexyl]-3-propylpyrrolidine hydrochloride (I), cis 1-[4-(p-butoxyphenyl)cyclohexyl]-3-ethoxyhexamethylenimine hydrochloride (I), cis 1-[4-(o-trifluoromethylphenyl)cyclohexyl]morpholine hydrochloride (I), cis 1-[4-(o-fluorophenyl)cyclohexyl]-2-methylmorpholine hydrochloride (I), cis 1-[4-(m-butylphenyl)cyclohexyl]piperazine hydrochloride (I), and the like.

Example 27: trans 1-[4-(p-fluorophenyl)cyclohexyl]hexamethylenimine hydrochloride (I)

Following the procedure of Example 22 but substituting 1,6-diiodohexane for 1,5-diiodopentane yields trans 1-[4-(p-fluorophenyl)cyclohexyl]hexamethylenimine hydrochloride (I).

Following the procedure set forth in the paragraph following Example 26 yields representative trans 1-(4-(substituted phenyl)cyclohexyl]piperidines, pyrrolidines, hexamethylenimines, morpholines, and piperazines such as trans 1-[4-(o-butylphenyl)cyclohexyl]-3-ethylpiperidine hydrochloride (I), trans 1-[4-(m-propoxyphenyl)cyclohexyl]-3-butoxyhexamethylenimine hydrochloride (I), trans 1-[4-(p-chlorophenyl)cyclohexyl]-2-ethylmorpholine hydrochloride (I), trans 1-[4-(o-propylphenyl)cyclohexyl]piperazine hydrochloride (I), and the like.

Example 28: trans 1-[4-(p-fluorophenyl)cyclohexyl]-3-methylurea (I)

A suspension of 1 g. of trans 4-(p-fluorophenyl)cyclohexylamine hydrochloride (I) (prepared as in Example 20) in ether and 1N sodium hydroxide solution is stirred until no solid remains. The organic layer is separated and evaporated to dryness. To a solution of the thus obtained free base in 20 ml. of tetrahydrofuran, 1 ml. of methylisocyanate is added. After about 3 hours, the resulting suspension is taken to dryness. The residue is recrystallized twice from acetonitrile to give trans 1-[4-(p-fluorophenyl)cyclohexyl]-3-methylurea (I).

Following the procedure of Example 28 but substituting for methylisocyanate, other alkylisocyanates such as
1. ethylisocyanate,
2. isobutylisocyanate, etc., yields, respectively,
1. trans 1-[4-(p-fluorophenyl)cyclohexyl]-3-ethylurea (I),
2. trans 1-[4-(p-fluorophenyl)cyclohexyl]-3-isobutylurea (I), etc.

Following the procedure of the immediately preceding paragraph and Example 38 but substituting other starting materials and alkylisocyanates, such as 1. trans 4-(o-ethylphenyl)cyclohexylamine hydrochloride (I) and isopropylisocyanate, 2. trans 4- (m-trifluoromethylphenyl)cyclohexylamine hydrochloride (I) and butylisocyanate, etc., yields, respectively,
1. trans 1-[4-(o-ethylphenyl)cyclohexyl]-3-isopropylurea (I),
2. trans 1-[4-(m-trifluoromethylphenyl)cyclohexyl]-3-butylurea (I), etc.

Example 29: cis 1-[4-(p-fluorophenyl)cyclohexyl]-3-methylurea (I)

Following the procedure of Example 28 but substituting cis 4-(p-fluorophenyl)cyclohexylamine hydrochloride (I) (prepared as in Example 21) as starting material, yields cis 1-[4-(p-fluorophenyl)cyclohexyl]-3-methylurea (I).

Following the procedure of Example 29 and employing those set forth in the two paragraphs following Example 28 yields compounds such as cis 1-[4-(o-chlorophenyl)cyclohexyl]-3-ethylurea (I), cis 1-[4-(m-ethoxyphenyl)cyclohexyl]-3-propylurea (I), etc.

Example 30: trans N-[4-(p-fluorophenyl)cyclohexyl]-methanseulfonamide (I)

A suspension of 1 g. of trans 4-(p-fluorophenyl)cyclohexylamine hydrochloride (I) (prepared as in Example 20) in ether and 1N sodium hydroxide solution is stirred until no solid remains. The organic layer is separated and taken to dryness. To a solution of the thus obtained free base and 0.65 ml. of triethylamine in 25 ml. of tetrahydrofuran, 0.55 ml. of methanesulfonyl chloride is added. At the end of about 3.5 hours the mixture is diluted with ether and washed successively with water, 2.5N hydrochloric acid, water and sodium bicarbonate solution. The organic layer is taken to dryness and the remaining solid recrystallized from acetone:Skellysolve B to give trans N-[4-(p-fluorophenyl)cyclohexyl]methanesulfonamide (I).

Following the procedure of Example 30 but substituting for trans 4-(p-fluorophenyl)cyclohexylamine hydrochloride (I) and methanesulfonyl chloride, other starting materials and other organic sulfonyl halides, such as
1. trans 4-(o-propylphenyl)cyclohexylamine hydrochloride (I) and methanesulfonyl chloride,
2. trans 4-(m-butoxyphenyl)cyclohexylamine hydrochloride (I) and p-toluenesulfonyl bromide, etc., yields, respectively,
1. trans N-[4-(o-propylphenyl)cyclohexyl]ethanesulfonamide (I),
2. trans N-[4-(p-fluorophenyl)cyclohexyl]-p-toluenesulfonamide (I), etc.

Example 31: cis N-[4-(p-fluorophenyl)cyclohexyl]methanesulfonamide (I)

Following the procedure of Example 30 but substituting cis 4-(p-fluorophenyl)cyclohexylamine hydrochloride (I) (prepared as in Example 21) as starting material, yields cis N-[4-p-fluorophenyl)cyclohexyl]methanesulfonamide (I).

Following the procedure of Example 31 and the one set forth in the paragraph following Example 30, yields compounds such as cis N-[-4-(o-bromophenyl)cyclohexyl]propanesulfonamide (I), cis N-[4-(butoxyphenyl)cyclohexyl]-β-naphthalenesulfonamide (I), etc.

Example 32: trans N-[4-(p-fluorophenyl)cyclohexyl]-formamide (I)

A mixture of 2.21 g. of the free base form of trans 4-(p-fluorophenyl)cyclohexylamine (I) obtained by stirring an ether solution of its hydrochloride (2.86 g.), prepared as in Example 20, with 2.35 ml. of triethylamine) and 27 ml. of ethyl formate is heated at reflux for about 40 hours. The resulting solution is taken to dryness and the residue recrystallized from benzene to give trans N-[4-(p-fluorophehnyl(cyclohexyl[formamide (I), m.p. 139.5° to 142.5° C.

Anal. Calcd. for $C_{13}H_{16}FNO$: C, 70.56; H, 7.29. Found: C, 70.80; H, 7.63.

Following the procedure of Example 32 but substituting another starting material such as
1. trans 4-(o-methoxyphenyl)cyclohexylamine (I),
2. trans 4-(m-propylphenyl)cyclohexylamine (1), etc., yields, respectively,
1. trans N-[4-(o-methoxyphenyl)cyclohexyl]formamide (I),
2. trans N-[4-(m-propylphenyl)cyclohexyl]formamide (I), etc.

Example 33: cis N-[4-(p-fluorophehyl)cyclohexyl]formamide (I)

Following the procedure of Example 32 but substituting cis 4-(p-fluorophenhyl)cyclohexylamine (I) (obtained by stirring an ether solution of its hydrochloride, prepared as in Example 21, with triethylamine) as starting material, yields cis N-[4-(p-fluorophehyl)cyclohexyl]formamide (I), m.p. 121° to 124° C.

Anal. Calcd. for $C_{13}H_{16}FNO$: C, 70.56; H, 7.29. Found: C, 71.03; H, 7.49.

Following the procedure of Example 33 and the one set forth in the paragraph following Example 32, yields compounds such as cis N-[4-(o-bromophenyl)cyclohexyl]formamide (I), cis, N-[4-(m-butylphenyl)cyclohexyl]formamide (I), etc.

Example 34: trans N-methyl-[4-(p-fluorophenyl)cyclohexyl]-amine hydrochloride (I)

A solution of 2.26 g. of trans N-[4-(p-fluorophenyl)-cyclohexyl]formamide (I) (obtained as in Example 32) in 67 ml. of tetrahydrofuran is added to a well stirred suspension of 0.56 g. of lithium aluminum hydride in 11 ml. of tetrahydrofuran. After heating this mixture at reflux for about 4 hours it is cooled in ice. There is then added successively, 0.56 ml. of water, 0.56 ml. of 15% sodium hydroxide solution and 1.6 ml. of water. The solid that precipitates is removed by filtration and the filtrate evaporated to dryness. The residue is dissolved in ether and treated with a small excess of 3.6N ethereal hydrogen chloride. The solid that precipitates is recrystallized from methylene chloride:ethyl acetate to give trans N-methyl-[4(p-fluorophenyl)cyclohexyl]amine hydrochloride (I), m.p. 213° to 215° C.

Anal. Calcd. for $C_{13}H_{19}ClFN$: C, 64.05; H, 7.86; Cl, 14.55. Found: C, 64.79; H, 8.15; Cl, 14.51.

Following the procedure of Example 34 but substituting another starting material, such as
1. trans N-[4(o-propoxyphenyl)cyclohexyl]formamide (I),
2. trans N-[4-(m-trifluoromethylphenyl)cyclohexyl]-formamide (I), etc., yields, respectively,
1. trans N-methyl-[4-(o-propoxyphenyl)cyclohexyl]amine hydrochloride (I),
2. trans N-methyl-[4-(m-trifluoromethylphenyl)cyclohexyl]amine hydrochloride (I), etc.

Example 35: cis N-methyl-[4-(p-fluorophenyl)cyclohexyl]amine hydrochloride (I)

Following the procedure of Example 34 but substituting cis N-[4-(p-fluorophenyl)cyclohexyl]formamide (I) as starting material, yields cis N-methyl-[4-(p-fluorophenyl)cyclohexyl]amine hydrochloride (I), m.p. 239.5° to 240.5° C.

Anal. Calcd. for $C_{13}H_{19}ClFN$: C, 64.05; H, 7.86; Cl, 14.55. Found: C, 64.79; H, 7.98; Cl, 14.85.

Following the procedure of Example 35 and the one described in the paragraph following Example 34, yields compounds such as cis N-methyl-[4-(o-chlorophenyl)cyclohexyl]amine hydrochloride (I), cis N-methyl-[4-(m-propoxyphenyl)cyclohexyl]amine hydrochloride (I), cis N-methyl-[4-(p-trifluoromethylphenyl)cyclohexyl]amine hydrochloride (I), etc.

Example 36: trans N-methyl-4-(p-fluorophenyl)cyclohexyl-1-carbamic acid ethyl ester (I)

To an ice cooled solution of 3 g. of the free base form of trans N-methyl-[4-(p-fluorophenyl)cyclohexyl]amine (I) (obtained by stirring an ether solution of its hydrochloride, prepared as in Example 34, with N sodium hydroxide) and 2.15 ml. of triethylamine in 30 ml. of ether, 1.6 ml. of ethyl chloroformate is added dropwise. Following about 5 hours of standing in the cold, the mixture is diluted with ether and water. The organic layer is separated, washed with water and brine and taken to dryness. The residual solid is recrystallized from a small amount of petroleum ether (with cooling in a freezer) to give trans N-methyl-4-(p-fluorophenyl)cyclohexyl-1-carbamic acid ethyl ester (I).

Following the procedure of Example 36 but substituting another starting material and another alkyl haloformate, such as
1. trans N-methyl-[4-(o-trifluoromethylphenyl)cyclohexyl]amine (I) and methyl bromoformate,
2. trans N-methyl-[4-(m-butoxyphenyl)cyclohexyl]amine and propyl chloroformate, etc., yields, respectively,
1. trans N-methyl-4-[o-trifluoromethylphenyl)cyclohexyl-1-carbamic acid methyl ester (I),
2. trans N-methyl-4-(m-butoxyphenyl)cyclohexyl-1-carbamic acid propyl ester (I), etc.

Example 37: cis N-methyl-4-(p-fluoro-o-tolyl)cyclohexyl-1-carbamic acid ethyl ester (I)

Following the procedure of Example 36 but substituting the free base form of cis N-methyl-[4-(p-fluoro-o-tolyl)cyclohexyl]amine hydrochloride (I) (obtained as in Example 65) as starting material, yields cis N-methyl-4-(p-fluoro-o-tolyl)cyclohexyl-1-carbamic acid ethyl ester (I).

Following the procedure of Example 37 but substituting another starting material and another alkylhaloformate, such as cis N-methyl-[4-(o-chloro-p-ethyl)phenyl cyclohexyl]amine (I) and ethyl bromoformate, cis N-ethyl-[4-(m-bromo-p-propyl)phenyl cyclohexyl]amine (I) and propyl chloroformate and the like, yields, respectively, cis N-methyl-4-(o-chloro-p-ethyl)phenyl cyclohexyl-1-carbamic acid ethyl ester (I), cis N-methyl-4-(m-bromo-p-propyl)phenyl cyclohexyl-1-carbamic acid propyl ester (I).

Example 38: trans N,N-dimethyl-4-(p-fluorophenyl)cyclohexylamine hydrochloride (I)

A solution of 2.5 g. of trans N-methyl-4-(p-fluorophenyl)cyclohexyl-1-carbamic acid ethyl ester (I) )obtained as in Example 36) in 60 ml. of tetrahydrofuran is added to a well stirred suspension of 1 g. of lithium aluminum hydride in 10 ml. of tetrahydrofuran. Following about 4 hours of heating at reflux, the mixture is cooled in ice and treated successively with 1 ml. of water, 1 ml. of 15% sodium hydroxide solution and 3 ml. of water. The solid is removed by filtration and the filtrate taken to dryness. The oily amine is converted to the hydrochloride with 3.6 N ethereal hydrogen chloride. The solid is recrystallized twice from methylene chloride:ethyl acetate to give trans N,N-dimethyl-4-(p-fluorophenyl)cyclohexylamine hydrochloride (I).

Following the procedure of Example 38 but substituting another starting material, such as
1. trans N-methyl-4-(o-bromophenyl)cyclohexyl-1-carbamic acid ethyl ester (I),
2. trans N-methyl-4-(m-ethoxyphenyl)cyclohexyl-1-carbamic acid ethyl ester (I), etc., yields, respectively,
trans N,N-dimethyl-4-(o-bromophenyl)cyclohexylamine hydrochloride (I),
2. trans N,N-dimethyl-4-(m-ethoxyphenyl)cyclohexylamine hydrochloride (I), etc.

Example 39: cis N,N-dimethyl-4-(p-fluorophenyl)cyclohexylamine hydrochloride (I)

Following the procedure of Example 38 but substituting cis N-methyl-4-(p-fluorophenyl)cyclohexyl-1-carbamic acid ethyl ester (I) as starting material, yields cis N,N-dimethyl-4-(p-fluorophenyl)cyclohexylamine hydrochloride (I).

Following the procedure of Example 39 and the one described in the paragraph following Example 38, yields compounds such as cis N,N-dimethyl-4-(m-chlorophenyl)cyclohexylamine hydrochloride (I), cis N,N-dimethyl-4-(p-butylphenyl)cyclohexylamine hydrochloride (I), etc.

Example 40: trans 4'-fluoro-4-{[4-(p-fluorophenyl)cyclohexyl]-amino}butyrophenone hydrochloride (I)

To a suspension of 2 g. of trans 4-(p-fluorophenyl)cyclohexylamine hydrochloride (I) (prepared as in Example 20) in 30 ml. of dimethylformamide, 0.36 g. of 56% sodium hydride in mineral oil is added. Following about 25 minutes of stirring, there is added successively, 2.42 g. of potassium carbonate, 1.49 g. of potassium iodide and 2.18 g. of the 2,2-dimethyl-1,3-propanediol ketal of 4-chloro-4'-fluorobutyrophenone. The mixture is stirred in an oil bath at 90° for about 18 hours, allowed to cool and then dissolved in benzene and water. The organic layer is washed thoroughly with water and brine and then taken to dryness. The residue is dissolved in 80 ml. of methanol; 40 ml. of 2.5N hydrochloric acid is added, mixture stirred for about 1 hour and then concentrated under vacuum. The precipitated solid is collected on a filter. Two recrystallizations from methanol: 2.5N hydrochloric acid gives pure trans 4'-fluoro-4-{[ 4-(p-fluorophenyl)cyclohexyl-]amine}butyrophenone hydrochloride (I), m.p. 193° to 197° C.

Anal. Calcd. for $C_{22}H_{26}ClF_2NO$: C, 67.08; H, 6.65. Found: C, 67.23; H, 6.50.

Following the procedure of Example 40 but substituting an acid addition salt of another trans 4-(substituted phenyl)cyclohexylamine (I) as starting material and the 2,2-dimethyl-1,3-propanediol ketal of another ω-haloalkanaryl ketone, such as
1. trans 4-(o-chlorophenyl)cyclohexylamine hydrochloride (I) and the 2,2-dimethyl-1,3-propanediol ketal of 4'-bromo-4-chlorobutyrophenone, 2. trans 4-(m-propoxyphenyl)cyclohexylamine hydrochloride (I) and the 2,2-dimethyl-1,3-propanediol ketal of 4'-butoxy-4-chlorobutyrophenone,
3. trans 4-(p-ethylphenyl)cyclohexylamine hydrobromide (I) and the 2,2-diemthyl-1,3-propanediol ketal of 4-chloro-4'-ethoxybutyrophenone,
4. trans 4-(o-trifluoromethylphenyl)cyclohexylamine nitrate (I) and the 2,2-dimethyl-1,3-propanediol ketal of 4-chloro-2'-methylbutyrophenone,
5. trans 4-(m-butylphenyl)cyclohexylamine cyclohexanesulfamate (I) and the 2,2-dimethyl-1,3-propanediol ketal of 3',4-dichlorobutyrophenone,
6. trans 4-(p-brompohenyl)cyclohexylamine hydrochloroide (I) and the 2,2-dimethyl-1,3-propanediol ketal of 2,2'-dichloroacetophenone,
7. trans 4-(o-methoxyphenyl)cyclohexylamine hydrochloride (I) and the 2,2-dimethyl-1,3-propanediol ketal of 3-chloro-4'-methylpropiophenone,
8. trans 4-(m-trifluoromethylphenyl)cyclohexylamine hydrochloride (I) and the 2,2-dimethyl-1,3-propanediol ketal of 5-chloro-4'-methylvalerophenone,
9. trans 4-(p-methoxyphenyl)cyclohexylamine hydrochloride (I) and the 2,2-dimethyl-1,3-propanediol ketal of 4-chloro-4'-fluorobutyro-α-naphthone, etc., yields, respectively,
1. trans 4'-bromo-4-{[4-(o-chlorophenyl)cyclohexyl]amino}butyrophenone hydrochloride (I),
2. trans 4'-butoxy-4-{[4-(m-propoxyphenyl)cyclohexyl]amino}butyrophenone hydrochloride (I),
3. trans 4'-ethoxy-4{[4-(p-ethylphenyl)cyclohexyl]amino}butyrophenone hydrobromide (I),
4. trans 2'-methyl-4 {[4-(o-trifluoromethylphenyl)cyclohexyl]amino}butyrophenone nitrate (I),
5. trans 3'-chloro-4{[4-(m-butylphenyl)cyclohexyl]amino}butyrophenone cyclohexanesulfamate (I),
6. trans 2'-chloro-2-{[4-(p-bromophenyl)cyclohexyl]amino}acetophenone hydrochloride (I),
7. trans 4'-ethoxy-3-{[4-(o-methoxyphenyl)cyclohexyl]amino}propiophenone hydrochloride (I),
8. trans 4'-methyl-5-{[4-(m-trifluoromethylphenyl)cyclohexyl]amino}valerophenone hydrochloride (I),
9. trans 4'-fluoro-4-{[4-(p-methoxyphenyl)cyclohexyl]amino}butyro-α-naphthone hydrochloride (I), etc.

Example 41: cis
4'-fluoro-4-{[4-(p-fluorophenyl)cyclohexyl]amino}butryophenone hydrochloride (I)

Following the procedure of Example 40 but substituting cis 4-(p-fluorophenyl)cyclohexylamine hydrochloride (I) (prepared as in Example 21) as starting material, yields cis 4'-fluoro-4-{[4-(p-fluorophenyl)cyclohexyl]amino}butyrophenone hydrocloride (I), m.p. 192° to 194° C.

Anal. Calcd. for $C_{22}H_{26}ClF_2NO$: C, 67.08; H, 6.65; Cl, 9.00. Found: C, 66.86 H, 6.57; Cl, 8.96.

Following the procedure of Exammple 41 and the one set forth in the paragraph following Example 40, yields compounds such as cis 4'-bromo-4-{[4-(o-bromophenyl)cyclohexyl]amine}butyrophenone hydrochloride (I), cis 2'-methyl-4{[4-(m-trifluoromethylphenyl)cyclohexyl]amino}butyrophenone hydrobromide (I), cis 2'-chloro-3-{[4- (p-propoxyphenyl)cyclohexyl]amino}propiophenone hydrochloride (I), cis 4'-fluoro-4-{[4-(o-butylphenyl)cyclohexyl]amino}butyro-β-naphthone hydrochloride (I), etc.

Following the procedure of Examples 40 and 41 but substituting another trans (or cis) 4-(substituted phenyl)cyclohexylamine hydrochloride (I) as starting material, such as
1. trans 4-(m-fluorophehyl)cyclohexylamine hydrochloride (I),
2. cis 4-(m-fluorophenyl)cyclohexylamine hydrochlororide (I),
3. trans 4-(p-chlorophenyl)cyclohexylamine hydrochlororide (I),
4. cis 4-(p-chlorophenyl)cyclohexylamine hydrochloride (I),
5. trans 4-(o-methylphenyl)cyclohexylamine hydrochloride (I),
6. cis 4-(o-methylphenyl)cyclohexylamine hydrochlororide (I),
7. trans 4-(m-methylphenyl)cyclohexylamine hydrochloride (I),
8. cis 4-(m-methylphenyl)cyclohexylamine hydrochloride (I),
9. trans 4-(p-methylphenyl)cyclohexylamine hydrochloride (I),
10. cis 4-(o-methylphenyl)cyclohexylamine hydrochloride (I),
11. trans 4-(o-methoxyphenyl)cyclohexylamine hydrochloride (I),
12. cis 4-(o-methoxyphenyl)cyclohexylamine hydrochloride (I),
13. trans 4-(m-methoxyphenyl)cyclohexylamine hydrochloride (I),
14. cis 4-(m-methoxyphenyl)cyclohexylamine hydrochloride (I),
15. trans 4-(p-methoxyphenyl)cyclohexylamine hydrochloride (I),
16. cis 4-(p-methoxyphenyl)cyclohexylamine hydrochloride (I),
17. trans 4-(m-trifluoromethylphenyl)cyclohexylamine hydrochloride (I),
18. cis 4-(m-trifluoromethylphenyl)cyclohexylamine hydrochloride (I),
19. trans 4-(p-trifluoromethylphenyl)cyclohexylamine hydrochloride (I),
20. cis 4-(p-trifluoromethylphenyl)cyclohexylamine hydrochloride (I), etc., yields, respectively,
1. trans 4'-fluoro-4-{[4-(m-fluorophenyl)cyclohexyl]amino}butyrophenone hydrochloride (I), melting point 197° to ° C. and
Anal. Calcd. for $C_{22}H_{26}ClF_2NO$: C, 67.04; H, 6.55; N, 3.56. Found: C, 67.34; H, 7.26; N, 3.43.
2. cis 4'-fluoro-4{[4-(m-fluorophenyl)cyclohexyl]amino}butyrophenone hydrochloride (I),
3. trans 4'-fluoro-4-{[4-(p-chlorophenyl)cyclohexyl]amino}butyrophenone hydrochloride (I),
4. cis 4'-fluoro-4-{[4-(p-chlorophenyl)cyclohexyl]amino}butyrophenone hydrochloride (I),
5. trans 4'-fluqro-4-{[4-(o-methylphenyl)cyclohexyl]amino}butyrophenone hydrochloride (I), m.p. 194° to 198°C. and
Anal. Calcd. for $C_{23}H_{29}ClFNO$: C, 70.84; H, 7.50; N, 3.59. Found: C, 71.32; H, 8.09; N, 3.87
6. cis 4'-fluoro-4-{[4-(o-methylphenyl)cyclohexyl]amino}butyrophenone hydrochloride (I), 7. trans 4'-fluoro-4-{[4-(m-methylphenyl)cyclohexyl]amino}butyrophenone hydrochloride (I), m.p. 195° to 198° C. and Anal. Calcd. for $C_{23}H_{29}ClFNO$: C, 70.84; H, 7.50; N, 3.59. Found: C, 71.63; H, 7.93; N, 3.51.

8. cis 4'-fluoro-4-{[4-(m-methylphenyl)cyclohexyl]amino}butyrophenone hydrochloride (I), 9. trans 4'-fluoro-4-{[4-(p-methylphenyl)cyclohexyl]amino}butyrophenone hydrochloride (I), m.p. 227° to 230°C. and Anal. Calcd. for $C_{23}H_{29}ClFNO$: C, 70.84; H, 7.50; N, 3.59. Found: C, 71.63; H, 7.93; N, 3.51.

10. cis 4'-fluoro-4-{[4-(p-methylphenyl)cyclohexyl]amino}butyrophenone hydrochloride (I), 11. trans 4'-fluoro-4-{[4-(o-methoxyphenyl)cyclohexyl]amino}butyrophenone hydrochloride (I), m.p. 233° to 235° C. and Anal. Calcd. for $C_{23}H_{29}ClFNO_2$: C, 68.05; H, 7.20; N, 3.45. Found: C, 68.02; H, 7.82; N, 3.51.

12. cis 4'-fluoro-4-{[4-(o-methoxyphenyl)cyclohexyl]amino}butyrophenone hydrochloride (I), 13. trans 4'-fluoro-4-{[4-(m-methoxyphenyl)cyclohexyl]amino}butyrophenone hydrochloride (I), m.p. 183° to 185° C. and Anal. Calcd. for $C_{23}H_{29}ClFNO_2$: C, 68.05; H, 7.20; N, 3.45. Found: C, 67.78; H, 7.20; N, 3.20.

14. cis 4'-fluoro-4-{[4-(m-methoxyphenyl)cyclohexyl]amino}butyrophenone hydrochloride (I), 15. trans 4'-fluoro-4-{[4-(p-methoxyphenyl)cyclohexyl]amino}butyrophenone hydrochloride (I), m.p. 191° to 193° C.

Anal. Calcd. for $C_{23}H_{29}ClFNO_2$: C, 68.05; H, 7.20; N, 3.45. Found: C, 68.29; H, 7.43; N, 3.33.

16. cis 4'-fluoro-4-{[4-(p-methoxyphenyl)cyclohexyl]amino}butyrophenone hydrochloride (I), 17. trans 4'-fluoro-4-{[4-(m-trifluoromethylphenyl)cyclohexyl]amino}butyrophenone hydrochloride (I), m.p. 197° to 201° C. and Anal. Calcd. for $C_{23}H_{26}ClF_4NO$: C, 62.23; H, 5.90; Cl, 7.99. Found: C, 62.32; H, 6.10; Cl, 8.08.

18. cis 4'-fluoro-4-{[4-(m-trifluoromethylphenyl)cyclohexyl]amino}butyrophenone hydrochloride (I), 19. trans 4'-fluoro-4-{[4-(p-trifluoromethylphenyl)cyclohexyl]amino}butyrophenone hydrochloride (I), m.p. 206° to 210° c. and Anal. Calcd. for $C_{23}H_{26}F_4NO$: C, 62.23; H, 5.90; Cl, 7.99. Found: C, 62.11; H, 6.46; Cl, 8.03.

20. cis 4'-fluoro-4-{[4-(p-trifluoromethylphenyl)cyclohexyl]amino}butyrophenone hydrochloride (I), etc.

Example 42: trans 4'-fluoro-4-{[4-(p-fluorophenyl)cyclohexyl]methylamino}butyrophenone hydrochloride (I)

To a suspension of 1.98 g. of trans N-methyl-[4-(p-fluorophenyl)cyclohexyl]amine hydrochloride (I) (prepared as in Example 34) in 27 ml. of dimethylformamide, 0.35 g. of sodium hydride (56% in mineral oil) is added. Following about 30 minutes of stirring there is added successively, 2.54 g. of potassium carbonate, 1.54 g. of potassium iodide and 2.23 g. of the 2,2-dimethyl-1,3-propanediol ketal of 4-chloro-4'-fluorobutyrophenone. The mixture is stirred at about 90° C. for about 18 hours, allowed to cool and diluted with benzene and water. The organic layer is washed with water and brine and taken to dryness. A solution of the residue in 64 ml. of methanol and 32 ml. of 2.5N hydrochloric acid is stirred for about 2 hours at room temperature. The methanol is then removed under vacuum and the residue extract extracted with methylene chloride. The organic layer is washed once with 2.5N hydrochloric acid and taken to dryness. The residual solid is recrystallized twice from methylene chloride:ethyl acetate to give trans 4'-fluoro-4-{[4-(p-fluorophenyl)cyclohexyl]methylamino}-butyrophenone hydrochloride (I), m.p. 206° to 207.5° C.

Anal. Calcd. $C_{23}H_{28}ClF_2NO$: C, 67.72; H, 6.92; Cl, 8.69. Found: C, 67.91; H, 7.29; Cl, 8.78.

Following the procedure of Example 42 but substituting an acid addition salt of another trans N-methyl-[4-(substituted phenyl)cyclohexyl]amine (I) as starting material and the 2,2-dimethyl-1,3-propanediol ketal of another ω-haloalkanaryl ketone, such as 1. trans N-methyl-[4-(o-propylphenyl)cyclohexyl]amine hydrochloride (I) and the 2,2-dimethyl-1,3-propanediol ketal of 4-chloro-2'-methylbutyrophenone,
2. trans N-methyl-[4-(m-trifluoromethylphenyl)cyclohexyl]amine hydrochloride (I) and the 2,2-dimethyl-1,3-propanediol ketal of 4-chloro-4'-methoxybutyrophenone,
3. trans N-methyl-[4-(p-butoxyphenyl)cyclohexyl]amine nitrate (I) and the 2,2-dimethyl-1,3-propanediol ketal of 2,2'-dichloracetophenone,
4. trans N-methyl-[4-(o-chlorophenyl)cyclohexyl]amine hydrochloride (I) and the 2,2-dimethyl-1,3-propanediol ketal of 5-chloro-4'-methylvalerophenone, etc., yields, respectively, 1. trans 2'-methyl-4-{[4-(o-propylphenyl)cyclohexyl]methylamino}butyrophenone hydrochloride (I),
2. trans 4'-methoxy-4{[4-(m-trifluoromethylphenyl)cyclohexyl]methylamino}butyrophenone hydrochloride (I),
3. trans 2'-chloro-2-{[4-(p-butoxyphenyl)cyclohexyl]methylamino}acetophenone nitrate (I),
4. trans 4'-methyl-5-{[4-(o-chlorophenyl)cyclohexyl]methylamino}valerophenone hydrochloride (I), etc.

Example 43: cis 4'-fluoro-4-{[4-(p-fluorophenyl)cyclohexyl]methylamino}butyrophenone hydrochloride (I)

Following the procedure of Example 42 but substituting cis N-methyl-[4-(p-fluorophenyl)cyclohexyl]amine hydrochloride (I) (prepared as in Example 35) as starting material, yields cis 4'-fluoro-4-{[4-(p-fluorophenyl)cyclohexyl]methylamino}butyrophenone hydrochloride (I), m.p. 191.1° to 193.5° C.

Anal. Calcd. for $C_{23}H_{28}ClF_2NO$: C, 67.72; H, 6.92; Cl, 8.69. Found: C, 67.97; H, 6.87; Cl, 8.68.

Following the procedure of Example 43 and the one set forth in the paragraph following Example 42, yields compounds such as cis 4'-methoxy-4-{[4-(o-trifluoromethylphenyl)cyclohexyl]methylamino}propiophenone hydrochloride (I), etc.

Example 44: trans N-[4,4-bis(p-fluorophenyl)butyl]-4-(p-fluorophenyl)-cyclohexylamine hydrochloride (I)

To 1 g. of trans 4-(p-fluorophenyl)cyclohexylamine hydrochloride (I) (prepared as in Example 20) in 15 ml. of dimethylformamide, 0.19 g. of a 56% dispersion of sodium hydride in mineral oil is added. Following about 15 minutes of stirring, 1.5 g. of potassium carbonate, 0.9 g. of potassium iodide and 1.57 g. of 1,1- bis(p-fluorophenyl)-4-chlorobutane [prepared as in Example CLVIII of U.S. Pat. No. 3,238,216, wherein it is named 1-chloro-4,4-di(4-fluorophenyl)butane] is added. Following about 18 hours of heating at about 95° C., the mixture is dissolved in water and benzene. The organic layer is washed with water and brine and taken to dryness. The residue is chromatographed on 150 ml. of silica gel (silicic acid) with elution by ammonia saturated methylene chloride; those fractions found similar by thin layer chromatography (TLC) are combined. A solution of the product in methylene chloride is washed with 2.5N hydrochloric acid and taken to dryness. This hydrochloride salt is freeze dried from benzene to give trans N-[4,4-bis(p-fluorophenyl)butyl]-4-(p-fluorophenyl)cyclohexylamine hydrochloride (I).

Following the procedure of Example 44 but substituting an acid addition salt of another trans 4-(substituted phenyl)cyclohexylamine (I) and another 1,1-bis(substituted phenyl)ω-haloalkane, such as 1. trans 4-(o-chlorophenyl)cyclohexylamine hydrochloride (I) and 1-(p-fluorophenyl)-1-(p-trifluoromethylphenyl)-4-chlorobutane,
2. trans 4-(m-ethoxyphenyl)cyclohexylamine hydrobromide (I) and 1,1-bis(p-tolyl)-4-chlorobutane,
3. trans 4-(p-butylphenyl)cyclohexylamine hydrochloride (I) and 1-(p-fluorophenyl)-1-phenyl-4-chlorobutane,
4. trans 4-(o-trifluoromethylphenyl)cyclohexylamine hydrochloride (I) and 1,1-bis(p-ethoxyphenyl)-2-chloroethane,
5. trans 4-(m-bromophenyl)cyclohexylamine hydrochloride (I) and 1,1-bis(p-fluorophenyl)-2-chloroethane, etc., yields, respectively,
   1. trans N-[4-(p-fluorophenyl)-4-(p-trifluoromethylphenyl)butyl]-4-(o-chlorophenyl)cyclohexylamine hydrochloride (I),
   2. trans N-[4,4-bis(p-tolyl)butyl]-4-(m-ethoxyphenyl)cyclohexylamine hydrobromide (I),
   3. trans N-[4-(p-fluorophenyl)-4-phenyl]butyl-4-(p-butylphenyl)cyclohexylamine hydrochloride (I),
   4. trans N-[2,2-bis(p-ethoxyphenyl)ethyl]-4-(o-trifluoromethylphenyl)cyclohexylamine hydrochloride (I),
   5. trans N-[2,2-bis(p-fluorophenyl)ethyl]-4-(m-bromophenyl)cyclohexylamine hydrochloride (I), etc.

Example 45: cis N-[4,4-bis(p-fluorophenyl)butyl]-4-(p-fluorophenyl)cyclohexylamine hydrochloride (I)

Following the procedure of Example 44 but substituting cis 4-(p-fluorophenyl)cyclohexylamine hydrochloride (I) (prepared as in Example 21) as starting material, yields cis N-[4,4-bis(p-fluorophenyl)butyl]-4-(p-fluorophenyl)cyclohexylamine hydrochloride (I).

Following the procedure of Example 45 and the one set forth in the paragraph following Example 44, yields compounds such as cis N-[2,2-bis(m-ethoxyphenyl)ethyl]-4-(o-ethylphenyl)cyclohexylamine hydrochloride (I), cis N-[2,2-bis(m-ethoxyphenyl)ethyl]-4-(o-ethylphenyl)cyclohexylamine hydrochloride (I), cis N-[4-(p-fluorophenyl)-4-(p-tolyl)butyl]-4-(p-bromophenyl)cyclohexylamine cyclohexanesulfamate (I), cis N-[4-(p-fluorophenyl)-4-phenyl]butyl-4-(o-trifluoromethylphenyl)cyclohexylamine hydrochloride (I), cis N-[4,4-bis (p-tolyl)butyl]-4-(m-propoxyphenyl)cyclohexylamine hydrochloride (I), etc.

Example 46 cis and trans 4-(p-fluoro-o-tolyl)-1,4-cyclohexanediol (This compound is obtained in a manner similar to that described for its 1-(p-methoxyphenyl) counterpart in Example 1, above.)

A. 4-[(tetrahydropyran-2-yl)oxy]cyclohexanone

A solution comprising 10 g. of 4-hydroxycyclohexanone, 10 g. of dihydropyran and 0.5 g. of p-toluenesulfonic acid in 100 ml. of ether is allowed to stand at room temperature for about 2.5 hours. The solution is then washed with saturated aqueous sodium bicarbonate solution and brine, 50 ml. of dry benzene added and the solution then evaporated to dryness to give 4-[(tetrahydropyran-2-yl)oxy]cyclohexanone as an oil.

B. 2-amino-5-fluorotoluene hydrochloride

To a solution of 25 g. of 5-fluoro-2-nitrotoluene (obtained as in J. Org. Chem. 26, 3351) in 150 ml. of ethyl acetate, 1 g. of 10% palladium on charcoal catalyst is added and the mixture shaken under hydrogen until three equivalents of the gas is absorbed. The catalyst is then removed by filtration and the filtrate taken to dryness. The residue is dissolved in a small volume of ether and a slight excess of 4.9 N hydrogen chloride in ether is added. The solid that precipitates is collected on a filter to yield 2-amino-5-fluorotoluene hydrochloride.

Free base NMR: aromatic protons - a complex multiplet 7.1 –7.6δ (2H); singlet 3.9δ (3H).

C. 2-bromo-5-fluorotoluene

To a suspension of 40.3 g. of 2-amino-5-fluorotoluene hydrochloride (obtained as in B, above) in 250 ml. of ether, 21 ml. of 50% aqueous sodium hydroxide solution is added. The mixture is stirred until the solid dissolves and the organic layer washed with brine and evaporated to dryness. To the ice-cooled residue dissolved in 87 ml. of 48% hydrobromic acid, 190 ml. of water and 190 g. of ice, a solution of 19.3 g. of sodium nitrite in 160 ml. of water is added dropwise. The resulting solution is added in small portions to an ice-cooled mixture of 80 ml. of 48% hydrobromic acid, 29 ml. of water, 5.45 g. of cupric oxide and 6.4 g. of copper powder that is previously heated at reflux for about 1 hour and then cooled, and the further addition of 64 g. of ice and 8 ml. of 48% hydrobromic acid. The combined mixture is allowed to stir at room temperature for about 1 hour and is then steam distilled, about 900 ml. of distillate being collected. The distillate is extracted with ether and the extracts washed successively with aqueous N sodium hydoxide solution, water and brine and then evaporated to dryness. The residue is distilled under vacuum (at 9 mm. of Hg) to yield 2-bromo-5-fluorotoluene having a boiling point of 56° to 58°C.

NMR: aromatic region, two doublets 8.5 to 8.8δ; complex multiplet 7.05 to 7.55δ (3H); singlet 3.7δ (3H).

D. cis and trans 4-(p-fluoro-o-tolyl)-1,4-cyclohexanediol

A solution of the Grignard reagent prepared from 18.9 g. of 2-bromo-5-fluorotoluene (obtained as in C, above) and 2.43 g. of magnesium in 120 ml. of tetrahydrofuran is cooled in ice. To this is added a solution of the 4-[(tetrahydropyran-2-yl)oxy]cyclohexanone (obtained from 10 g. of 4-hydroxycyclohexanone in 100 ml. of tetrahydrofuran, in the manner described in A, above). Following about 17 hours of standing at room temperature, the mixture is cooled in ice and mixed with 100 ml. of saturated aqueous ammonium chloride solution. The organic layer is washed with water and brine and evaporated to dryness. The residual gum is dissolved in 100 ml. of methanol and stirred with 10 ml. of 2.5N hydrochloric acid for about 1 hour. The bulk of the solvent is removed under vacuum and the resulting solid cis and trans 4-(p-fluoro-o-tolyl)-1,4-cyclohexanediol collected on a filter. The filtrate is extracted with ether and the organic layer taken to dryness. This residue is combined with the filtered solid.

Following the procedure of D, but substituting other starting materials such as 2-bromo-5-fluoro-3-ethylbenzene, 2,4-dichloro-6-propylbenzene, 2-bromo-5-butyl-6-fluorobenzene and the like, yields, respectively, the cis and trans isomers of 4-(p-fluoro-o-ethyl)phenyl-1,4-cyclohexanediol, 4-(4-chloro-6-propyl)phenyl-1,4-cyclohexanediol, 4-(5-butyl-6-fluoro)phenyl-1,4-cyclohexanediol and the like.

Example 47:
4-(p-fluoro-o-tolyl)-4-hydroxycyclohexanone

The cis and trans 4-(p-fluoro-o-tolyl)-1,4-cyclohexanediol obtained in Example 46 is suspended in 200 ml. of acetone cooled in an ice bath. The well stirred cold suspension is treated with 30 ml. of Jones reagent. The solvent is removed under vacuum and the residue treated with ether and water. The insoluble precipitate is collected on a filter and the organic layer of the filtrate washed with water and brine and evaporated to dryness. The residue is treated with 20 ml. of ether and the insoluble residue collected on a filter. The two solid fractions are combined and recrystallized from acetone:Skellysolve B to give 10.35 g, of 4-(p-fluoro-o-tolyl)-4-hydroxycyclohexanone having a melting point of 158° to 160°C.

Anal. Calcd. for $C_{13}H_{15}FO_2$: C, 70.25; H, 6.80. Found: C, 70.42; H, 6.96.

Following the procedure of Example 47 but substituting other starting materials such as the cis and trans isomers of 4-(p-chloro-o-propyl)phenyl-1,4-cyclohexanediol, 4-(4-bromo-6-butyl)phenyl-1,4-cyclohexanediol, 4-(5-chloro-6-propyl)phenyl-1,4-cyclohexanediol and the like, yields, respectively, 4-(p-chloro-o-propyl)phenyl-4-hydroxycyclohexanone, 4-(4-bromo-6-butyl)phenyl-4-hydroxycyclohexanone, 4-(5-chloro-6-propyl)phenyl-4-hydroxycyclohexanone and the like.

Example 48: 4-(p-fluoro-o-tolyl)cyclohexanone

A. 4-(p-fluoro-o-tolyl)-3-cyclohexen-1-one

To 25 ml. of well stirred trifluoroacetic acid, 5.35 g. of 4-(p-fluoro-o-tolyl)-4-hydroxycyclohexanone (obtained as in Example 47) is added. After about 10 minutes, the mixture is poured into an excess of aqueous sodium bicarbonate solution and the material that precipitates is extracted with ether. The extract is washed with aqueous sodium bicarbonate solution, water and brine and then evaporated to dryness to give 4(p-fluoro-o-tolyl)-3-cyclohexen-1-one.

B. 4-(p-fluoro-o-tolyl)cyclohexanone

A mixture of a solution of the residual 4-(p-fluoro-o-tolyl)-3-cyclohexen-1-one (obtained in A, above) in 150 ml. of ethyl acetate and 0.25 g. of 10% palladium on carbon catalyst is shaken under hydrogen until one equivalent of the gas is absorbed. The catalyst is then removed on a filter and the filtrate evaporated to dryness. The residue is recrystallized from Skellysolve B to give 4.43 g. of 4-(p-fluoro-o-tolyl)cyclohexanone having a melting point of 96° to 98° C.

Anal. Calcd. for $C_{13}H_{15}FO$: C, 75.70; H, 7.33. Found: C, 75.93; H, 7.54.

Following the procedure of Example 48 but substituting other starting materials such as 4-(p-chloro-o-ethyl)phenyl-4-hydroxycyclohexanone, 4-(3-bromo-6-propyl)phenyl-4-hydroxycyclohexanone and the like, yields respectively, 4-(p-chloro-o-ethyl)phenyl-cyclohexanone, 4-(3-bromo-6-propyl)phenyl-cyclohexanone, 4-(4-butyl-7-chloro)phenyl-cyclohexanone and the like.

Example 49: 4-(p-fluoro-o-tolyl)cyclohexanone oxime

A mixture of 4.43 g. of 4-(p-fluoro-o-tolyl)-cyclohexanone (prepared in Example 48), 4.5 g. of hydroxylamine hydrochloride and 9 ml. of aqueous 45% potassium hydroxide solution in 100 ml. of tetrahydrofuran is heated at reflux for about 6 hours. The mixture is then concentrated under vacuum and diluted with water and the solid that precipitates collected on a filter. It is recrystallized from methylene chloride:Skellysolve B to give 4.43 g. of 4-(p-fluoro-o-tolyl)cyclohexanone oxime having a melting point of 148° to 151° C.

Anal. Calcd. for $C_{13}H_{16}FNO$: C, 70.56; H, 7.29; N, 6.33. Found: C, 70.46; H, 7.29; N, 6.41.

Following the procedure of Example 49 but substituting other starting materials such as 4-(m-chloro-p-ethyl)phenylcyclohexanone, 4-(3-bromo-5-propyl)-phenyl-cyclohexanone, 4-(3-butyl-6-chloro)phenyl-cyclohexanone and the like, yields, respectively, 4-(m-chloro-o-ethyl)phenyl cyclohexanone oxime, 4-(3-bromo-5-propyl)phenyl cyclohexanone oxime, 4-(3-butyl-6-chloro)phenyl cyclohexanone oxime and the like.

Example 50: 4-(p-fluoro-o-tolyl)cyclohexanone oxime acetate

A solution of 4.43 g. of 4-(p-fluoro-o-tolyl)cyclohexanone oxime (prepared in Example 49) in 25 ml. of acetic anhydride and 50 ml. of pyridine is allowed to stand at room temperature for about 18 hours. The solution is then poured into ice-water and the precipitated solid collected on a filter and recrystallized from methylene chloride:Skellysolve B to give 4.66 g. of 4-(p-fluoro-o-tolyl)cyclohexanone oxime acetate having a melting point of 82° to 85° C.

Anal. Calcd. for $C_{15}H_{18}FNO_2$: C, 68.42; H, 6.89; N, 5.32. Found: C, 68.55; H, 7.07; N, 5.47.

Following the procedure of Example 50 but substituting other starting materials such as 4-(o-bromomethyl)phenyl cyclohexanone oxime, 4-(2-bromo-4-butyl)phenyl cyclohexanone oxime, 4-(3-chloro-5-isobutyl)phenyl cyclohexanone oxime and the like, yields the corresponding acetates.

Example 51: trans 4-(p-fluoro-o-tolyl)cyclohexylamine hydrochloride (I)

To an ice-cooled solution of 4.66 g. of 4-(p-fluoro-o-tolyl)cyclohexanone oxime acetate (obtained in Example 50) in 50 ml. of tetrahydrofuran, 50 ml. of N borane in tetrahydrofuran is added dropwise. The solution is allowed to stand in the cold for about 18 hours and then 1 ml. of water is added dropwise. The solvent is removed under vacuum and the residue stirred for about 2 hours with 100 ml. of 0.5N hydrochloric acid and 50 ml. of ether. The organic layer is separated and extracted further with 0.5N hydrochloric acid and finally water. The combined aqueous portions are made strongly basic and extracted with ether; this extract on evaporation to dryness yields the free base form of trans 4-(p-fluoro-o-tolyl)cyclohexylamine (I). The free base (I) on being treated with an excess of 4.9N hydrochloric acid in ether precipitates the solid hydrochloride (I), which on recrystallization from methanol:ethyl acetate gives trans 4-(p-fluoro-o-tolyl)cyclohexylamine hydrochloride (I) having a melting point higher than 300°C.

Anal. Calcd. for $C_{13}H_{19}ClFN$: C, 64.05; H, 7.86; N, 5.75. Found: C, 64.27; H, 8.02; N, 5.78.

The methanol:ethyl acetate mother liquor contains the isomeric cis 4-(p-fluoro-o-tolyl)cyclohexylamine hydrochloride (I); it can be isolated and purified by conventional procedures, e.g., gradient elution chromatography or fractional crystallization. The methanol:ethyl acetate solution (mother liquor) is diluted with water to give an amorphous precipitate consisting mostly of cis 4-(p-fluoro-o-tolyl)cyclohexylamine hydrochloride (I). This material is suspended in methylene chloride and adsorbed on a column of Florisil (synthetic magnesium silicate). The column is then subjected to gradient elution chromatography with mixtures of 10 to 100 % acetone in Skellysolve B and the eluate evaporated to dryness to give a solid that is crystallized from a mixture of methanol and water to yield cis 4-(p-fluoro-o-tolyl)cyclohexylamine hydrochloride (I). Alternatively, the methanol:ethyl acetate solution (mother liquor) is isolated and purified by fractional crystallization from hot methanol to yield a product consisting entirely of cis 4-(p-fluoro-o-tolyl)-cyclohexylamine hydrochloride (I).

Following the procedures of the immediately preceding paragraph and Example 51, but substituting other starting materials such as 4-(o-chloro-p-ethyl)phenyl cyclohexanone oxime acetate, 4-(3-bromo-4-propyl)-phenyl cyclohexanone oxime acetate, 4-(3-fluoro-5-isobutyl)phenyl cyclohexanone oxime acetate and the like, yields respectively, the cis and trans isomers of 4-(o-chloro-p-ethyl)phenyl cyclohexylamine hydrochloride (I), 4-(3-bromo-4-propyl)phenyl cyclohexylamine hydrochloride (I), 4-(3-fluoro-5-isobutyl)phenyl cyclohexylamine hydrochloride (I) and the like.

Following the procedure of Example 51 and the paragraphs thereafter, but substituting for hydrochloric acid, another acid such as hydrobromic, sulfuric, phosphoric, nitric, benzoic, naphthoic, salicylic, tartaric, nicotinic, cyclohexanesulfamic, hexynoic, lactic, palmitic, glutanic, acetic, propionic, phenylbutyric acid, and the like, yields a corresponding acid addition salt of a cis or trans 4-(p-fluoro-o-tolyl)cyclohexylamine hydrobromide (I), trans 4-(3-chloro-4-ethyl)phenyl cyclohexylamine sulfate (I), cis 4-(2-bromo-3-propyl)-phenyl cyclohexylamine phosphate (I), etc.

Example 52: trans 1-[4-(p-fluoro-o-tolyl)cyclohexyl]piperidine (I)

Following the procedure of Example 22 but substituting trans 4-(p-fluoro-o-tolyl)cyclohexylamine hydrochloride (I) (prepared as in Example 51) as starting material, yields trans 1-[4-(p-fluoro-o-tolyl)cyclohexyl]piperidine (I).

The thus produced free base on being dissolved in ether and treated with 3.6N ethereal hydrogen chloride, gives a solid precipitate, which on recrystallization (e.g., from methanol:ethyl acetate) yields trans 1-[4-(p-fluoro-o-tolyl)cyclohexyl]piperidine hydrochloride (I), m.p. 300°–304° C.

Following the procedure of Example 52 and the paragraph thereafter, but substituting another starting material, such as trans 4-(m-chloro-p-ethyl)phenyl cyclohexylamine hydrochloride (I), trans 4-(3-fluoro-5-propyl)phenyl cyclohexylamine hydrochloride (I) and the like, yields, respectively, trans 1-[4-(m-chloro-p-ethyl)phenyl cyclohexyl]piperidine (I), trans 1-[4-(3-fluoro-5-propyl)phenyl cyclohexyl]piperidine (I), and the like, or the hydrochlorides thereof.

Example 53: cis 1-[4-(p-fluoro-o-tolyl)cyclohexyl]piperidine hydrochloride (I)

Following the procedure of Example 23 but substituting cis 4-(p-fluoro-o-tolyl)cyclohexylamine hydrochloride (I) (prepared as in the paragraph immediately following Example 51) as starting material, yields cis 1-[4-(p-fluoro-o-tolyl)cyclohexyl]piperidine hydrochloride (I).

Following the procedure of Example 53 but substituting other starting materials, such as cis 4-(p-chloro-m-ethyl)phenyl cyclohexylamine hydrochloride (I), cis 4-(3-bromo-5-butyl)phenyl cyclohexylamine hydrochloride (I) and the like, yields, respectively, cis 1-[4-(p-chloro-m-ethyl)phenyl cyclohexyl]piperidine hydrochloride (I), cis 1-[4-(3-bromo-5-butyl)phenyl cyclohexyl]piperidine hydrochloride (I) and the like.

Example 54: trans 1-[4-(p-fluoro-o-tolyl)cyclohexyl]pyrrolidine (I)

Following the procedure of Example 24 but substituting trans 4-(p-fluoro-o-tolyl)cyclohexylamine hydrochloride (I) (prepared as in Example 51) as starting material, yields trans 1-[4-(p-fluoro-o-tolyl)cyclohexyl]pyrrolidine (I).

Dissolving the thus produced compound in ether and treating it with 3.6N ethereal hydrogen chloride yields trans 1-[4-(p-fluoro-o-tolyl)cyclohexyl]pyrrolidine hydrochloride (I).

Following the procedure of Example 54 but substituting other starting materials, such as trans 4-(p-bromo-o-ethyl)phenyl cyclohexylamine hydrochloride (I), trans 4-(2-chloro-6-propyl)phenyl cyclohexylamine hydrochloride (I) and the like, yields, respectively, trans 1-[4-(p-bromo-o-ethyl)phenyl cyclohexyl]pyrrolidine (I), trans 1-[4-(2-chloro-6-propyl)phenyl cyclohexyl]pyrrolidine (I) and the like.

Example 55: cis 1-[4-(p-fluoro-o-tolyl)cyclohexyl]pyrrolidine (I)

Following the procedure of Example 25 but substituting other starting materials, such as
1. cis 4-(p-fluoro-o-tolyl) cyclohexylamine hydrochloride (I),
2. cis 4-(p-bromo-m-ethyl)phenyl cyclohexylamine hydrochloride (I),
3. cis 4-(3-chloro-5-propyl)phenyl cyclohexylamine hydrochloride (I) and the like, yields, respectively,
1. cis 1-[4-(p-fluoro-o-tolyl)cyclohexyl]pyrrolidine (I),
2. cis 1-[4-(p-bromo-m-ethyl)phenyl cyclohexyl]-pyrrolidine (I),
3. cis 1-[4-(3-chloro-6-propyl)phenyl cyclohexyl]-pyrrolidine (I) and the like.

Dissolving a thus produced compound in ether and treating it with 3.6N ethereal hydrogen chloride yields its corresponding hydrochloride (I).

Example 56: cis 1-[4-(p-fluoro-o-tolyl)cyclohexyl]hexamethylenimine hydrochloride (I)

Following the procedure of Example 26 but substituting cis 4-(p-fluoro-o-tolyl)cyclohexylamine hydrochloride (I) as starting material, yields cis 1-[4-(p-fluoro-o-tolyl)cyclohexyl]hexamethylenimine hydrochloride (I).

Similarly, employing other dihaloalkanes with appropriate modifications of the procedures described in Examples 22 through 26, yields representative cis 1-[4-(disubstituted phenyl)cyclohexyl]unsubstituted and monosubstituted piperidines, pyrrolidines, hexamethylenimines, morpholines and piperazines, such as cis 1-[4-(p-fluoro-o-tolyl)cyclohexyl]-3-ethylpiperidine hydrochloride (I), cis 1-[4-(o-bromo-p-ethyl)phenyl cyclohexyl]-3-propylpyrrolidine hydrochloride (I), cis 1-[4-(p-chloro-o-propyl)phenyl cyclohexyl]-3-methoxyhexamethylenimine hydrochloride (I), cis 1-[4-(o-butyl-m-fluoro)phenyl cyclohexyl]morpholine hydrochloride (I), cis 1-[4-(m-chloro-p-tolyl)cyclohexyl]-2-methylmorpholine hydrochloride (I), cis 1-[4-(o-bromo-o-butyl)phenyl cyclohexyl]piperazine hydrochloride (I), and the like.

Example 57: trans 1-[4-(p-fluoro-o-tolyl)cyclohexyl]hexamethylenimine hydrochloride (I)

Following the procedure of Example 27 but substituting trans 4-(p-fluoro-o-tolyl)cyclohexylamine hydrochloride (I) as starting material, yields trans 1-[4-(p-fluoro-o-tolyl)cyclohexyl]hexamethyleneimine hydrochloride (I).

Following the procedure set forth in the paragraph following Example 56 but employing starting materials having trans stereoconfiguration, yields representative trans 1-[4-(disubstituted phenyl)cyclohexyl]unsubstituted and monosubstituted piperidines, pyrrolidines, hexamethylenimines, morpholines and piperazines, such as trans 1-[4-(p-fluoro-o-tolyl)cyclohexyl]-3-methylpiperidine hydrochloride (I), trans 1-[4-(o-chloro-m-ethyl)phenyl cyclohexyl]-2-ethylmorpholine hydrochloride (I), trans 1-[4-(o-bromo-p-butyl)phenyl cyclohexyl]piperazine hydrochloride (I), and the like.

Example 58: trans 1-[4-(p-fluoro-o-tolyl)cyclohexyl]-3-methylurea (I)

Following the procedure of Example 28 but substituting trans 4-(p-fluoro-o-tolyl)cyclohexylamine hydrochloride (I) (prepared as in Example 51) as starting material, yields trans 1-[4-(p-fluoro-o-tolyl)cyclohexyl]-3-methylurea (I).

Following the procedure of Example 58 but substituting other starting materials and other alkylisocyanates, such as trans 4-(p-chloro-o-ethyl)phenyl cyclohexylamine hydrochloride (I) and ethylisocyanate, trans 4-(o-bromo-p-butyl)phenyl cyclohexylamine hydrochloride (I) and propylisocyanate and the like, yields, respectively trans 1-[4-(p-chloro-o-ethyl)phenyl cyclohexyl]-3-ethylurea (I), trans 1-[4-(o-bromo-p-butyl)phenyl cyclohexyl]-3-propylurea (I) and the like.

Example 59: cis 1-[4-(p-fluoro-o-tolyl)cyclohexyl]-3-methylurea (I)

Following the procedure of Example 29 but substituting cis 4-(p-fluoro-o-tolyl)cyclohexylamine hydrochloride (I) as starting materials, yields cis 1-[4-(p-fluoro-o-tolyl)cyclohexyl]-3-methylurea (I).

Following the procedure of Example 59 and the paragraph following Example 58 yields compounds such as cis 1-[4-(m-bromo-o-tolyl)cyclohexyl]-3-ethylurea (I), cis 1-[4-(o-chloro-p-ethyl)phenyl cyclohexyl]-3-propylurea (I), cis 1-[4-(o-butyl-p-fluoro)phenyl cyclohexyl]-3-isobutylurea (I) and the like.

Example 60: trans N-[4-(p-fluoro-o-tolyl)cyclohexyl]methanesulfonamide (I)

Following the procedure of Example 30 but substituting trans 4-(p-fluoro-o-tolyl)cyclohexylamine hydrochloride (I) (prepared as in Example 51) as starting material, yields trans N-[4-(p-fluoro-o-tolyl)cyclohexyl]methanesulfonamide (I).

Following the procedure of Example 60 but substituting other starting materials and other organic sulfonyl halides, such as trans 4-(p-chloro-o-ethyl)penyl cyclohexylamine hydrochloride (I) and ethanesulfonyl chloride, trans 4-(o-bromo-p-propyl)phenyl cyclohexylamine hydrochloride (I) and p-toluenesulfonyl bromide, and the like, yields, respectively, trans N-[4-(p-chloro-o-ethyl)phenyl cyclohexyl]ethanesulfonamide (I), trans N-[4-(o-bromo-p-propyl)phenyl cyclohexyl]-p-toluenesulfonamide (I).

Example 61: cis N-[4-(p-fluoro-o-tolyl)cyclohexyl]methanesulfonamide (I)

Following the procedure of Example 31 but substituting cis 4-(p-fluoro-o-tolyl)cyclohexlamine hydrochloride (I) as starting material, yields cis N-[4-(p-fluoro-o-tolyl)cyclohexyl]methanesulfonamide (I).

Following the procedure of Example 61 but substituting other starting materials and other organic sulfonyl halides such as cis 4-(p-bromo-m-ethyl)phenyl cyclohexylamine hydrochloride (I) an propanesulfonyl chloride, cis 4-(o-chloro-p-propyl)phenyl cyclohexylamine hydrochloride (I) and the like, yields, respectively, cis N-[4-(p-bromo-m-ethyl)phenyl cyclohexyl]-propanesulfonamide (I), cis N-[4-(o-chloro-p-propyl)-phenyl cyclohexyl]-β-naphthalenesulfonamide (I), and the like.

Example 62: trans N-[4-(p-fluoro-o-tolyl)cyclohexyl]formamide (I)

Following the procedure of Example 32 but substituting trans 4-(p-fluoro-o-tolyl)cyclohexylamine (I) as starting material, yields trans N-[4-(p-fluoro-o-tolyl)-cyclohexyl]formamide (I).

Following the procedure of Example 62 but substituting other starting materials such as trans 4-(o-bromo-p-ethyl)phenyl cyclohexylamine (I), trans 4-(m-chloro-p-propyl)phenyl cyclohexylamine (I) and the like, yields, respectively trans N-[4-(o-bromo-p-ethyl)phenyl cyclohexyl]formamide (I), trans N-[b 4-(m-chloro-p-propyl)phenyl cyclohexyl]formamide (I) and the like.

Example 63: cis N-[4-(p-fluoro-o-tolyl)cyclohexyl]formamide (I)

Following the procedure of Example 33 but substituting cis 4-(p-fluoro-tolyl)cyclohexlamine (I) as starting material, yields cis N-[4-(p-fluoro-o-tolyl)cyclohexyl]-formamide (I).

Following the procedure of Example 63 but substituting other starting materials such as cis 4-(o-chloro-p- ethyl)phenyl cyclohexylamine (I), cis 4-(m-bromo-o-butyl)phenyl cyclohexylamine (I), cis 4-(o-fluoro-m-propyl)phenyl cyclohexylamine and the like, yields, respectively, cis N-[4-(o-chloro-p-ethyl)phenyl cyclohexl]formamide (I), cis N-[4-(m-bromo-o-butyl)phenyl cyclohexyl]formamide (I), cis N-[4-(o-fluoro-m-propyl)phenyl cyclohexyl]formamide (I) and the like.

Example 64: trans N-methyl-[4-(p-fluoro-o-tolyl)cyclohexyl]amine hydrochloride (I)

Following the procedure of Example 34 but substituting trans N-[4-(p-fluoro-o-tolyl)cyclohexyl]formamide (I) (prepared as in Example 62) as starting material, yields trans N-methyl-[4-(p-fluoro-o-tolyl)cyclohexyl]amine hydrochloride (I).

Following the procedure of Example 64 but substituting another starting material, such as trans N-[4-(o-bromo-p-ethyl)phenyl cyclohexyl]formamide, (I), trans N-[4-(m-chloro-p-propyl)phenyl cyclohexyl]formamide (I) and the like, yields, respectively, trans N-methyl-[4-(o-bromo-p-ethyl)phenyl cyclohexyl]formamide (I), trans N-methyl-[4-(m-chloro-p-propyl)phenyl cyclohexyl]formamide (I) and the like.

Example 65: cis N-methyl-[4-(p-fluoro-o-tolyl)cyclohexyl]amine hydrochloride (I)

Following the procedure of Example 35 but substituting cis N-[4-(p-fluoro-o-tolyl)cyclohexyl]formamide (I) (prepared as in Example 63) as starting material, yields cis N-methyl-[4-(p-fluoro-o-tolyl)cyclohexyl]amine hydrochloride (I).

Following the procedure of Example 65 but substituting another starting material, such as cis N-[4-(m-chloro-p-ethyl)phenyl cyclohexyl]formamide (I), cis N-[4-(o-bromo-p-butyl)phenyl cyclohexyl]formamide (I) and the like, yields, respectively, cis N-methyl-[4-(m-chloro-p-ethyl)phenyl cyclohexyl]formamide (I), cis N-methyl-[4-(o-bromo-p-butyl)phenyl cyclohexyl]formamide (I) and the like.

Example 66: trans N-methyl-4-(p-fluoro-o-tolyl)cyclohexyl-1-carbamic acid ethyl ester (I)

Following the procedure of Example 36 but substituting the free base form of trans N-methyl-[4-(p-fluoro-o-tolyl)cyclohexyl]amine hydrochloride (I) (obtained as in Example 64) as starting material, yields trans N-methyl-4-(p-fluoro-o-tolyl)cyclohexyl-1-carbamic acid ethyl ester (I).

Following the procedure of Example 66 but substituting another starting material and another alkylhaloformate, such as trans N-methyl-[4-(o-bromo-p-ethyl)phenyl cyclohexyl]amine (I) and propyl chloroformate, trans N-methyl-[4-(m-chloro-p-isopropyl)phenyl cyclohexyl]amine (I) and methyl bromoformate and the like, yields, respectively, trans N-methyl-4-(o-bromo-p-ethyl)phenyl cyclohexyl-1-carbamic acid propyl ester (I), trans N-methyl-4-(m-chloro-p-isopropyl)phenyl cyclohexyl-1-carbamic acid methyl ester (I) and the like.

Example 67: cis N-methyl-4-(p-fluoro-o-tolyl)cyclohexyl-1-carbamic acid ethyl ester (I)

Following the procedure of Example 37 but substituting the free base for of cis N-methyl-[4-(p-fluoro-o-tolyl)cyclohexyl]amine hydrochloride (I) (obtained as in Example 65) as starting material, yields cis N-methyl-4-(p-fluoro-o-tolyl)cyclohexyl-1carbamic acid ethyl ester (I).

Following the procedure of Example 67 but substituting another starting material and another alkylhaloformate, such as cis N-methyl-[4-(o-chloro-o-ethyl)phenyl cyclohexyl]amine (I) and propyl bromoformate, cis N-methyl-[4-(m-bromo-p-butyl)phenyl cyclohexyl]amine (I) and butyl chloroformate (I) and the like, yields, respectively, cis N-methyl-4-(o-chloro-p-ethyl)phenyl cyclohexyl-1-carbamic acid propyl ester (I), cis N-methyl-4-(m-bromo-p-butyl)phenyl cyclohexyl-1-carbamic acid butyl ester (I) and the like.

Example 68: trans N,N-dimethyl-4-(p-fluoro-o-tolyl)cyclohexylamine hydrochloride (I)

Following the procedure of Example 38 but substituting trans N-methyl-4-(p-fluoro-o-tolyl)cyclohexyl-1-carbamic acid ethyl ester (I) (prepared as in Example 66) as starting material, yields trans N,N-dimethyl-4-(p-fluoro-o-tolyl)cyclohexlamine hydrochloride (I).

Following the procedure of Example 68 but substituting another starting material, such as trans N-methyl-4-(o-bromo-p-ethyl)phenyl cyclohexyl-1-carbamic acid methyl ester (I), trans N-methyl-4-(m-chloro-o-propyl)phenyl cyclohexyl-1-carbamic acid propyl ester (I) and the like, yields, respectively, trans N,N-dimethyl-4-(o-bromo-p-ethyl)phenyl cyclohexylamine hydrochloride (I), trans N,N-dimethyl-4-(m-chloro-o-propyl)phenyl cyclohexylamine hydrochloride (I) and the like.

Example 69: cis N,N-dimethyl-4-(p-fluoro-o-tolyl)cyclohexylamine hydrochloride (I)

Following the procedure of Example 39 but substituting cis N-methyl-4-(p-fluoro-o-tolyl)cyclohexyl-1-carbamic acid ethyl ester (I) (prepared as in Example 67) as starting material, yields cis N,N-dimethyl-4-(p-fluoro-o-tolyl)cyclohexylamine hydrochloride (I).

Following the procedure of Example 69 but substituting another starting material, such as cis N-methyl-4-(o-fluoro-p-ethyl)phenyl cyclohexyl-1-carbamic acid methyl ester (I), cis N-methyl-4-(m-bromo-o-butyl)phenyl cyclohexyl-1-carbamic acid butyl ester (I) and the like, yields, respectively, cis N,N-dimethyl-4-(o-fluoro-o-ethyl)phenyl cyclohexylamine hydrochloride, cis N,N-dimethyl-4-(m-bromo-o-butyl)phenyl cyclohexylamine hydrochloride (I) and the like.

Example 70: trans 4′-fluoro-4-{[4-(p-fluoro-o-tolyl)cyclohexyl-]amine}butyrophenone hydrochloride (I)

To a suspension of 1.73 g. of trans 4-(p-fluoro-o-tolyl)cyclohexylamine hydrochloride (I) (prepared as in Example 51) in 40 ml. of dimethylformamide, 0.31 g. of 56% sodium hydride in mineral oil is added. After about 1 hour of stirring, 2 g. of potassium, 1.2 g. of potassium iodide and 1.82 g. of the 2,2-dimethyl-1,3-propanediol ketal of 4-chloro-4′-fluorobutyrophenone are added successively. The mixture is stirred in an oil bath at about 90° C. for about 18 hours, allowed to cool and the solvent removed under vacuum by a rotary evaporator. The residue is dissolved in benzene and water; the organic layer is washed with water and brine and then taken to dryness. The residue is dissolved in 30 ml. of methanol, 15 ml. of 2.5N hydrochloric acid is added and the mixture stirred for about 1 hour, then concentrated under vacuum. The precipitated solid is collected on a filter and on recrystallization from methanol:2.5N hydrochloric acid gives pure trans 4′-fluoro-4-{[4-(p-fluoro-o-tolyl)cyclohexyl]amino}butyrophenone hydrochloride (I) melting at 215° to 218° C.

Anal. Calcd. for $C_{23}H_{28}ClF_2NO\cdot\frac{1}{2}H_2O$: C, 66.25; H, 7.07; N, 3.36. Found: C, 66.64; H, 6.82; N, 3.39.

Heating the hydrated compound at about 100° C. for about 24 hours in a vacuum oven yields the corresponding anhydrous compound having the empirical formula $C_{23}H_{28}ClF_2NO$.

Following the procedure of Example 70 but substituting cis 4-(p-fluoro-o-tolyl)cyclohexylamine hydrochloride (I) (obtained as in the paragraph immediately following Example 51) as starting material, yields cis 4′-fluoro-4-{[4-(p-fluoro-o-tolyl)cyclohexyl]amino}butyrophenone hydrochloride (I).

Following the procedures of Example 70 and the paragraphs thereafter but substituting an acid addition salt of another trans or cis 4-(disubstituted phenyl)cyclohexylamine (I) as starting material and the 2,2-dimethyl- 1,3-propanediol ketal of another ω-haloalkanaryl ketone, such as 1. trans 4-(o-bromo-p-ethyl)phenyl cyclohexylamine hydrochloride (I) and the 2,2-dimethyl ketal of 4′-bromo-4-chlorobutyrophenone, 2. cis 4-(m-chloro-o-propyl)phenyl cyclohexylamine hydrobromide and the 2,2-dimethyl-1,3-propanediol ketal of 4′-butoxy-4-chlorobutyrophenone, 3. trans 4-(p-fluoro-m-isopropyl)phenyl cyclohexylamine nitrate (I) and the 2,2-dimethyl-1,3-propanediol ketal of 4-chloro-2′-methylbutyrophenone, 4. cis 4-(m-bromo-o-butyl)phenyl cyclohexylamine cyclohexanesulfamates (I) and the 2,2-dimethyl-1,3-propanediol ketal of 3′,4-dichlorobutyrophenone, 5. trans 4(o-fluoro-p-ixobutyl)phenyl cyclohexylamine sulfate (I) and the 2,2-dimethyl-1,3-propanediol ketal of 4-chloro-2′-butyrophenone and the like, yields, respectively, 1. trans 4′-bromo-4-{[4-(o-bromo-p-ethyl)phenyl cyclohexyl]amino}butyrophenone hydrocloride (I), 2. cis 4′-butoxy-4-{[4-(m-chloro-o-propyl)phenyl cyclohexyl]amino}butyrophenone hydrobromide (I), 3. trans 2′-methyl-4-{[4-(p-fluoro-m-isopropyl)penyl cyclohexyl]amine}butyrophenone nitrate (I), 4. cis 3′-chloro-4-{[4-(m-bromo-o-butyl)phenyl cyclohexyl]amine}butyrophenone cyclohexanesulfamate (I), 5. trans 2′-methyl-4-{[4-(o-fluoro-p-isobutyl)phenyl cyclohexyl]amino}butyrophenone sulfate (I) and the like.

Example 71: trans 4′-fluoro-4-{[4-(p-fluoro-o-tolyl)cyclohexyl[methylamino}butyrophenone hydrochloride (I)

Following the procedure of Example 42 but substituting trans N-methyl-[4-(p-fluoro-o-tolyl)cyclohexl]amine hydrochloride (I) (prepared as in Example 64) as starting material, yields trans 4′-fluoro-4-{[4-(p-fluoro-o-tolyl)cyclohexyl]methylamino}butyrophenone hydrochloride (I).

Following the procedure of Example 71 but substituting another starting material and 2,2-dimethyl-1,3-propanediol ketal of another ω-haloalkanaryl ketone, such as trans N-methyl-[4-(p-bromo-o-ethyl)phenyl cyclohexyl]amine hydrochloride (I) and the 2,2-dimethyl-1,3-propanediol ketal of 3-chloro-4′-methylbutyrophenone, trans N-methyl-[4-(o-chloro-m-propyl)phenyl cyclohexyl]amine hydrochloride (I) and the 2,2-dimethyl-1,3-propanediol ketal of 340 -bromo-4-chlorobutyrophenone, and the like, yields, respectively, trans 4-′-methyl-{[4-(p-bromo-o-ethyl)phenyl cyclohexyl]methylamino}butyrophenone hydrochloride (I), trans 3′-bromo-{[4-(o-chloro-m-propyl)phenyl cyclohexyl methylamino}butyrophenone hydrochloride (I).

Example 72: cis 4′-fluoro-4-{[4-(p-fluoro-o-tolyl)cyclohexyl]methylamino}butyrophenone hydrochloride (I)

Following the procedure of Example 43 but substituting cis N-methyl-[4-(p-fluoro-o-tolyl)cyclohexyl]amine hydrochloride (I) (prepared as in Examle 65) as starting material, yields, cis 4′-fluoro-4-{[4-(p-fluoro-o-tolyl)cyclohexyl]methylamino}butyrophenone hydrochloride (I).

Following the procedure of Example 72 but substituting another starting material and the 2,2-dimethyl-1,3-propanediol ketal of another ω-haloalkkanaryl ketone, such cis N-methyl-[4-(m-chloro-o-ethyl)phenyl cyclohexyl]amine hydrobromide (I) and the 2,2-dimethyl-1,3-propanediol ketal of 4′-butoxy-4-chlorobutyrophenone, cis N-methyl-[4-(o-bromo-p-butyl)phenyl cyclohexyl]amine hydrochloride (I) and the 2,2-dimethyl-1,3-propanediol ketal of 3′,4-dichlorobutyrophenone, and the like, yields, respectively, cis 4′-butoxy-4-{[4-(m-chloro-o-ethyl)phenyl cyclohexyl]methylamino}butyrophenone hydrobromide (I), cis 3′-chloro-4-{[4(o-bromo-p-butyl)phenyl cycloexyl]methylamino}butyrophenone hydrochloride (I).

Example 73: trans N-[4,4-bis(p-fluorophenyl)butyl]-4-(p-fluoro-o-tolyl)-cyclohexylamne hydrochloride (I)

Following the procedure of Example 44 but substituting trans 4-(p-fluoro-o-tolyl)cyclohexylamine hydrochloride (I) (prepared as in Example 51) as starting material, yields trans N-[4,4-bis(p-fluorophenyl)butyl]-4-(p-fluoro-o-tolyl)cyclohexylamine hydrochloride (I).

Following the procedure of Example 73 but substituting cis 4-(p-fluoro-o-tolyl)cyclohexylamine hydrochloride (I) (obtained as in the paragraph immediately followng Example 51) as starting material, yields cis N-[4,4-bis(p-fluorophenyl)butyl]-4-(p-fluoro-o-tolyl)-cyclohexylamne hydrochloride (I).

Following the procedures of Example 73 and the paragraph thereafter but substituting an acid addition salt of another trans or cis 4-(disubstituted phenyl)cyclohexylamine(I) as starting material and the 1,1-bis(-substituted phenyl)-ω-haloalkane, such as 1. trans 4-(o-bromo-p-ethyl)phenyl cyclohexylamine hydrochloride (I) and 1,1-bis(p-tolyl)-4-chorobutane, 2. cis 4-(m-chloro-o-propyl)phenyl cyclohexylamine hyrobromide (I) and 1-(p-fluorophenyl)-1-(p-trifluoromethylphenyl)-4-chlorobutane,
3. trans 4-(p-fluoro-o-isopropyl)phenyl cyclohexylamine nitrate (I) and 1,1-bis(p-ethoxyphenyl)-2-chloroethane,
4. cis 4-(p-bromo-m-butyl)phenyl cyclohexylamine hydrochloride (I) and 1,1bis(p-fluorophenyl)-2l-chloroethane,
5. trans 4-(o-chloro-p-isobutyl)phenyl cyclohexylamine hydrochloride (I) and 1(p-fluorophenyl)-1-phenyl-4-chlorobutane and the like, yields, respectively,
1. trans N-[4,4-bis(p-tolyl)butyl]-4-(o-bromo-p-ethyl)phenyl cyclohexylamine hydrochloride (I),
2. cis N-[4-(p-fluorophenyl)-4-(p-trifluoromethylphenyl)]butyl-4-(m-chloro-o-propyl)phenyl cyclohexylamine hydrobromide (I),
3. trans N-[2,2-bis(p-ethoxyphenyl)ethyl]-4-(p-fluoro-o-isopropyl)phenyl cyclohexylamine nitrate (I),
4. cis N-[2,2-bis(p-fluorophenyl)ethyl]-4-(p-bromo-m-butyl]phenyl cyclohexylamine hydrochloride (I),
5. trans N-[4-(p-fluorophenyl)-4-phenyl]butyl-4-(o-chloro-p-isobutyl)phenyl cyclohexylamine hydrochloride (I) and the like.

Example 74: cis and trans 4phenyl-1,4-cyclohexanediol (This compound is obtained in a manner similar to that described for its 1-(p-methoxyphenyl) counterpart in Example 1, above.)

To 2 l. of tetrahydrofuran, 460 ml. of 2.85 M phenyl magnesium bromide in ether is added. The solution is heated and 460 ml. of solvent is distilled from the mixture. The mixture is vigorously stirred with cooling and 30 g. of 4-hydroxycyclohexanone in 300 ml. of tetrahydrofuran is added. After standing at room temperature for about 17 hours, 500 ml. of saturated aqueous ammonium chloride is added. The organic layer is washed with water and brine, then evaporated to dryness to yield cis and trans 4phenyl-1,4-cyclohexanediol.

Example 75: 4-phenyl-4-hydroxycyclohexanone

The residue of cis and trans 4-phenyl-1,4cyclohexanediol obtained in Example 74 is dissolved in 110 ml. of acetone and cooled in an ice bath. Over the course of between about 5 and 10 minutes, 100 ml. of Jones reagent is added. The solvent is removed under vacuum and the residue dissolved in water and ether. The organic layer is washed with water, saturated aqueous sodium bicarbonate solution and evaporated to dryness. The residue is chromatographed over a column of 500 ml. of Florisil, elution being carried out first with 6 l. of 5% acetone in Skellysolve B, then with 20% acetone in Skellysolve B to give 4-phenyl-4-hydroxycyclohexanone melting at 120.5° to 123.5° C.

Anal. Calcd. for $C_{12}H_{14}O_2$: C, 75.76; H, 7.42. Found: C, 76.01; H, 7.81.

Example 76: 4-phenylcyclohexanone

A. 4-phenyl-3-cyclohexen-1-one

To 34 ml. of well stirred trifluoroacetic acid, 50 g. of 4-phenyl-4-hydroxycyclohexanone (obtained as in Example 75) is added. After about 5 minutes the mixture is poured into an excess of aqueous sodium bicarbonate solution. The precipitated material is extracted with ether and the extract washed with water and brine and evaporated to dryness to give 4-phenyl-3-cyclohexen-1-one.

B. 4-phenylcyclohexanone

A mixture of a solution of the residue of 4-phenyl-3-cyclohexen-1-one (obtained in A, above) in 150 ml. of ethyl acetate and 0.27 g. of palladium on carbon catalyst is shaken under hydrogen until one equivalent of the gas is absorbed. The catalyst is then removed on a filter and the filtrate evaporated to dryness. The residue is recrystallized from petroleum ether to give 3.99 g. of 4-phenylcyclohexanone having a melting point of 72° to 75° C.

Anal. Calcd. for $C_{12}H_{14}O$: C, 82.77; H, 8.10. Found: C, 82.24; H, 8.02.

Example 77: 4-phenylcyclohexanone oxime

A mixture of 8.08 g. of 4-phenylcyclohexanone (obtained as in Example 76), 8 g. of hydroxylamine hydrochloride and 16 ml. of 45% aqueous potassium hydroxide solution in 100 ml. of ethanol, is heated at reflux for about 4 hours. The mixture is concentrated under vacuum and then diluted with water. The precipitated solid is collected on a filter and recrystallized from Skellysolve B to give 7.5 g. of 4-phenylcyclohexanone oxime having a melting point of 110° to 112° C.

Anal. Calcd. for $C_{12}H_{15}NO$: C, 76.15; H, 7.99; N, 7.40. Found: C, 75.91; H, 8.04; N, 7.24.

Example 78: 4-phenylcyclohexanone oxime acetate

A solution of 7.5 g. of 4-phenylcyclohexanone oxime (prepared in Example 77) in 23 ml. of acetic anhydride and 45 ml. of pyridine is allowed to stand at room temperature for about 18 hours. The solution is then poured into ice water and the precipitated solid collected on a filter and recrystallized from Skellysolve B to give 8.58 g. of 4-phenylcyclohexanone oxime acetate having a melting point of 89° to 91° C.

Anal. Calcd. for $C_{14}H_{17}NO_2$: C, 72.70; H, 7.41; N, 6.06. Found: C, 72.44; H, 7.68; N, 6.05.

Example 79: trans 4-phenylcyclohexylamine hydrochloride

Into a solution of 8.58 g. of 4-phenylcyclohexanone oxime acetate (prepared in Example 79) in 90 ml. of tetrahydrofuran and 27 ml. of t-butanol, 350 ml. of ammonia is distilled from over sodium. To this there is added 1.9 g. of lithium in three portions at a rate that the blue color just persists. When the final blue color fades, 10 g. of solid ammonium chloride is added and the solvent is then evaporated with a stream of nitrogen. The residue is dissolved in ether and aqueous N-sodium hydroxide solution. The organic layer is separated, washed with water and brine and then taken to dryness to give a residue of trans 4-phenylcyclohexylamine. The residue is dissolved in a small amount of ether and treated with an excess of 4.9N hydrogen chloride in ether. The precipitate that forms is collected on a filter to yield 7.9 g. of trans 4-phenylcyclohexylamine hydrochloride. A sample of identical material previously prepared melts above 300° C.

Anal. Calcd. for $C_{12}H_{18}ClN$: C, 68.07; H, 8.57; N, 6.62.
Found: C, 68.18; H, 8.63;
N, 6.59.

The ether mother liquor contains the isomeric cis 4-phenylcyclohexylamine hydrochloride; it can be isolated and purified in the manner described for the corresponding cis 4-disubstituted phenyl compound, namely, cis 4-(p-fluoro-o-tolyl)cyclohexylamine hydrochloride (I), in the paragraph immediately following Example 51, above.

Example 80: trans 4-phenylcyclohexylamine acetamide

A solution of the free base obtained from 7.9 g. of trans 4phenylcyclohexylamine hydrochloride (prepared in Example 79) in 15 ml. of acetic anhydride and 30 ml. of pyridine is allowed to stand at room temperature for about 2 hours. The resulting mixture is diluted with water and the solid collected on a filter. A single recrystallization from acetone:hexene gives 5.77 g. of trans 4-phenylcyclohexylamine acetamide melting at 158° to 161° C.

Found: Calcd. for $C_{14}H_{19}NO$: C, 77.38; H, 8.81; N, 6.45. Found: C, 76.71; H, 9.49; N, 6.64.

Cis 4-phenylcyclohexylamine acetamide is recovered from the acetone:hexene mother liquor, being isolated and purified in the manner described in the paragraph following Example 79, above.

Following the procedures of Example 80 and the paragraph immediately thereafter, but substituting another anhydride of a hydrocarbon carboxylic acid, such as propionic anhydride or butyric anhydride in Example 80, yields the corresponding trans and cis 4-phenylcyclohexylamine propionamides and butyramides.

Example 81: trans N-[4-(p-nitrophenyl)cyclohexyl]acetamide

To an ice-cooled solution of 4.67 g. of trans 4-phenylcyclohexylamine acetamide (obtained as in Example 80) in 25 ml. of trifluoroacetic acid, 9 ml. of nitric acid is added. Following about 4 hours of standing in the cold, the mixture is poured onto ice. The precipitate is extracted with methylene chloride and the organic layer washed with aqueous sodium bicarbonate solution. The organic solution is evaporated to dryness and the residue chromatographed on a 500 ml. column of Florisil, with elution by 2 l. of 20% acetone in Skellysolve B. The higher melting solid fractions recovered are combined and recrystallized from a mixture of methylene chloride and ethyl acetate to give 3.09 g. (54% yield) of crystalline trans N-[4-(p-nitrophenyl)cyclohexyl]acetamide, having a melting point of 221° to 224° C.

Anal. Calcd. for $C_{14}H_{18}N_2O_3$: C, 64.10; H, 6.92; N, 10.68. Found: C, 63.81; H, 6.82; N, 10.41.

Cis N-[4-(p-nitrophenyl)cyclohexyl]acetamide is recovered from the methylene chloride:ethyl acetate mother liquor, being isolated and purified in the manner described in the paragraph following Example 79, above.

Following the procedures of Example 81 and the paragraph immediately thereafter, but substituting another starting material, such as trans or cis 4-phenylcyclohexylamine propionylamide or 4-phenylcyclohexylamine butyramide in Example 81, yields the corresponding trans and cis N-[4-(p-nitrophenyl)cyclohexyl]acylamide.

Example 82: trans 4-(p-nitrophenyl)cyclohexylamine hydrochloride (I)

A solution of 5.25 g. of trans N-[4-(p-nitrophenyl)cyclohexyl]acetamide (prepared as in Example 81) in 50 ml. of hydrochloric acid and 50 ml. of methanol is heated at reflux for about 72 hours. The bulk of the methanol is then removed under vacuum and the residue dissolved in 100 ml. of hot water. The solution is then made strongly basic and extracted with ether and the organic layer then evaporated to dryness to give trans 4-(p-nitrophenyl)cyclohexylamine (I). The residue is dissolved in a small amount of ether which is then treated with 4.9 g. hydrochloric acid in ether to give 4.78 g. (99% yield) of trans N-4-(p-nitrophenyl)-cyclohexylamine hydrochloride (I). The analytical sample has a melting point of 293° to 294° C.

Anal. Calcd. for $C_{12}H_{17}N_2O$: C, 56.13; H, 6.68; N, 10.91. Found: C, 56.22; H, 7.00; N, 10.85.

Cis 4-(p-nitrophenyl)cyclohexylamine hydrochloride (I) is recovered from the ether mother liquor, being isolated and purified in the manner described in the paragraph following Example 79, above.

Example 83: trans N-[4-(p-aminophenyl)cyclohexyl]acetamide.

A mixture of 2.62 g. of trans N-[4-(p-nitrophenyl)cyclohexyl]acetamide (obtained as in Example 81) and 10 g. of Adams' platinum oxide catalyst in 150 ml. of ethanol is shaken under hydrogen (for about 10 minutes) until the theoretically required amount of the gas is absorbed. The catalyst is removed on a filter and the filtrate evaporated to dryness. The residual solid is recrystallized from aqueous methanol to give 2.03 g. (87% yield) of trans N-[4-(p-aminophenyl)cyclohexyl]acetamide having a melting point of 195° to 196.5° C.

Anal. Calcd. for $C_{14}H_{20}N2O$: C, 72.38; H, 8.68; N, 12.06. Found: C, 72.37; H, 8.84; N, 12.03.

Cis N-[4-(p-aminophenyl)cyclohexyl]acetamide is recovered from the aqueous methanol mother liquor, being isolated and purified in the manner described in the paragraph following Example 79, above.

Following the procedures of Example 83 and the paragraph immediately thereafter, but substituting another starting material, such as trans or cis N-[4-(p-nitrophenyl)cyclohexyl]propionylamide or N-[4-(p-nitrophenyl)cyclohexyl]butyramide in Example 83, yields the corresponding trans and cis N-[4-(p-aminophenyl)cyclohexyl]acylamide.

Example 84: trans 4-(p-aminophenyl)-N-ethylcyclohexylamine dihydrochloride

A solution of 4 g. of trans N-[4-(p-aminophenyl)cyclohexyl]acetamide (prepared as in Example 83) in 150 ml. of tetrahydrofuran is added to 1.4 g. of lithium aluminum hydride in 10 ml. of tetrahydrofuran. The mixture is heated at reflux for about 3 hours and allowed to stand for about 16 hours. The cooled mixture is then heated with 1.4 ml. of water and 1.4 ml. of 15% aqueous sodium hydroxide solution and an additional 1.4 ml. of water. The solid is removed on a filter and the filtrate evaporated to dryness. The residual oily solid is suspended in ether. This mixture is filtered to give 0.63 g. of starting material melting at 190° to 194° C. The filtrate is evaporated to dryness and the residue dissolved in 75 ml. of tetrahydrofuran and added to 2 g. of lithium aluminum hydride in 200 ml. of tetrahydrofuran. After about 17 hours of heating at reflux temperature and about 17 hours at room temperature, the cooled mixture is heated with 2 ml. of water and 2 ml. of 15% aqueous sodium hydroxide solution and an additional 2 ml. of water. The solid is removed on a filter and the filtrate evaporated to dryness to give the crude product, which is dissolved in 50 ml. of methanol and then treated with 6.5 ml. of 4.7N hydrochloric acid in ether. The solution is evaporated to dryness and the residue recrystallized from methanol:ethyl acetate to give 3.55 g. (80% yield) of trans 4-(p-aminophenyl)-N-ethylcyclohexylamine dihydrochloride melting at 291° to 295° C.

Anal. Calcd. for $C_{14}H_{24}ClN_2$: C, 55.42; H, 8.45; N, 9.24. Found: C, 55.38; H, 8.79; N, 8.73.

Cis 4-(p-aminophenyl)-N-ethylcyclohexylamine dihydrochloride is recovered from the methanol:ethyl acetate mother liquor, being isolated and purified in the manner described in the paragraph following Example 79, above.

Following the procedures of Example 84 and the paragraph immediately thereafter, but substituting another starting material, such as trans or cis N-[4-(p-aminophenyl)cyclohexyl]propionamide or N-[4-(p-aminophenyl)cyclohexyl]butyramide in Example 84, yields the corresponding trans and cis 4-(p-aminophenyl)-N-alkylcyclohexylamine dihydrochloride.

Example 85: trans N-[4-(p-sulfamoylphenyl)cyclohexyl]acetamide

An ice cold slurry of 4.64 g. of trans N-[4-(p-aminophenyl)cyclohexyl]acetamide (obtained as in Example 83) in 10 ml. of hydrochloric acid and 10 ml. of water is diazotized with a solution of 1.55 g. of sodium nitrite in 5 ml. of water. The resulting dark solution is added in the course of about 5 minutes to 20 ml. of acetic acid containing 0.8 g. of cuprous chloride in 2 ml. of water, and then saturated with sulfur dioxide. Following about 2.5 hours of stirring at room temperature, the black solution is diluted with water. The mixture is extracted with ether and the organic layer washed with water and brine. The solution is evaporated to dryness to give a waxy solid crude sulfonyl chloride derivative containing some acetic acid. A solution of this material in 50 ml. of tetrahydrofuran is added to 50 ml. of tetrahydrofuran saturated with ammonia. The gas is bubbled in for about an additional hour. The solvent is removed under vacuum and the residue suspended in methylene chloride and water. The insoluble solid is collected on a filter and recrystallized twice from methanol to give 0.77 g. (13% yield) of solid trans N-[4-(p-sulfamoylphenyl)cyclohexyl]acetamide having a melting point 268° to 269° C.

Anal. Calcd. for $C_{14}H_{20}N_2O_3S$: C, 56.73; H, 6.80; N, 9.45. Found: C, 56.82; H, 6.75; N, 9.47.

Cis N-[4-(p-sulfamoylphenyl)cyclohexyl]acetamide is recovered from the methanol mother liquor, being isolated and purified in the manner described in the paragraph following Example 79, above.

Following the procedure of Example 85 and the paragraph immediately thereafter, but substituting another starting material, such as trans or cis N-[4-(p-aminophenyl)cyclohexyl]propionamide or N-[4-(p-aminophenyl)cyclohexyl]butyramide in Example 85, yields the corresponding trans and cis N-[4-(p-sulfamoylphenyl)cyclohexyl]acylamide.

Example 86: trans 1-[4-(p-nitrophenyl)cyclohexyl]piperidine (I)

Following the procedure of Example 22 but substituting trans 4-(p-nitrophenyl)cyclohexylamine hydrochloride (I) (prepared as in Example 82) as starting material, yields trans 1-[4-(p-nitrophenyl)cyclohexyl]piperidine (I).

The thus produced free base on being dissolved in ether and treated with 3.6N ethereal hydrogen chloride, gives a solid precipitate which on recrystallization (e.g., from methanol:ethyl acetate) yields trans 1-[4-(p-nitrophenyl)cyclohexyl]piperidine hydrochloride (I).

Example 87: cis 1-[4-(p-nitrophenyl)cyclohexyl]piperidine hydrochloride (I)

Following the procedure of Example 23 but substituting cis 4-(p-nitrophenyl)cyclohexylamine hydrochloride (I) (prepared as in the paragraph immediately following Example 82) as starting material, yields cis 1-[4-(p-nitrophenyl)cyclohexyl]piperidine hydrochloride (I).

Example 88: trans 1-[4-(p-nitrophenyl)cyclohexyl]pyrrolidine (I)

Following the procedure of Example 24 but substituting trans 4-(p-nitrophenyl)cyclohexylamine hydrochloride (I) as starting material, yields trans 1-[4-(p-nitrophenyl)cyclohexyl]pyrrolidine (I).

Dissolving the thus produced compound in ether and treating it with 3.6N ethereal hydrogen chloride yields trans 1-[4-(p-nitrophenyl)cyclohexyl]pyrrolidine hydrochloride (I).

Example 89: cis 1-[4-(p-nitrophenyl)cyclohexyl]pyrrolidine (I)

Following the procedure of Example 25 but substituting cis 4-(p-nitrophenyl)cyclohexylamine hydrochloride (I) as starting material, yields cis 1-[4-(p-nitrophenyl)cyclohexyl]pyrrolidine (I).

Dissolving the thus produced compound in ether and treating it with 3.6N ethereal hydrogen chloride yields cis 1-[4-(p-nitrophenyl)cyclohexyl]pyrrolidine hydrochloride (I).

Example 90: cis 1-[4-(p-nitrophenyl)cyclohexyl]hexamethylenimine hydrochloride (I)

Following the procedure of Example 26 but substituting cis 4-(p-nitrophenyl)cyclohexylamine hydochloride (I) as starting material, yields cis 1-[4-(p-nitrophenyl)-cyclohexyl]amine hydrochloride (I).

Similarly, employing other dihaloalkanes with appropriate modifications of the procedures described in Examples 22 through 26, yields representative cis 1-[4-(p-nitrophenyl)cyclohexyl]unsubstituted and monosubstituted piperidines, pyrrolidines, hexamethylenimines, morpholines and piperazines such as cis 1-[4-(p-nitrophenyl)cyclohexyl]-3-methylpiperidine hydrochloride (I), cis 1-[4-(p-nitrophenyl)cyclohexyl]-3-butylpyrrolidine hydrochloride (I), cis 1-[4-(p-nitrophenyl)cyclohexyl]-3-methoxyhexamethylenimine hydrochloride (I), cis 1-[4-(p-nitrophenyl)cyclohexyl]-morpholine hydrochloride (I), cis 1-[4-(p-nitrophenyl)cyclohexyl]-2-ethylmorpholine hydrochloride (I), cis 1-[4-(p-nitrophenyl)cyclohexyl]piperazine hydrochloride (I), and the like.

Example 91: trans 1-[4-(p-nitrophenyl)cyclohexyl]hexamethylenimine hydrochloride (I)

Following the procedure of Example 27 but substituting trans 4-(p-nitrophenyl)cyclohexylamine hydrochloride (I) as starting material, yields trans 1-[4-(p-nitrophenyl)cyclohexyl]hexamethylenimine hydrochloride (I).

Following the procedures of Example 22 through 26 with appropriate modifications and employing other dihaloalkanes, yields representative trans 1-[4-(p-nitrophenyl)cyclohexyl]unsubstituted and monosubstituted piperidines, pyrrolidines, hexamethylenimines, morpholines and piperazines, such as trans 1-[4-(p-nitrophenyl)cyclohexyl]-3-propylpiperidine hydrochloride (I), trans 1-[4-(p-nitrophenyl)cyclohexyl]-3-ethoxymethylenimine hydrochloride (I), trans 1-[4-(p-nitrophenyl)cyclohexyl]-2-ethylmorpholine hydrochloride (I), and the like.

Example 92: trans 1-[4-(p-nitrophenyl)cyclohexyl)]-3-methylurea (I)

Following the procedure of Example 28 but substituting trans 4-(p-nitrophenyl)cyclohexylamine hydrochloride (I) (prepared as in Example 82) as starting material, yields trans 1-[4-(p-nitrophenyl)cyclohexyl]-3-methylurea (I).

Following the procedure of Example 92 but substituting other alkylisocyanates such as ethylisocyanate, propylisocyanate and the like, yields, trans 1-[4-(p-nitrophenyl)cyclohexyl]-3-ethylurea (I), trans 1-[4-(p-nitrophenyl)cyclohexyl]-3-propylurea (I), and the like.

Example 93: cis 1-[4-(p-nitrophenyl)cyclohexyl]-3-methylurea (I)

Following the procedure of Example 29 but substituting cis 4-(p-nitrophenyl)cyclohexylamine hydrochloride (I) (prepared as in the paragraph immediately following Example 82) as starting material, yields cis 1-[4-(p-nitrophenyl)cyclohexyl]-3-methylurea (I).

Following the procedure of Example 93 but substituting another alkylisocyanate such as isopropylisocyanate, butylisocyanate and the like, yields, respectively, cis 1-[4-(p-nitrophenyl)cyclohexyl]-3-isopropylurea (I), cis 1-[4-(p-nitrophenyl)cyclohexyl]-3-butylurea (I), and the like.

Example 94: trans N-[4-(p-nitrophenyl)cyclohexyl]methanesulfonamide

Following the procedure of Example 30 but substituting trans 4-(p-nitrophenyl)cyclohexylamine hydrochloride (I) as starting material, yields trans N-[4-(p-nitrophenyl)cyclohexyl]amine hydrochloride (I).

Following the procedure of Example 94 but substituting other organic sulfonyl halides such as ethanesulfonyl chloride, p-toluenesulfonyl and the like, yields, respectively trans N-[4-(p-nitrophenyl)cyclohexyl]ethanesulfonamide (I), trans N-[4-(p-nitrophenyl)cyclohexyl]-p-toluenesulfonamide (I) and the like.

Example 95: cis N-[4-(p-nitrophenyl)cyclohexyl]methanesulfonamide (I)

Following the procedure of Example 31 but substituting cis 4-(p-nitrophenyl)cyclohexyl]methanesulfonamide (I).

Following the procedure of Example 95 but substituting other organic sulfonyl halides such as propanesulfonyl chloride, β-naphthalenesulfonyl bromide and the like, yields, respectively, cis N-[4-(p-nitrophenyl)cyclohexyl]propanesulfonamide (I), cis N-[4-(p-nitrophenyl)cyclohexyl]-β-naphthalenesulfonamide (I) and the like.

Example 96: trans N-[4-(p-nitrophenyl)cyclohexyl]formamide (I)

Following the procedure of Example 32 but substituting trans 4-(p-nitrophenyl)cyclohexylamine (I) as starting material, yields trans N-[4-(p-nitrophenyl)cyclohexyl]formamide (I).

Example 97: cis N-[4-(p-nitrophenyl)cyclohexyl]formamide (I)

Following the procedure of Example 33 but substituting cis 4-(p-nitrophenyl)cyclohexyl (I) as starting material, yields cis N-[4-(p-nitrophenyl)cyclohexyl]formamide (I).

Example 98: trans N-methyl-[4-(p-nitrophenyl)cyclohexyl]amine hydrochloride (I)

Following the procedure of Example 34 but substituting trans N-[4-(p-nitrophenyl)cyclohexyl]formamide (I) (prepared as in Example 96) as starting material, yields trans N-methyl-[4-(p-nitrophenyl)cyclohexyl]amine hydrochloride (I).

Example 99: cis N-methyl-[4-(p-nitrophenyl)cyclohexyl]amine hydrochloride (I)

Following the procedure of Example 35 but substituting cis N-[4-(p-nitrophenyl)cyclohexyl]formamide (I) (prepared as in Example 97) as starting material, yields cis N-methyl[4-(p-nitrophenyl)cyclohexyl]amine hydrochloride (I).

Example 100: trans N-methyl-4-(p-nitrophenyl)cyclohexyl-1-carbamic acid ethyl ester (I)

Following the procedure of Example 36 but substituting trans N-methyl-[4-(p-nitrophenyl)cyclohexyl]amine (I) as starting material, yields trans N-methyl-4-(p-nitrophenyl)cyclohexyl-1-carbamic acid ethyl ester (I).

Following the procedure of Example 100 but substituting another alkylhaloformate such as propyl chloroformate, methylbromoformate and the like, yields, respectively, trans N-methyl-4-(p-nitrophenyl)cyclohexyl-1carbamic acid propyl ester (I), trans N-methyl-4-(p-nitrophenyl)cyclohexyl-1-carbamic acid methyl ester (I), and the like.

Example 101: cis N-methyl-4-(p-nitrophenyl)cyclohexyl-1-carbamic acid ethyl ester (I)

Following the procedure of Example 37 but substituting cis N-methyl-[4-(p-nitrophenyl)cyclohexyl]amine (I) as starting material, yields cis N-methyl-4-(p-nitrophenyl)cyclohexyl-1-carbamic acid ethyl ester (I).

Following the procedure of Example 101 but substituting another alkylhaloformate sch as propylchloroformate, butylbromoformate and the like, yields, respectively, cis N-methyl-4-(p-nitrophenyl)cyclohexyl-1-carbamic acid propyl ester (I), cis N-methyl-4-(p-nitrophenyl)cyclohexyl-1-carbamic acid butyl ester (I), and the like.

Example 102: trans N,N-dimethyl-4-(p-nitrophenyl)cyclohexylamine hydrochloride (I)

Following the procedure of Example 38 but substituting trans N-methyl-4-(p-nitrophenyl)cyclohexyl-1-carbamic acid ethyl ester (I) (prepared as in Example 100) as starting material, yields trans N,N-dimethyl-4-(p-nitrophenyl)cyclohexylamine hydrochloride (I).

Example 103: cis N,N-dimethyl-4-(p-nitrophenyl)cyclohexylamine hydrochloride (I)

Following the procedure of Example 39 but substituting cis N-methyl-4-(p-nitrophenyl)cyclohexyl-1-carbamic acid ethyl ester (I) (prepared as in Example 101) as starting material, yields cis N,N-dimethyl-4-(p-nitrophenyl)cyclohexylamine hydrochloride (I).

Example 104: trans 4'-fluoro-4-{[4-(p-nitrophenyl)cyclohexyl]amino}butyrophenone hydrochloride (I)

To a suspension of 1.36 g. of trans 4-(p-nitrophenyl)-cyclohexylamine hydrochloride (I) (prepared as in Example 82) in 25ml. of dimethylformamide, 0.22 g. of 56% sodium hydride in mineral oil is added. The mixture is warmed on a steam bath and stirred at room temperature for about 1 hour. There is then added successively, 1.5 g. of potassium carbonate, 0.9 g. of potassium iodide and 1.33 g. of the 2,2-dimethyl-1,3-propanediol ketal of 4-chloro-4-fluorobutyrophenone. The mixture is stirred in an oil bath at about 90° C. for about 18 hours, allowed to cool and the solvent removed under vacuum. The residue is dissolved in benzene and water. The organic layer is washed with water and brine and then evaporated to dryness. The residue is dissolved in 30 ml. of methanol and 15 ml. of 2.5N hydrochloric acid is added. The mixture is stirred for about 2 hours and then concentrated under vacuum. The precipitated solid is collected on a filter and recrystallized from methanol: 2.5N hydrochloric acid to give pure trans 4'-fluoro-4-{[4-(p-nitrophenyl)cyclohexyl]amino}butyrophenone hydrochloride (I) having a melting point of 231° to 232° C.

Anal. Calcd. for $C_{22}H_{26}ClF_2O_3$: C, 62.77; H, 6.23; N, 6.66. Found: C, 62.97; H, 6.26; N, 6.42.

Following the procedure of Example 104 but substituting cis 4-(p-nitrophenyl)cyclohexylamine hydrochloride (I) (obtained as in the paragraph immediately following Example 82) as starting material, yields cis 4'-fluoro-4-{[4-(p-nitrophenyl)cyclohexyl]amino}butyrophenone hydrochloride (I).

Following the procedure of Example 104 and the paragraph thereafter and employing an acid addition salt of trans or cis 4-(p-nitrophenyl)cyclohexylamine (I) as starting material and the 2,2-dimethyl-1,3-propanediol ketal of another ω-haloalkanaryl ketone, such as
1. trans 4-(p-nitrophenyl)cyclohexylamine hydrochloride (I) and the 2,2-dimethyl ketal of 4'-bromo-4-chlorobutyrophenone,
2. cis 4-(p-nitrophenyl)cyclohexylamine hydrochloride (I) and the 2,2-dimethyl ketal of 4'-methoxy-4-chlorobutyrophenone,
3. trans 4-(p-nitrophenyl)cyclohexylamine nitrate (I) and the 2,2-dimethyl ketal of 4-chloro-2'-ethylbutyrophenone,
4. cis 4-(p-nitrophenyl)cyclohexylamine cyclohexanesulfamate (I) and the 2,2-dimethyl-1,3-propanediol ketal of 3',4-dichlorobutyrophenone,
5. trans 4-(p-nitrophenyl)cyclohexylamine sulfate (I) and the 2,2dimethyl-1,3propanediol ketal of 4-chloro-3'-methylbutyrophenone and the like, yields, respectively,
1. trans 4'-bromo-4-{[4-(p-nitrophenyl)cyclohexyl]amino}butyrophenone hydrochloride (I),
2. cis 4'-methoxy-4-{[4-(p-nitrophenyl)cyclohexyl]amino}butyrophenone hydrochloride (I),
3. trans 2'-ethyl-4-{[4-(p-nitrophenyl)cyclohexyl]amino}butyrophenone nitrate (I),
4. cis 3'-chloro-4-{[4-(p-nitrophenyl)cyclohexyl]amino}butyrophenone cyclohexanesulfamate (I),
5. trans 3'-methyl-4-{[4-(p-nitrophenyl)cyclohexyl]amino}butyrophenone sulfate (I) and the like.

Example 105: trans 4'-fluoro-4-{[4-(p-nitrophenyl)-cyclohexyl]methylamino}butyrophenone hydrochloride (1)

Following the procedure of Example 42 but substituting trans N-methyl-[4-(p-nitrophenyl)cyclohexyl]amine hydrochloride (1) (prepared as in Example 98) as starting material, yields trans 4'-fluoro-4-{[4-(p-nitrophenyl)cyclohexyl]-methylamino}butyrophenone hydrochloride (1).

Following the procedure of Example 105 but substituting the 2,2-dimethyl-1,3-propanediol ketal of another ω-haloalkanaryl ketone such as that of 3-chloro-4'-methylbutyrophenone, 3'-bromo-4-chlorobutyrophenone and the like, yields, respectively, trans 4'-methyl-4-{[4-(p-nitrophenyl)cyclohexyl]methylamino}butyrophenone hydrochloride (1), trans 3'-bromo-4-{[4-(p-nitrophenyl)cyclohexyl]methylamino}butyrophenone hydrochloride (1) and the like.

Example 106: cis 4'-fluoro-4-{[4-(p-nitrophenyl)cyclohexyl]methylamino}butyrophenone hydrochloride (1)

Following the procedure of Example 42 but substituting cis N-methyl-4-(p-nitrophenyl)cyclohexyl]amine hydrochloride (1) (prepared as in Example 99) as starting material, yields cis 4'-fluoro-4-{[4-(p-nitrophenyl)cyclohexyl]methylamino}-butyrophenone hydrochloride (1).

Following the procedure of Example 106 but substituting the 2,2-dimethyl-1,3-propanediol ketal of another ω-haloalkanaryl ketone such as that of 4-chloro-4-ethoxybutyrophenone, 3,4'-dichlorobutyrophenone and the like, yields, respectively, cis 4'-ethoxy-4-{[4-(p-nitrophenyl)cyclohexyl]methylamino}butyrophenone hydrochloride (1), cis 3'-chloro-4-{[4-(p-nitrophenyl)cyclohexyl]methylamino}butyrophenone hydrochloride (1) and the like.

Example 107: trans N-[4,4-bis(p-fluorophenyl)butyl]-4-(p-nitrophenyl)cyclohexylamine hydrochloride (1)

Following the procedure of Example 44 but substituting trans 4-(p-nitrophenyl)cyclohexylamine hydrochloride (1) (prepared as in Example 82) as starting material, yields trans N-[4,4-bis(p-fluorophenyl)butyl]-4-(p-nitrophenyl)cyclohexylamine hydrochloride (1).

Following the procedure of Example 107 but substituting cis 4-(p-nitrophenyl)cyclohexylamine hydrochloride (1) (obtained as in the paragraph immediately following Example 82) as starting material, yields cis N-[4,4-bis(p-fluorophenyl)butyl]-4-(p-nitrophenyl)cyclohexylamine hydrochloride (1).

Following the procedure of Example 107 and the paragraph thereafter and employing an acid addition salt of trans or cis 4-(p-nitrophenyl)cyclohexylamine (1) as starting material and another 1,1-bis(substituted phenyl)ω-haloalkane, such as 1. trans 4-(p-nitrophenyl)cyclohexylamine hydrochloride (1) and 1-(p-fluorophenyl)-1-(p-trifluoromethylphenyl)-4-chlorobutane,
2. cis 4-(p-nitrophenyl)cyclohexylamine hydrobromide (1) and 1,1-bis(p-tolyl)-4-chlorobutane,
3. trans 4-(p-nitrophenyl)cyclohexylamine nitrate (1) and 1-(p-fluorophenyl)-1-phenyl-4-chlorobutane,
4. cis 4-(p-nitrophenyl)cyclohexylamine cyclohexanesulfamate (1) and 1,1-bis(p-ethoxyphenyl)-2-chloroethane,
5. trans 4-(p-nitrophenyl)cyclohexylamine sulfate (1) and 1,1-bis(p-fluorophenyl)-2-chloroethane and the like, yields, respectively, 1. trans N-[4-(p-fluorophenyl)-4-(p-trifluoromethylphenyl]butyl-4-(p-nitrophenyl)cyclohexylamine hydrochloride (1),
2. cis N-[4,4-bis(p-tolyl)butyl]-4-(p-nitrophenyl)cyclohexylamine hydrobromide (1),
3. trans N-[4-(p-fluorophenyl)-4-phenyl]butyl-4-(p-nitrophenyl)cyclohexylamine nitrate (1),
4. cis N-[2,2-bis(p-ethoxyphenyl)ethyl]-4-(p-nitrophenyl)cyclohexylamine cyclohexanesulfamate (1),
5. trans N-[2,2-bis(p-fluorophenyl)ethyl]-4-(p-nitrophenyl)cyclohexylamine sulfate (1) and the like.

Example 108: trans 1-[4-(p-nitrophenyl)cyclohexyl]piperidine p-toluenesulfonate (1)

To a suspension of 1.84 g. of trans 4-(p-nitrophenyl)cyclohexylamine hydrochloride (1) (prepared as in Example 82) in 35 ml. of ethanol, 1.5 ml. of 4.18N methanolic sodium methoxide is added. After about 1 hour of stirring, 1.88 g. of 1,5-diiodopentane is added. The mixture is then heated at reflux for about 16 hours. The bulk of the solvent is removed under vacuum and the residue dissolved in ether and water. The organic layer is washed with water and brine and taken to dryness. The residue is dissolved in a small amount of ether and a solution of 0.93 g. of p-toluenesulfonic acid in ether added. The resulting precipitate is collected on a filter and recrystallized from methylene chloride:ethyl acetate to give trans 1-[4-(p-nitrophenyl)cyclohexyl]-piperidine p-toluenesulfonate (1) having a melting point of 171° to 180° C.

Anal. Calcd. for $C_{24}H_{32}N_2O_5S$: N, 6.08.
Found: N, 5.82.

Following the procedure of Example 108 but substituting cis 4-(p-nitrophenyl)cyclohexylamine hydrochloride (1) (obtained as in the paragraph immediately following Example 82) as starting material, yields, cis 1-[4-(p-nitrophenyl)cyclohexyl]piperidine p-toluenesulfonate (1).

Following the procedure of Example 108 and the paragraph thereafter but substituting another organic (alkyl or aryl) sulfonic acid, such as methanesulfonic, benzenesulfonic, α-naphthalenesulfonic and like acids, yields a corresponding trans or cis 1-[4-(p-nitrophenyl)cyclohexyl]piperidine organic (alkyl or aryl) sulfonate (1).

Following the procedure of Example 108 but substituting other trans (or cis) 4-(substituted phenyl)cyclohexylamine hydrochlorides (1) (prepared as in Examples 20 and 21 and the paragraphs following them) as starting materials, such as 1. trans (or cis) 4-(p-chlorophenyl)cyclohexylamine hydrochloride (1),
2. trans (or cis) 4-(m-trifluoromethylphenyl)cyclohexylamine hydrochloride (1),
3. trans (or cis) 4-(p-trifluoromethylphenyl)cyclohexylamine hydrochloride (1),
4. trans (or cis) 4-(o-methylphenyl)cyclohexylamine hydrochloride (1),
5. trans (or cis) 4-(m-methylphenyl)cyclohexylamine hydrochloride (1),
6. trans (or cis) 4-(p-methylphenyl)cyclohexylamine hydrochloride (1),
7. trans (or cis) 4-(o-methoxyphenyl)cyclohexylamine hydrochloride (1),
8. trans (or cis) 4-(m-methoxyphenyl)cyclohexylamine hydrochloride (1), etc., yields, respectively, 1. trans (or cis) 1-[4-(p-chlorophenyl)cyclohexyl]-piperidine p-toluenesulfonate (1),
2. trans (or cis) 1-[4-(m-trifluoromethylphenyl)cyclohexyl]piperidine p-toluenesulfonate (1),
3. trans (or cis) 1-[4-(p-trifluoromethylphenyl)cyclohexyl]piperidine p-toluenesulfonate (1),
4. trans (or cis) 1-[4-(o-methylphenyl)cyclohexyl]-piperidine p-toluenesulfonate (1),
5. trans (or cis) 1-[4-(m-methylphenyl)cyclohexyl]-piperidine p-toluenesulfonate (1),
6. trans (or cis) 1-[4-(p-methylphenyl)cyclohexyl]-piperidine p-toluenesulfonate (1),
7. trans (or cis) 1-[4-(o-methoxyphenyl)cyclohexyl]-piperidine p-toluenesulfonate (1),
8. trans (or cis) 1-[4-(m-methoxyphenyl)cyclohexyl]piperidine p-toluenesulfonate (1), etc.

I claim:
1. A compound of the formula

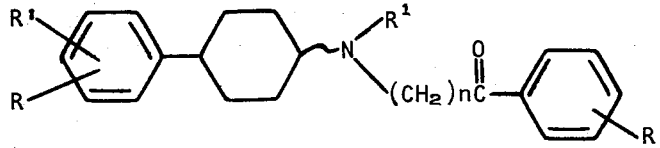

wherein ~ is a generic expression denoting cis and trans stereoconfiguration and mixtures thereof, R' and R are selected from the group consisting of hydrogen, alkyl of from one through four carbon atoms, fluorine, chlorine, bromine, trifluoromethyl, nitro and alkoxy of from one through four carbon atoms, $R^1$ is selected from the group consisting of hydrogen and alkyl of from one through four carbon atoms and $n$ is an integer of from one through six, and acid addition salts thereof.

2. A compound of claim 1 wherein R is p-fluoro, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-4-{[4-(p-fluorophenyl)cyclohexyl]amino}butyrophenone hydrochloride.

3. A compound of claim 1 wherein R is p-fluoro, R' is hydrogen, $R^1$ is methyl, $R^2$ is 4-oxo-4-(p-fluorophenyl)butyl, the stereoconfiguration is trans and the acid addition salt is that of hydrochloric acid, namely, trans 4'-fluoro-4-{[4-(p-fluorophenyl)cyclohexyl]methylamino}butyrophenone hydrochloride.

4. A compound of claim 1 wherein R is p-fluoro, R' and $R^1$ are hydrogen, $R^2$ is 4-oxo-4-(p-fluorophenyl)butyl, the stereoconfiguration is cis and the acid addition salt is that of hydrochloric acid, namely, cis 4'-fluoro-4-{[4-(p-fluorophenyl)cyclohexyl]amino}butyrophenone hydrochloride.

5. A compound of claim 1 wherein R is p-fluoro, R' is hydrogen, $R^1$ is methyl, $R^2$ is 4-oxo-4-(p-fluorophenyl)butyl, the stereoconfiguration is cis and the acid addition salt is that of hydrochloric acid, namely, cis 4'-fluoro-4-{[4-(p-fluorophenyl)cyclohexyl]methylamino}butyrophenone hydrochloride.

6. A compound of claim 1 wherein R is p-nitro, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-{[4-(p-nitrophenyl)cyclohexyl]amino}butyrophenone hydrochloride.

7. A compound of claim 1 wherein R is p-nitro, R' is hydrogen, $R^1$ is methyl, $R^2$ is 4-oxo-4-(p-fluorophenyl)butyl, the stereoconfiguration is trans and the acid addition salt is that of hydrochloric acid, namely, trans 4'-p-fluoro-{[4-(p-nitrophenyl)cyclohexyl]methylamino}butyrophenone hydrochloride.

8. A compound of claim 1 wherein R is p-nitro, R' and $R^1$ are hydrogen, $R^2$ is 4-oxo-4-(p-fluorophenyl)butyl, the stereoconfiguration is cis and the acid addition salt is that of hydrochloric acid, namely, cis 4'-fluoro-{[4-(p-nitrophenyl)cyclohexyl]amino}butyrophenone hydrochloride.

9. A compound of claim 1 wherein R is p-nitro, R' is hydrogen, $R^1$ is methyl, $R^2$ is 4-oxo-4-(p-fluorophenyl)butyl, the stereoconfiguration is cis and the acid addition salt is that of hydrochloric acid, namely, cis 4'-p-fluoro-{[4-(p-nitrophenyl)cyclohexyl]methylamino}butyrophenone hydrochloride.

10. A compound of claim 1 wherein R is p-fluoro, R' is o-methyl, $R^1$ is hydrogen, $R^2$ is 4-oxo-4-(p-fluorophenyl)butyl, the stereoconfiguration is trans and the acid addition salt is that of hydrochloric acid, namely, trans 4'-fluoro-{[4-(p-fluoro-o-tolyl)cyclohexyl]amino}butyrophenone hydrochloride.

11. A compound of claim 1 wherein R is p-fluoro, R' is o-methyl, $R^1$ is methyl, $R^2$ is 4-oxo-4-(p-fluorophenyl) butyl, the stereoconfiguration is cis and the acid addition salt is that of hydrochloric acid, namely, trans 4'-fluoro-{[4-(p-fluoro-o-tolyl)cyclohexyl]methylamino}-butyrophenone hydrochloride.

12. A compound of claim 1 wherein R is p-fluoro, R' is o-methyl, $R^1$ is hydrogen, $R^2$ is 4-oxo-4-(p-fluorophenyl)butyl, the stereoconfiguration is cis and the acid addition salt is that of hydrochloric acid, namely, cis 4'-fluoro- {[4-(p-fluoro-o-tolyl)cyclohexyl]amino}butyrophenone hydrochloride.

13. A compound of claim 1 wherein R is p-fluoro, R' is o-methyl, $R^1$ is methyl, $R^2$ is 4-oxo-4-(p-fluorophenyl) butyl, the stereoconfiguration is cis and the acid addition salt is that of hydrochloric acid, namely, cis 4'-fluoro-{[4-(p-fluoro-o-tolyl)cyclohexyl]methylamino}butyrophenone hydrochloride.

14. A compound of claim 1 wherein R is m-fluoro, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-4-{[4-(m-fluorophenyl)cyclohexyl]amino}butyrophenone hydrochloride.

15. A compound of claim 1 wherein R is m-fluoro, R' and $R^1$ are hydrogen, $R^2$ is 4-oxo-4-(p-fluorophenyl)butyl, the stereoconfiguration is cis and the acid addition salt is that of hydrochloric acid, namely, cis 4'-fluoro-4-{[4-(m-fluorophenyl)cyclohexyl]amino}butyrophenone hydrochloride.

16. A compound of claim 1 wherein R is p-chloro, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-4-{[4-(p-chlorophenyl)cyclohexyl]amino}butyrophenone hydrochloride.

17. A compound of claim 1 wherein R is p-chloro, R' and $R^1$ are hydrogen, $R^2$ is 4-oxo-4-(p-fluorophenyl)butyl, the stereoconfiguration is cis and the acid addition salt is that of hydrochloric acid, namely, cis 4'-fluoro-4-{[4-(p-chlorophenyl)cyclohexyl]amino}butyrophenone hydrochloride.

18. A compound of claim 1 wherein R is o-methyl, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-4-{[4-(o-methylphenyl)cyclohexyl]amino}butyrophenone hydrochloride.

19. A compound of claim 1 wherein R is o-methyl, R' and $R^1$ are hydrogen, $R^2$ is 4-oxo-4-(p-fluorophenyl)butyl, the stereoconfiguration is cis and the acid addition salt is that of hydrochloric acid, namely, cis 4'-fluoro-4-{[4-(o-methylphenyl)cyclohexyl]amino}butyrophenone hydrochloride.

20. A compound of claim 1 wherein R is m-methyl, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-4-{[4-(m-methylphenyl)cyclohexyl]amino}butyrophenone hydrochloride.

21. A compound of claim 1 wherein R is m-methyl, R' and $R^1$ are hydrogen, $R^2$ is 4-oxo-4-(p-fluorophenyl)butyl, the stereoconfiguration is cis and the acid addition salt is th that of hydrochloric acid, namely, cis 4'-fluoro-4-{[4-(m-methylphenyl)cyclohexyl]amino}butyrophenone hydrochloride.

22. A compound of claim 1 wherein R is p-methyl, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-4-{[4-(p-methylphenyl)cyclohexyl]amino}butyrophenone hydrochloride.

23. A compound of claim 1 wherein R is p-methyl, R' and $R^1$ are hydrogen, $R^2$ is 4-oxo-4-(p-fluorophenyl)butyl, the stereoconfiguration is cis and the acid addition salt is that of hydrochloric acid, namely, cis 4'-fluoro-4-{[4-(p-methylphenyl)cyclohexyl]amino}butyrophenone hydrochloride.

24. A compound of claim 1 wherein R is o-methoxy, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-4-{[4-(o-methoxyphenyl)cyclohexyl]amino}butyrophenone hydrochloride.

25. A compound of claim 1 wherein R is o-methoxy, R' and $R^1$ are hydrogen, $R^2$ is 4-oxo-4-(p-fluorophenyl)butyl, the stereoconfiguration is cis and the acid addition salt is that of hydrochloric acid, namely, cis 4'-fluoro-4-{[4-(o-methoxyphenyl)cyclohexyl-]amino}butyrophenone hydrochloride.

26. A compound of claim 1 wherein R is m-methoxy, R' and $R^1$ are hydrogen, $R^2$ is 4-oxo-4-(p-fluorophenyl)butyl, the stereoconfiguration is trans and the acid addition salt is that of hydrochloric acid, namely, trans 4'-fluoro-4-{[4-(m-methoxyphenyl)cyclohexyl]amino}butyrophenone hydrochloride.

27. A compound of claim 1 wherein R is m-methoxy, R' and R$^1$ are hydrogen, R$^2$ is 4-oxo-4-(p-fluorophenyl)butyl, the stereoconfiguration is cis and the acid addition salt is that of hydrochloric acid, namely, cis 4'-fluoro-4-{[4-(m-methoxyphenyl)cyclohexyl]amino}butyrophenone hydrochloride.

28. A compound of claim 1 wherein R is p-methoxy, R' and R$^1$ are hydrogen, R$^2$ is 4-oxo-4-(p-fluorophenyl)butyl, the stereoconfiguration is trans and the acid addition salt is that of hydrochloric acid, namely, trans 4'-fluoro-4-{[4-(p-methoxyphenyl)cyclohexyl]amino}butyrophenone hydrochloride.

29. A compound of claim 1 wherein R is p-methoxy, R' and R$^1$ are hydrogen, R$^2$ is 4-oxo-4-(p-fluorophenyl)butyl, the stereoconfiguration is cis and the acid addition salt is that of hydrochloric acid, namely, cis 4'-fluoro-4-{[4-(p-methoxyphenyl)cyclohexyl]amino}butyrophenone hydrochloride.

30. A compound of claim 1 wherein R is m-trifluoromethyl, R' and R$^1$ are hydrogen, R$^2$ is 4-oxo-4-(p-fluorophenyl)butyl, the stereoconfiguration is trans and the acid addition salt is that of hydrochloric acid, namely, trans 4'-fluoro-4-{[4-(m-trifluoromethylphenyl)cyclohexyl]amino}butyrophenone hydrochloride.

31. A compound of claim 1 wherein R is m-trifluoromethyl, R' and R$^1$ are hydrogen, R$^2$ is 4-oxo-4-(p-fluorophenyl)butyl, the stereoconfiguration is cis and the acid addition salt is that of hydrochloric acid, namely, cis 4'-fluoro-4-{[4-(m-trifluoromethylphenyl)cyclohexyl]amino}butyrophenone hydrochloride.

32. A compound of claim 1 wherein R is p-trifluoromethyl, R' and R$^1$ are hydrogen, R$^2$ is 4-oxo-4-(p-fluorophenyl)butyl, the stereoconfiguration is trans and the acid addition salt is that of hydrochloric acid, namely, trans 4'-fluoro-4-{[4-(p-trifluoromethylphenyl)cyclohexyl]amino}butyrophenone hydrochloride.

33. A compound of claim 1 wherein R is p-trifluoromethyl, R' and R$^1$ are hydrogen, R$^2$ is 4-oxo-4-(p-fluorophenyl)butyl, the stereoconfiguration is cis and the acid addition salt is that of hydrochloric acid, namely, cis 4'-fluoro-4-{[4-(p-trifluoromethylphenyl)cyclohexyl]amino}butyrophenone hydrochloride.

* * * * *

UNITED STATES PATENT OFFICE
CERTIFICATE OF CORRECTION

Patent No. 3,960,961    Dated    June 1, 1976

Inventor(s)   Daniel Lednicer

It is certified that error appears in the above-identified patent and that said Letters Patent are hereby corrected as shown below:

Column 8,  line 3:       " A compound" should read -- (i)  A compound --
           line 48:      "atoms" should read -- atoms, --
Column 10, line 12:      "-disubstituted" should read -- -(disubstituted --
           line 71:      "phenyl(" should read   -- phenyl) --
Column 11, line 4:       "following" should read -- (following --
Column 15, line 31:      "enbvironment" should read -- environment --
           line 60:      "chlorine" should read -- chloride --
Column 16, line 25:      "administeration" should read -- administration --
           line 60:      "skellysolve" should read -- Skellysolve --
           line 61:      "recystallized" should read -- recrystallized --
Column 17, line 12:      "ddhydrated" should read -- dehydrated --
Column 19, line 9:       "lone" should read -- 1-one --
Column 20, line 29:      "(alkyl)" should read -- (alkyl --
Column 22, lines 24-25:  "temperaturre" should read -- temperature --
           line 30:      "dyrness" should read -- dryness --
Column 23, line 9:       "Following procedure" should read -- Following
                           the procedure --
Column 26, line 54:      "such as 1. trans" should read -- such as (1) trans --
           line 56:      "isopropylisocyanate, 2. trans" should read --
                           isopropylisocyanate, (2) trans --
Column 27, line 47:      "4-p-" should read -- 4-(p- --.
           line 59:      "obtained" should read -- (obtained --
           line 65:      "fluorophehnyl(cyclohexyl[" should read --
                           fluorophenyl)cyclohexyl] --
Column 28, line 13:      "fluorophehyl" should read -- fluorophenyl --
           line 15:      "fluorophenhyl" should read -- fluorophenyl --
           line 18:      "fluorophehyl" should read -- fluorophenyl --
           line 25:      "cis, N" should read -- cis N --
           line 45:      "[4(p-" should read -- [4-(p- --
           line 51:      "[4(o-" should read -- [4-(o- --
Column 29, lines 64-65:  ")obtained" should read -- (obtained --
Column 30, line 16:      "trans" should read -- (1) trans --
Column 31, line 6:       "diemthyl-" should read -- dimethyl --

UNITED STATES PATENT OFFICE

CERTIFICATE OF CORRECTION

Patent No. 3,960,961    Dated June 1, 1976

Inventor(s) Daniel Lednicer

It is certified that error appears in the above-identified patent and that said Letters Patent are hereby corrected as shown below:

| | | |
|---|---|---|
| Column 31, | line 36: | "-4 {[4-" should read -- -4-{[4- -- |
| | line 38: | "-4 {[4-" should read -- -4-{[4- -- |
| | line 58: | "hydrocloride" should read -- hydrochloride -- |
| | line 61: | "66.86 H" should read -- 66.86; H -- |
| | line 62: | "Exammple" should read -- Example -- |
| Column 32, | line 8: | "fluorophehyl" should read -- fluorophenyl -- |
| | lines 10-11: | "hydrochlororide" should read -- hydrochloride -- |
| | lines 12-13: | "hydrochlororide" should read -- hydrochloride -- |
| | lines 19-20: | "hydrochlororide" should read -- hydrochloride -- |
| | line 27: | "4-(o-" should read -- 4-(p- -- |
| | line 53: | "to ° C." should read -- to 200° C. -- |
| | line 56: | "-4{[4-" should read -- -4-{[4- -- |
| Column 33, | line 45: | "c." should read -- C. -- |
| Column 36, | line 50: | "hydoxide" should read -- hydroxide -- |
| Column 37, | line 58: | "4(p-" should read -- 4-(p- -- |
| Column 38, | lines 9-10: | "-cyclohexahone" should read -- -cyclohexanone -- |
| | lines 50-51: | "4-(o-bromo-methyl)" should read -- 4-(o-bromo-methyl) -- |
| Column 41, | line 24: | "-o-" should read -- -p- -- |
| Column 42, | line 33: | "cyclohexlamine" should read -- cyclohexylamine -- |
| | line 39: | "an" should read -- and -- |
| | line 58: | "N-[b 4-(" should read -- N-[4-( -- |
| | line 64: | "fluoro-tolyl)cyclohexlamine" should read -- fluoro-o-tolyl)cyclohexylamine -- |
| Column 43, | lines 4-5: | "cyclohexl" should read -- cyclohexyl -- |
| Column 44, | line 6: | "for" should read -- form -- |
| | line 9: | "lcarbamic" should read -- 1-carbamic -- |
| | line 29: | "cyclohexlamine" should read -- cyclohexylamine -- |
| Column 45, | line 45: | "4(o-" should read -- 4-(o- -- |
| | line 51: | "hydrocloride" should read -- hydrochloride -- |

UNITED STATES PATENT OFFICE
CERTIFICATE OF CORRECTION

Patent No. 3,960,961        Dated June 1, 1976

Inventor(s) Daniel Lednicer

It is certified that error appears in the above-identified patent and that said Letters Patent are hereby corrected as shown below:

| | | |
|---|---|---|
| Column 45, | line 58: | "amine" should read -- amino -- |
| | line 68: | "cyclohexl" should read -- cyclohexyl -- |
| Column 46, | line 6: | "and 2,2-" should read -- and the 2,2- -- |
| | line 13: | "340-bromo" should read -- 3'-bromo -- |
| Column 46, | line 15: | "4-'-" should read -- 4'- -- |
| | line 26: | "Examle" should read -- Example -- |
| | line 32: | "haloalkkanaryl" should read -- haloalkanaryl -- |
| | line 33: | "such cis" should read -- such as cis -- |
| | line 42: | "4(o-" should read -- 4-(o -- |
| | line 43: | "cycloexyl" should read -- cyclohexyl -- |
| | line 48: | "cyclohexylamne" should read -- cyclohexylamine -- |
| | line 58: | "followng" should read -- following -- |
| | lines 59-60: | "tolyl)cyclohexylamne" should read -- tolylcyclohexylamine -- |
| Column 47, | line 2: | "hyrobromide" should read -- hydrobromide -- |
| | line 8: | "1,1bis" should read -- 1,1-bis -- |
| | lines 8-9: | "-21-chloroethane," should read -- 2-chloroethane, -- |
| | line 29: | "4phenyl-" should read -- 4-phenyl -- |
| | line 42: | "4phenyl-" should read -- 4-phenyl- -- |
| | lines 45-46: | "1,4cyclohexanediol" should read -- 1,4-cyclohexanediol -- |
| Column 49, | line 6: | "4phenylcyclohexylamine" should read -- 4-phenylcyclohexylamine -- |
| Column 50, | line 27: | "$C_{14}H_{20}N20$" should read -- $C_{14}H_{20}N_2O$ -- |
| Column 52, | line 40: | "hydochloride" should read -- hydrochloride -- |
| Column 53, | line 12: | "cyclohexyl)]-" should read -- cyclohexyl] -- |
| | line 39: | "methanesulfonamide" should read -- methanesulfonamide (I) -- |
| Column 54, | line 7: | "cyclohexyl" should read -- cyclohexylamine -- |
| | line 26: | "methyl[4-" should read -- methyl-[4- -- |

UNITED STATES PATENT OFFICE
CERTIFICATE OF CORRECTION

Patent No. 3,960,961    Dated June 1, 1976

Inventor(s)  Daniel Lednicer

It is certified that error appears in the above-identified patent and that said Letters Patent are hereby corrected as shown below:

| | |
|---|---|
| Column 54, line 42: | "-1carbamic" should read -- -1-carbamic -- |
| line 54: | "sch" should read -- such -- |
| Column 55, line 16: | "25ml." should read -- 25 ml. -- |
| line 64: | "2,2dimethyl-1,3propanediol" should read -- 2,2-dimethyl-1,3-propanediol -- |
| Column 57, line 1: | "trans4" should read -- trans 4- -- |
| Column 59, line 46: | "is cis" should read -- is trans -- |

Signed and Sealed this

Twenty-first Day of August 1979

[SEAL]

Attest:

LUTRELLE F. PARKER

*Attesting Officer*    *Acting Commissioner of Patents and Trademarks*